US009995751B2

(12) United States Patent
Charretier et al.

(10) Patent No.: US 9,995,751 B2
(45) Date of Patent: Jun. 12, 2018

(54) METHOD FOR DETECTING AT LEAST ONE MECHANISM OF RESISTANCE TO GLYCOPEPTIDES BY MASS SPECTROMETRY

(71) Applicant: BIOMÉRIEUX, Marcy l'Etoile (FR)

(72) Inventors: Yannick Charretier, Courzieu (FR); Jean-Philippe Charrier, Tassin la Demi-Lun (FR); Christine Franceschi, Meximieux (FR); Gilles Zambardi, Chezeneuve (FR)

(73) Assignee: BIOMERIEUX, Marcy L'Etoile (FR)

( * ) Notice: Subject to any disclaimer, the term of this patent is extended or adjusted under 35 U.S.C. 154(b) by 233 days.

(21) Appl. No.: 14/414,773

(22) PCT Filed: Jul. 30, 2013

(86) PCT No.: PCT/FR2013/051833
§ 371 (c)(1),
(2) Date: Jan. 14, 2015

(87) PCT Pub. No.: WO2013/051833
PCT Pub. Date: Jul. 30, 2013

(65) Prior Publication Data

US 2015/0204883 A1 Jul. 23, 2015

(30) Foreign Application Priority Data

Aug. 1, 2012 (FR) ..................................... 12 57489

(51) Int. Cl.
*C12Q 1/04* (2006.01)
*C12Q 1/18* (2006.01)
*G01N 33/68* (2006.01)

(52) U.S. Cl.
CPC ........... *G01N 33/6848* (2013.01); *C12Q 1/04* (2013.01); *C12Q 1/18* (2013.01); *G01N 33/68* (2013.01); *G01N 2333/195* (2013.01)

(58) Field of Classification Search
CPC ... C12Q 1/04; C12Q 1/18; C12Q 1/37; C12Q 2304/00; G01N 33/68; G01N 33/48; G01N 33/6851; G01N 2333/195–2333/365
See application file for complete search history.

(56) References Cited

U.S. PATENT DOCUMENTS

| | | | |
|---|---|---|---|
| 5,770,361 A | 6/1998 | Arthur et al. |
| 6,013,508 A | 1/2000 | Arthur et al. |
| 6,087,106 A | 7/2000 | Arthur et al. |
| 6,569,622 B1 | 5/2003 | Arthur et al. |
| 2004/0229283 A1 | 11/2004 | Gygi et al. |
| 2012/0264156 A1 | 10/2012 | Beaulieu et al. |

FOREIGN PATENT DOCUMENTS

| | | | |
|---|---|---|---|
| FR | 2 668 489 A1 | 4/1992 |
| FR | 2 699 537 A1 | 6/1994 |
| WO | 2005098017 A1 | 10/2005 |
| WO | 2006 128492 A1 | 12/2006 |
| WO | 2008066629 A2 | 6/2008 |
| WO | 2008145763 A1 | 12/2008 |
| WO | 2011/045544 A2 | 4/2011 |

OTHER PUBLICATIONS

Pieper et al. Comparative proteomic analysis of *Staphylococcus* strains with differences in resistance to the cell wall-targeting antibiotic vancomycin. Proteomics. 2006, vol. 6, pp. 4246-4258.*
P.M. Griffin Et Al: "Use of Matrix-Assisted Laser Desorption Ionization-Time of Flight Mass Spectrometry to Identify Vancomycin-Restraint Enterococci and Investigate the Epidemiology of an Outbreak" Journal of Clinical Microbiology. vol. 50, No. 9, pp. 2918-2931, Sep. 2012.
Radhouani Et Al: "Proteomic characterization of vanA-containing Enterococcus recovered from Seagulls at the Berlengas natural Reserve, W Portugal" Proteome Science, Biomed Central; London, Great Britain. vol. 8, No. 1, p. 1-12. Sep. 21, 2010.
S. Sujatha Et Al: "Glycopeptide Resistance in Gram-Positive Cocci: A Review Intedisciplinary Perspectives on Infectious Diseases." vol. 47, No. 6, pp. 902-910. Jan. 1, 2012.
Oct. 22, 2013 International Search Report issued in International Application No. PCT/FR2013/051833.
Anderson, Leigh Et Al: "Quantitative Mass Spectrometric Multiple Reaction Monitoring Assays for Major Plasma Proteins." 2006, pp. 573-578, Molecular and Cellular Proteomics.
Anhalt, John Et Al. "Identification of Bacteria Using Mass Spectrometry." Analytical Chemistry, vol. 47, No. 2, Feb. 1975. pp. 219-225.
Brun, Virginie Et Al. "Isotope-labeled Protein Standards." 2007, Molecular and Cellular Proteomics, pp. 2139-2149.
Bundy, Jonothan Et Al. "Lectin-Based Affinity Capture for MALDI-MS Analysis of Bacteria." Analytical Chemistry, vol. 71, No. 7, Apr. 1999. pp. 1460-1463.
Chen, Wei-Jen Et Al. "Functional Nonoparticle-Based Proteomic Strategies for Characterization of Pathogenic Bacteria." Analytical Chemistry, vol. 80, No. 24, Dec. 2008. pp. 9612-9621.
Claydon, Martin Et Al. "The Rapid Identification of Intact Microorganisms Using Mass Spectometry." Nature Biotechnology, vol. 14, Nov. 1996. pp. 1584-1586.
Desiere, Frank et al. "The PeptideAtlas project." Nucleic Acids Research, 2006, vol. 34. Issue D655-D658.
Ecker, David Et Al. "Ibis T5000: a universal biosensor approach for microbiology." Nature Reviews Microbiology, Jun. 2008.
Everley, Robert Et Al. "Characterization of *Clostridium* species utilizing liquid chromatography/mass spectrometry of intact proteins." Journal of Microbiological Methods, vol. 77, pp. 152-158, 2009.

(Continued)

*Primary Examiner* — Jeffrey E. Russel
(74) *Attorney, Agent, or Firm* — Oliff PLC

(57) ABSTRACT

A method of detection, for at least one microorganism contained in a sample, of at least one marker of resistance to a glycopeptide, including the detection, by mass spectrometry, of at least one peptide or protein of the microorganism. Preferably, the glycopeptide is vancomycin. Preferably, the peptide is derived from a protein of type vanA, vanB, vanC, vanD, vanE, vanG, vanL, vanM or vanN.

23 Claims, No Drawings

(56) References Cited

OTHER PUBLICATIONS

Fenselau, Catherine. "Identification of b-Lactamase in Antibiotic-Resistant Bacillus cereus Spores." Applied and Environmental Microbiology, vol. 74, No. 3, pp. 904-906. Feb. 2008.
Fortin, Tanguy Et Al. "Clinical Qunatitation of Prostate-specific Antigen Biomarker in the Low Nanogram/Milliliter Range by Conventional bore Liquid Chromatography-Tandem Mass spectometry (Multiple Reaction Monitoring) coupling and Correlation with ELISA Tests." 2009 Molecular and Cellular Proteomics, vol. 8, No. 5, pp. 1006-1015.
Fox, Alvin Et Al. "Analytical Microbiology Methods: chromatography and mass spectometry" 1990, Plenum Press, New York, N.Y.
Fusaro, Vincent Et Al. "Prediction of high-responding peptides for targeted protein assays by mass spectrometry." Nature Biotechnology, vol. 27, No. 2, Feb. 2009.
Gaskell, Simon. "Electrospray: Principles and Practice." Journal of Mass Spectrometry, vol. 32, pp. 677-688. 1997.
Han, Bomie Et Al. Proteomics: from hypotesis to quantitative assay on a signle platfom. Guidelines for developing MRM assays using ion trap mass spectrometers. Briefings in Functional Genomics and Proteomics, vol. 7, No. 5. pp. 340-354, (2008).
Hernychova, Lenka. "Detection and Identification of Coxiella burnetii Based on the Mass Spectrometric Analyses of the Extracted Proteins." Analytical Chemistry, vol. 80, No. 18. Sep. 2008.
Hofstadler, Steven Et Al. "TIGER: the universal biosensor" International Journal of Mass Spectrometry, 242, pp. 23-41. 2005.
Keshishian, Hasmik Et Al. "Quantitative, Multiplexed Assays for Low Abundance Proteins in Plasma by Targeted Mass Spectrometry and Stable Isotope Dilution." 2007, Molecular and Cellular Proteomics, pp. 2212-2229.
Krishnamurthy, Thaiya Et Al. "Rapid Identification of Bacteria by Direct Matrix-assisted Laser Desorption/Ionization Mass Spectrometric Analysis of Whole Cells." Rapid Communications in Mass Spectrometry, 1996, vol. 10, pp. 1992-1996.
Lin, Ya-Shluan Et Al. "Affinity Capture Using Vancomycin-Bound Magnetic Nanoparticles for the MALDI-MS Analysis of Bacteria." Analytical Chemistry, vol. 77, No. 6. 1753-1760, Mar. 2005.
Lopez-Ferrer, Daniel Et Al. "On-line Digestion System for Protein Characterization and Proteome Analysis." Analytical Chemistry, vol. 80, No. 23, Dec. 2008. pp. 8930-8936.
Lopez-Ferrer, Daniel Et Al. "Ultra-Fast Trypsin Digestion of Proteins by High Intensity Focused Ultrasound." Journal of Proteome Research. 2005. pp. 1569-1574.
Manes, Nathan Et Al. "Targeted Protein Degradation by *Salmonella* under Phaosome-mimicking Culture Conditions Investigated Using Comparative Peptidomics." 2007, Molecular and Cellular Proteomics, vol. 6, No. 4, pp. 717-727.
Mead, Jennifer Et Al. "MRMaid, the Web-based Tool for Designing Multiple Reaction Monitoring (MRM) Transtitions." Molecular and Cellular Proteomics, Nov. 15, 2008, pp. 696-705.
Nandakumar, Madayiputhiya. "Proteomic analysis of endodontic infections by liquid chromatography-tandem mass spectrometry." Oral Microbiology and Immunology, vol. 24, pp. 347-352, 2009.
Pratt, Julie Et Al. "Multiplexed absolute quantification for proteomics using concatenated signature peptides encoded by QconCAT genes." Nature Protocols, vol. 1, No. 2. pp. 1029-1043, 2006.
Seng, Piseth Et Al. "Ongoing Revolution in Bacteriology: Routine Identification of Bacteria by Matrix-Assisted Laser Desorption Ionization Time-of-Flight Mass Spectrometry." Clinical Infectious Diseases, vol. 49, 543-551, 2009.
Stal-Zeng, Jianru Et Al. High Sensitivity Detection of Plasma Proteins by Multiple Reaction Monitoring of N-Glycosites. Molecular Cellular Proteomics, pp. 1809-1817, (2007).
Vaidyanathan, Seetharaman et al. Discrimination of Aerobic Endospore-forming Bacteria via Electrospray-Ionization Mass Spectrometry of Whole Cell Suspensions. Analytical Chemistry, vol. 73, No. 17, pp. 4134-4144. Sep. 2001.
Oct. 22, 2013 Written Opinion of International Search Report issued in PCT/FR 2013/051833.
Wang Kai-Yi Et. Al. "Multiplexed Immunoassay: Quantitation and Profiling of Serum Biomarkers Using Magnetic Nanoprobes and MALDI-TOF MS." Analytical Chemistry, vol. 80, No. 16. Aug. 2008, pp. 6159-6167.
Teng et al. "Gold Nano Particles as Selective and Concentrating Probes for Samples in MALDI MS Analysis." Analytical Chemistry, vol. 76 pp. 4337-4342, 2004.

* cited by examiner

METHOD FOR DETECTING AT LEAST ONE MECHANISM OF RESISTANCE TO GLYCOPEPTIDES BY MASS SPECTROMETRY

The present invention relates to the field of microbiology. More precisely, the invention relates to the detection, by mass spectrometry, of at least one mechanism of resistance to glycopeptides of at least one microorganism obtained from a sample.

Since the discovery of microbes by Pasteur, microorganisms have been studied by microscopy and biochemical analyses. These traditional methods are often long and tedious and analytical alternatives were soon required. Thus, analysis of bacteria by mass spectrometry was begun in 1975 by J. Anhalt and C. Fenselau [1].

This preliminary work was followed by the use of gas chromatography coupled to mass spectrometry (GC-MS) for studying fatty acids of the cell wall of microorganisms [2]. This method became popular under the English name FAME for Fatty Acid Methyl Ester. It now constitutes a reference method for taxonomic studies. However, its use is still limited to certain specialized laboratories able to treat the sample by saponification, hydrolysis and derivation.

In 1996, the works of M. Claydon et al. [3] and of T. Krishnamurthy and P. Ross [4] showed that it is possible to identify various bacterial species with a mass spectrometer of the MALDI-TOF type (Matrix Assisted Laser Desorption Ionization-Time Of Flight). Analysis combines acquisition of a mass spectrum and interpretation by expert software. It is extremely simple and can be performed in a few minutes. It is currently being adopted in medical analysis laboratories [5]. Its clinical use, however, is limited to identification of bacterial species and yeasts. It is not used routinely for identifying resistance to antimicrobials.

Now, identification of resistance to antimicrobials such as antibiotics is an essential element for ensuring optimal patient management.

Other methods of mass spectrometry, notably in tandem, have been proposed for addressing these needs. As an example, we may mention the works of C. Fenselau et al., for identifying β-lactamase with a quadrupole-TOF (Q-TOF) [6]. However, these research results are not applicable to routine clinical use. They were obtained with research instruments requiring highly qualified personnel. The analysis times, often more than one hour per sample, are incompatible with the workload of a microbiological analysis laboratory.

More recently, S. Hofstadler et al. [7] proposed a method combining amplification of the microbial genome by PCR with detection of the PCR products by electrospray-TOF (ESI-TOF). This method is now fully automated [8]. However, it requires amplification by PCR with the inherent faults of molecular biology, namely extraction yield, cost of probes, etc.

In this context, the aim of the present invention is to propose a method for detecting mechanisms of resistance to glycopeptides that allows the drawbacks of the methods of the prior art to be overcome, namely to supply a low-cost method, without a reagent specific to each species, notably relative to the methods of molecular biology, giving a result in a short time, less than one hour, and usable in routine clinical practice, without requiring highly qualified personnel.

For this purpose, the invention proposes a new method of detection, for at least one microorganism contained in a sample, of at least one marker of resistance to a glycopeptide, comprising the detection, by mass spectrometry, of at least one peptide or protein of said microorganism.

Advantageously, markers of resistance to several different antimicrobials can be detected simultaneously.

Surprisingly and unexpectedly, the method of the present invention makes it possible to detect the existence of inducible mechanisms of resistance, in the absence of induction.

As indicated in application WO2011045544, markers of typing and/or of virulence of microorganisms can be detected, in the same way, by mass spectrometry, prior to or simultaneously with detection of the mechanism of resistance markers.

"Markers of resistance to at least one antimicrobial of the class of glycopeptides" means molecules of protein origin that are characteristic of said properties of resistance.

The glycopeptides are antibiotics such as vancomycin, teicoplanin, telavancin, bleomycin, ramoplanin, and decaplanin. Vancomycin is a glycopeptide proper, teicoplanin is a lipoglycopeptide. These two molecules inhibit synthesis of the bacterial wall by inhibition of the synthesis of the peptidoglycan. In fact, their pocket-shaped three-dimensional structure covers the dipeptide D-Ala D-Ala precursor of synthesis of the peptidoglycan, prevents the action of glycosyltransferases and transpeptidases and blocks elongation of the peptidoglycan. Resistance to glycopeptides is due to the presence of operons encoding enzymes catalyzing the formation of low-affinity precursors and enzymes eliminating the high-affinity precursors produced by the host bacterium. Various types of resistance are known, depending on the enzymes present in the operon. Classification of resistance to glycopeptides is based on the primary sequence of the structural genes of the resistance ligases rather than on the levels of resistance to the glycopeptides, to the extent that the minimum inhibitory concentrations (MIC) of the various types overlap. Nine types of resistance have been identified. Eight result from acquired resistance (VanA, B, D, E, G, L, M and N) and one (VanC) is a natural resistance present in *E. gallinarum* and to *E. casseliflavus*. (for a review see [9], Sujatha, S. & Praharaj, I. Glycopeptide Resistance in Gram-Positive Cocci: A Review. Interdiscip. Perspect. Infect. Dis 2012, 781679 (2012))

The VanA type of resistance is characterized by a high-level inducible resistance to vancomycin and to teicoplanin. Note that transmission of the VanA type to *S. aureus* has been demonstrated but is nevertheless quite rare.

The VanB type of resistance is characterized by an inducible resistance of moderate to high level to vancomycin and is sensitive to teicoplanin.

In general, the VanA and VanB phenotypes are the most important clinical cases and are frequently found in *E. faecalis* and in *E. faecium.*

The VanD type of resistance is characterized by a constitutive resistance of moderate level to vancomycin and to teicoplanin.

The types of resistance VanC, E, G, L and N are characterized by a low-level resistance to vancomycin and by sensitivity to teicoplanin.

Resistance may be expressed in the absence of antibiotic, it is then called constitutive. It may also be expressed in the presence of a certain concentration of antibiotic, it is then called inducible. Culture of the microorganism in the presence of a certain concentration of antibiotic is then called culture with induction.

Determination of resistance to at least one antimicrobial means that it is impossible to destroy the bacteria or inhibit their multiplication at a defined concentration as a function of the pharmacodynamic and pharmacokinetic parameters characteristic of each antibiotic.

Determination of a mechanism of resistance to at least one antibiotic means detecting at least one compound synthesized by the bacterium, enabling it to evade, at least partially, the action of the antibiotic, most often by modification of the structure of the antibiotic or of its metabolic target, or else by its reduced penetration into the bacterium. Preferably, said compound synthesized by the bacterium is a protein.

The method of the invention may be employed for detecting mechanisms of resistance to glycopeptides in bacteria. Thus, for example, as bacteria for which it is possible to investigate a mechanism of resistance to glycopeptides according to the method of the invention, we may mention, nonexhaustively: *Enterococcus faecalis, Enterococcus faecium, Enterococcus gallinarum, Enterococcus casseliflavus, Enterococcus durans, Enterococcus avium, Enterococcus raffinosus* or *Staphylococcus aureus*. The agents primarily responsible for infections are the Enterococci and more particularly *Enterococcus faecalis* and *Enterococcus faecium.*

Thus, the method according to the invention also makes it possible to detect a mechanism of resistance to said antibiotics.

"Sample" means a small part or small isolated amount of an entity for analysis. The sample on which the method of the invention may be implemented is any sample that may contain a target microorganism. The sample may be of biological origin, either animal, vegetable or human. It may then correspond to a sample of biological fluid (whole blood, serum, plasma, urine, cerebrospinal fluid, organic secretion, for example), a tissue sample or isolated cells. This sample may be used as it is, i.e. the markers of the mechanisms of resistance of the bacteria to glycopeptides are potentially detectable directly in the sample tested, or else it may undergo, prior to analysis, a preparation such as enrichment, extraction, concentration, purification, culture, according to methods known by a person skilled in the art.

The sample may be of industrial origin, or, according to a nonexhaustive list, a sample of air, a sample of water, a sample taken from a surface, an article or a manufactured product, a product of food origin. Among the samples of food origin, we may mention nonexhaustively a sample of a milk product (yoghurts, cheeses), of meat, of fish, of egg, of fruit, of vegetable, of water, of drink (milk, fruit juice, soda, etc.). These samples of food origin may also come from sauces or from prepared dishes. A food sample may finally be obtained from feed intended for animals, notably such as animal feed meal.

Upstream of detection by mass spectrometry, the sample to be analyzed is preferably treated beforehand to generate peptides from all of the proteins present in the sample, to fragment these proteins into peptides, for example by digestion with a proteolytic enzyme (protease), or by the action of a chemical reagent. In fact, cleavage of the proteins may be brought about by a physicochemical treatment, by a biological treatment or by a combination of both treatments. Among the treatments usable, we may mention treatment with hydroxyl radicals, notably with $H_2O_2$. Treatment with hydroxyl radicals causes cleavage of the peptide bonds, which occurs randomly on any peptide bond of the protein. The concentration of hydroxyl radicals determines the number of cleavages performed and therefore the length of the peptide fragments obtained. Other chemical treatments may also be used, such as, for example, treatment with cyanogen bromide (BrCN) which specifically cleaves the peptide bonds at the level of the carboxyl group of the methionyl residues. It is also possible to perform partial acid cleavage at the level of the aspartyl residues by heating a solution of proteins in trifluoroacetic acid at 1000° C.

Treatment of the proteins by enzymatic digestion is nevertheless preferred over physicochemical treatment as it preserves the structure of the proteins more, and is easier to control. "Enzymatic digestion" means the single or combined action of one or more enzymes in suitable reaction conditions. The enzymes performing proteolysis, called proteases, cut the proteins in specific places. Each protease generally recognizes an amino acid sequence, within which it always makes the same cut. Certain proteases recognize a single amino acid or a sequence of two amino acids between which they perform a cleavage, other proteases only recognize longer sequences. These proteases may be endoproteases or exoproteases. Among the known proteases, we may mention, as described in WO2005/098017:

specific enzymes such as trypsin which cleaves the peptide bond at the level of the carboxyl group of the residues Arg and Lys, endolysin which cleaves the peptide bond of the —CO group of the lysines, chymotrypsin which hydrolyzes the peptide bond at the level of the carboxyl group of the aromatic residues (Phe, Tyr and Trp), pepsin which cleaves the aromatic residues (Phe, Tyr and Trp) at the level of the $NH_2$ group, protease V8 of the V8 strain of *Staphylococcus aureus* which cleaves the peptide bond at the level of the carboxyl group of the residue GI u;

nonspecific enzymes such as thermolysin derived from the bacterium *Bacillus thermoproteolyticus* which hydrolyzes the peptide bond of the $NH_2$ group of the hydrophobic amino acids (Xaa-Leu, Xaa-Ile, Xaa-Phe), subtilisin and pronase which are bacterial proteases which hydrolyze practically all the bonds and can transform the proteins to oligopeptides in controlled reaction conditions (concentration of enzyme and reaction time).

Several proteases may be used simultaneously, if their modes of action are compatible, or they may be used successively. In the context of the invention, the sample is preferably digested by the action of a protease enzyme, for example trypsin.

Generation of peptides using a chemical reagent or a protease may be obtained by simple reaction in solution. It may also be carried out with a microwave oven [10], or under pressure [11], or else with an ultrasonic device [12]. In these last three cases, the protocol will be much quicker.

Among the peptides thus obtained, the specific peptides of the protein are called proteotypic peptides. These are the ones that will be determined by mass spectrometry.

According to the invention, the markers of the mechanisms of resistance of bacteria to glycopeptides are proteins of the bacterium in which the mechanisms of resistance to glycopeptides are to be investigated. In particular, said proteins are digested to peptides, preferably by an enzyme, more preferably by trypsin.

Moreover, the sample containing protein markers characterizing mechanisms of bacteria's resistance to glycopeptides may also be treated beforehand for purposes of purification. This preliminary purification treatment may be carried out before or after the step for generating peptides as described above.

The preliminary sample purification treatment is generally known by a person skilled in the art and may notably employ techniques of centrifugation, filtration, electrophoresis or chromatography. These separation techniques may be used alone or combined with one another to obtain multidimensional separation. For example, multidimensional chromatography may be used, combining separation by ion exchange chromatography with reversed-phase chromatography, as described by T. Fortin et al. [13], or H.

Keshishian et al. [14]. In these works, the chromatographic medium may be in a column or in a cartridge (solid phase extraction).

The electrophoretic or chromatographic fraction (or retention time in uni- or multidimensional chromatography) of the proteotypic peptides is characteristic of each peptide and application of these techniques therefore makes it possible to select the proteotypic peptide or peptides to be determined. This fractionation of the peptides generated makes it possible to increase the specificity of subsequent determination by mass spectrometry.

An alternative to the techniques of electrophoresis or chromatography for fractionation of the peptides consists of purifying the N-glycopeptides specifically ([15] and patent application WO 2008/066629). However, purification of this kind only allows quantification of the peptides that have undergone a post-translational modification of the N-glycosylation type. Now, not all of the proteins are glycosylated, which therefore limits its use.

The mass spectrometry to be employed in the method of the invention is widely known by a person skilled in the art as a powerful tool for analysis and detection of different types of molecules. In general, any type of molecule that can be ionized can be detected as a function of its molecular weight using a mass spectrometer. Depending on the nature of the molecule to be detected, of protein origin or of metabolic origin, particular technologies of mass spectrometry may be more suitable. Nevertheless, regardless of the method of mass spectrometry used for detection, the latter comprises a step of ionization of the target molecule into so-called molecular ions, in the present case a step of ionization of the characterizing markers, and a step of separation of the molecular ions obtained as a function of their mass.

All mass spectrometers comprise:

- an ionization source for ionizing the markers present in the sample to be analyzed, i.e. to confer a positive or negative charge on these markers;
- a mass analyzer for separating the ionized markers, or molecular ions, as a function of their mass-to-charge ratio (m/z);
- a detector for measuring the signal produced either directly by the molecular ions, or by ions produced from the molecular ions, as detailed below.

The ionization step necessary for carrying out mass spectrometry may be performed by any method known by a person skilled in the art. The ionization source allows the molecules to be determined to be brought into an ionized gaseous state. An ionization source may be used either in positive mode for studying the positive ions, or in negative mode for studying the negative ions. There are several types of sources and they will be used depending on the result required and the molecules analyzed. We may mention, notably:

- electron ionization (EI), chemical ionization (CI) and desorption chemical ionization (DCI)
- fast atom bombardment (FAB), metastable atom bombardment (MAB) or ion bombardment (SIMS, LSIMS)
- inductively coupled plasma (ICP)
- atmospheric pressure chemical ionization (APCI) and atmospheric pressure photoionization (APPI)
- electrospray (ESI)
- matrix-assisted laser desorption/ionization (MALDI), surface-enhanced desorption/ionization (SELDI) or desorption/ionization on silicon (DIOS)
- ionization-desorption by interaction with metastable species (direct analysis in real time, DART)

Notably, ionization may be carried out as follows: the sample containing the target molecules is introduced into an ionization source, where the molecules are ionized in the gaseous state and thus transformed into molecular ions that correspond to the initial molecules. An ionization source of the electrospray type (ESI, for electrospray ionization) allows a molecule to be ionized while converting it from a liquid state to a gaseous state. The molecular ions obtained then correspond to the molecules present in the liquid state, with, in positive mode, one, two, or even three additional protons or more and are therefore carriers of one, two, or even three charges or more. For example, when the target molecule is a protein, ionization of the proteotypic peptides obtained after fractionation of the target protein, using a source of the electrospray type operating in positive mode, leads to polypeptide ions in the gaseous state, with one, two, or even three additional protons or more and which are therefore carriers of one, two, or even three charges or more, and allows transition from a liquid state to a gaseous state [16]. This type of source is particularly suitable when the target molecules or proteotypic peptides obtained are separated beforehand by reversed-phase liquid chromatography. However, the ionization yield of the molecules present in the sample may vary as a function of the concentration and nature of the different species present. This phenomenon is reflected in a matrix effect that is well known by a person skilled in the art.

A MALDI ionization source will allow molecules to be ionized from a sample in the solid state.

The mass analyzer in which the step of separation of the ionized markers is carried out as a function of their mass/charge ratio (m/z) is any mass analyzer known by a person skilled in the art. We may mention the low-resolution analyzers, of quadrupole (Q), 3D ion trap (IT) or linear type (LIT), also called ion trap analyzers, and the high-resolution analyzers, allowing the exact mass of the analytes to be measured, and which notably use the magnetic sector coupled to an electric sector, time of flight (TOF), Fourier transform ion cyclotron resonance (FT-ICR), Orbitrap.

Separation of the molecular ions as a function of their m/z ratio may be performed once (single mass spectrometry or MS), or else several successive MS separations may be carried out. When two successive MS separations are carried out, the analysis is called MS/MS or $MS^2$. When three successive MS separations are carried out, the analysis is called MS/MS/MS or $MS^3$, and more generally, when n successive MS separations are performed, the analysis is called $MS^n$.

Among the techniques employing several successive separations, SRM mode (Selected Reaction Monitoring) in the case of detection or assay of a single target molecule, or else MRM mode (Multiple Reaction Monitoring) in the case of detection or assay of several target molecules, are particular applications of $MS^2$ separation. Similarly, the $MRM^3$ mode is a particular application of MS/MS/MS separation. This is then called targeted mass spectrometry.

In the case of detection in single MS mode, it is the mass/charge ratio of the molecular ions obtained that is correlated with the target molecule to be detected. In the case of detection in MS/MS mode, essentially two steps are added, relative to MS determination, which are:

- fragmentation of the molecular ions, which are then called precursor ions, to give ions called first-generation fragment ions, and
- separation of the ions called first-generation fragment ions as a function of their mass $(m/z)_2$, the ratio $(m/z)_1$ corresponding to the (m/z) ratio of the precursor ions.

It is then the mass/charge ratio of the first-generation fragment ions thus obtained that is correlated with the target molecule to be detected. First-generation fragment ion means an ion derived from the precursor ion, following a fragmentation step, and whose mass-to-charge ratio m/z is different from the precursor ion.

The pairs $(m/z)_1$ and $(m/z)_2$ are called transitions and are representative of the characteristic ions to be detected.

The characteristic ions that are detected in order to be correlated with the target molecule are selected by a person skilled in the art according to standard methods. Selection of them will advantageously lead to assays that are the most sensitive, the most specific and the most robust as possible, in terms of reproducibility and reliability. In the methods developed for the selection of proteotypic peptides $(m/z)_1$, and of first-generation fragment $(m/z)_2$, the choice is essentially based on the intensity of the response. For more detail, reference may be made to V. Fusaro et al. [17]. Commercial software, such as the MIDAS and MRM Pilote software from Applied Biosystems or else MRMaid [18] will be able to be used by a person skilled in the art for predicting all the possible pairs of transitions. It will also be possible to use a database called PeptideAtlas, constructed by F. Desiere et al. [19] for compiling all the MRM transitions of peptides described by the scientific community. This PeptideAtlas database is available with free access on the Internet. For nonprotein molecules, it is also possible to use databases, for example that accessible via the Cliquid software from the company Applied Biosystems (United States of America).

An alternative approach for selecting the proteotypic peptides, $(m/z)_1$ and $(m/z)_2$, consists of using the MS/MS fragmentation spectra obtained in other work. This work may be, for example, the stages of discovery and identification of the biomarkers by proteome analysis. This approach was proposed by Thermo Scientific at user conferences [18]. It makes it possible to generate a list of candidate transitions from the peptides identified experimentally with the SIEVE software (Thermo Scientific). Certain criteria have been detailed by J. Mead et al. [18] for selecting the ions $(m/z)_1$ and $(m/z)_2$ and are detailed below:

- the peptides with internal cleavage sites, i.e. with internal lysine or arginine, must be avoided, unless the lysine or arginine is followed by proline,
- the peptides with asparagine or glutamine must be avoided as they may undergo deamination,
- the peptides with glutamine or glutamic acid at the N-terminus must be avoided as they may cyclize spontaneously,
- the peptides with methionine must be avoided as they may undergo oxidation,
- the peptides with cysteine must be avoided as they may be modified nonreproducibly during an optional step of denaturation, reduction and blocking of the thiol functions,
- the peptides with proline may be regarded as favorable because they generally produce intense fragments in MS/MS with a single, very predominant peak. However, a single very predominant fragment does not allow validation of the identity of the transition in a complex mixture. In fact, only the simultaneous presence of several characteristic fragments makes it possible to verify that the required precursor ion is in fact detected,
- the peptides having a proline adjacent to the C-terminus (position n-1) or in second position relative to the C-terminus (position n-2) are to be avoided because in this case the size of first-generation fragment peptide is generally considered to be too small to be sufficiently specific,
- selection of fragments having a mass greater than the precursor is to be preferred, to promote specificity. For this, it is necessary to select a double-charged precursor ion and select the most intense first-generation fragment ion having a mass greater than the precursor, i.e. a single-charged first-generation fragment ion.

Fragmentation of the selected precursor ions is carried out in a fragmentation cell such as the models of the triple quadrupole type [20], or ion trap type [21], or else of the time of flight (TOF) type [22], which also allow separation of the ions. The fragmentation or fragmentations will be carried out conventionally by collision with an inert gas such as argon or nitrogen, within an electric field, by photo-excitation or photodissociation using an intense light source, collision with electrons or radical species, by application of a potential difference, for example in a time-of-flight tube, or by any other method of activation. The characteristics of the electric field determine the intensity and the nature of fragmentation. Thus, the electric field applied in the presence of an inert gas, for example in a quadrupole, determines the collision energy supplied to the ions. This collision energy will be optimized, by a person skilled in the art, to increase the sensitivity of the transition to be determined. As an example, it is possible to vary the collision energy between 5 and 180 $e^{-}V$ in q2 in an AB SCIEX QTRAP® 5500 mass spectrometer from the company Applied Biosystems (Foster City, United States of America). Similarly, the duration of the collision step and the excitation energy within, for example, an ion trap will be optimized, by a person skilled in the art, to lead to the most sensitive determination. As an example, it is possible to vary this duration, dubbed excitation time, between 0.010 and 50 ms and the excitation energy between 0 and 1 (arbitrary unit) in Q3 in an AB SCIEX QTRAP® 5500 mass spectrometer from the company Applied Biosystems. Finally, detection of the selected characteristic ions is performed conventionally, notably using a detector and a processing system. The detector collects the ions and produces an electrical signal whose intensity depends on the quantity of ions collected. The signal obtained is then amplified for processing by computer. A data-processing computer system allows the data received by the detector to be converted to a mass spectrum.

The principle of the SRM mode, or of the MRM mode, is to select a precursor ion specifically, fragment it, and then select one of its fragment ions specifically. For such applications, devices of the triple quadrupole type or ion-trap triple quadrupole hybrids are generally used.

In the case of a triple quadrupole device (Q1q2Q3) used in $MS^2$ mode, for determining or detecting a target protein, the first quadrupole (Q1) makes it possible to filter the molecular ions corresponding to the proteotypic peptides characteristic of the protein to be assayed, obtained in a previous digestion step, as a function of their mass-to-charge ratio (m/z). Only the peptides having the mass/charge ratio of the required proteotypic peptide, the ratio called $(m/z)_1$, are transmitted into the second quadrupole (q2) and play the role of precursor ions for subsequent fragmentation. The q2 analyzer makes it possible to fragment the peptides of mass/charge ratio $(m/z)_1$ into first-generation fragment ions. Fragmentation is generally obtained by collision of the precursor peptides with an inert gas, such as nitrogen or argon in q2. The first-generation fragment ions are transmitted into a third quadrupole (Q3) which filters the first-generation fragment ions as a function of a specific mass-to-charge ratio, the ratio called $(m/z)_2$. Only the first-generation fragment ions having the mass/charge ratio of a fragment characteristic of the required proteotypic peptide $(m/z)_2$ are transmitted into the detector to be detected, or even quantified.

This operating mode displays dual selectivity, in relation to selection of the precursor ion on the one hand and selection of the first-generation fragment ion on the other hand. Mass spectrometry in SRM or MRM mode is therefore advantageous for quantification.

When the mass spectrometry employed in the method of the invention is tandem mass spectrometry ($MS^2$, $MS^3$, $MS^4$ or $MS^5$), several mass analyzers may be coupled together. For example, a first analyzer separates the ions, a collision cell allows the ions to be fragmented, and a second analyzer separates the fragment ions. Certain analyzers, such as ion traps or FT-ICR, constitute several analyzers in one and make it possible to fragment the ions and analyze the fragments directly.

According to preferred embodiments of the invention, the method of the invention comprises one or more of the following characteristics:

the mass spectrometry employed for the properties of potential resistance to at least one antimicrobial is spectrometry of the MS/MS type, which has the advantage of generating a specific fragment of the molecule to be detected or to be quantified, and thus of giving the assay method great specificity;

the MS/MS spectrometry is MRM spectrometry, which has the advantage of using an analysis cycle time in the mass spectrometer of some tens of milliseconds, which makes it possible to detect or quantify with great sensitivity, in a multiplexed fashion, a large number of different molecules;

if applicable, determination of the typing properties, and of the virulence factor is employed in the same mass spectrometry apparatus as determination of the markers of resistance to at least one antimicrobial, preferably simultaneously, which has the advantage of reducing the analysis times and the equipment cost; this also facilitates processing and presentation of the results.

Besides determination of the resistance to an antibiotic, it is appropriate to identify the microorganism or microorganisms present in the test sample.

The methods of identification of microorganisms are widely known by a person skilled in the art, as described for example by Murray P. R. et al. in Manual of Clinical Microbiology, 2007, 9th edition, and in particular in Vol. I, Section III, chapters 15 and 16 for bacteria and yeasts, Vol. II, Section VI, chapter 82 for viruses, and Vol. II, Section X, chapter 135 for protozoa. As examples of classical methods of identification, we may mention determination of the biological profile, using for example the Vitek 2 identification cards (bioMérieux™), or else using techniques of molecular biology with identification criteria based on investigation for the presence of certain genes, and investigation of their sequence. Identification may be carried out directly from the sample in which the identification is being effected, or else the microorganisms contained in the sample may be cultured by methods that are familiar to a person skilled in the art with optimal culture media and culture conditions adapted in relation to the species of microorganisms to be investigated, as described by Murray P. R. et al. in Manual of Clinical Microbiology, 2007, 9th edition, Vol. I, Section III, chapter 14, and in particular in Vol. I, Section IV, chapter 21 for bacteria, Vol. II, Section VI, chapter 81 for viruses, Vol. II, Section VIII, chapter 117 for yeasts, and Vol. II, Section X, chapter 134 for protozoa.

Thus, generally, in the case of identification of a bacterium in a sample by a biochemical method, it is first necessary to obtain it in culture pure, for example after seeding on agar. Molecular biology (PCR) may in certain cases be applied directly to the sample to be analyzed.

Instead of culturing the microorganisms, the latter may be concentrated by direct capture in the sample by means of active surfaces. Such a method has been described by W.-J. Chen et al. [10], who captured various bacterial species using magnetic beads with a surface activated with $Fe_3O_4/TiO_2$. Capture by other means is also possible, such as capture by lectins [23], or by antibodies [24], or by vancomycin [25]. Capture makes it possible to concentrate the microorganisms and thus reduce or even eliminate the culture step. This results in a considerable saving of time.

Identification may also be carried out by mass spectrometry, according to the techniques described above, preferably by MS, by MS/MS, or else by MS followed by spectrometry of the MS/MS type, which constitutes one embodiment of the invention. In this case as well, the sample may be submitted beforehand to a culture step such as seeding on agar.

Use of a method of identification by MS is advantageous in that it can be carried out in a few minutes and in that it requires a mass spectrometer with a single analyzer, i.e. an instrument that is less complex than a tandem mass spectrometer used in MS/MS.

Use of a method of identification by MS followed by spectrometry of the MS/MS type is also advantageous. It provides assurance of the identity of the ions observed in MS, which increases the specificity of the analysis.

Use of a method of identification by MS/MS of the MRM type has the advantage of being more sensitive and simpler than the approaches MS then traditional MS/MS. This method does not require powerful software, which is necessary for processing information between acquisition of the MS spectrum and of the MS/MS spectrum, and does not require resetting of the machine variables, necessary for the succession of MS and then MS/MS spectra.

The method of identification by MS may be carried out with an electrospray source on a raw sample, as described by S. Vaidyanathan et al. [26] or by R. Everley et al. [27] after chromatographic separation. Different m/z ranges then allow the microorganisms to be identified. S. Vaidyanathan et al. used a window between 200 and 2000 Th, and R. Everley et al. used a window between 620 and 2450 Th. The mass spectra may also be deconvoluted to find the mass of the proteins independently of their state of charge. R. Everley et al. thus exploited masses between about 5000 and 50 000 Da. Alternatively, the method of identification by MS may also be carried out using MALDI-TOF, as described by Claydon et al. [3] and T. Krishnamurthy and P. Ross [4]. Analysis combines acquisition of a mass spectrum and interpretation by expert software. It is extremely simple and can be performed in a few minutes. This method of identification is currently being adopted in medical analysis laboratories [5].

Identification of bacteria by MS and then MS/MS via their proteins present in the sample has been widely applied by many teams. As an example, we may cite the recent works of Manes N. et al. [28], who studied the peptidome of *Salmonella enterica*, or the works of R. Nandakumar et al. [29] or of L. Hernychova et al. [30], who studied the proteome of bacteria after digestion of the proteins with trypsin. The classical approach consists of i) acquiring an MS spectrum, ii) successively selecting each precursor ion observed on the MS spectrum with a strong signal, iii) successively fragmenting each precursor ion and acquiring its MS/MS spectrum, iv) interrogating protein databases such as SWISS-PROT or NCBI, using software such as Mascot (Matrix Science, London, United Kingdom) or SEQUEST (Thermo Scientific, Waltham, United States of America), to identify the peptide having a high probability of corresponding to the MS/MS spectrum observed. This method may lead to identification of a microorganism if a protein or a peptide characteristic of the species is identified.

One of the advantages of using mass spectrometry is that it is particularly useful for quantifying molecules, in the present case the markers of the mechanisms of resistance of bacteria to the glycopeptides. For this purpose, the current intensity detected is used, which is proportional to the quantity of the target molecule. The current intensity thus measured can serve as a quantitative measure for determining the quantity of target molecule present, which is characterized by expression in units of the International System (Système International, SI) of the type mol/$m^3$ or kg/$m^3$, or by multiples or submultiples of these units, or by the usual derivatives of the SI units, including their multiples or submultiples. As a nonlimiting example, units such as ng/ml or fmol/l are units characterizing a quantitative measurement.

However, calibration is necessary so as to be able to correlate the measured peak area, corresponding to the current intensity induced by the ions detected, with the quantity of the assayed target molecule. For this, the calibrations conventionally used in mass spectrometry can be used in the context of the invention. MRM assays are conventionally calibrated using external standards or, preferably, using internal standards as described by T. Fortin et al. [13]. In the case when the target molecule is a proteotypic peptide, allowing assay of a protein of interest, the correlation between the quantitative measurement and the quantity of target proteotypic peptide, and then the protein of interest, is obtained by calibrating the measured signal relative to a standard signal for which the quantity to be assayed is known. Calibration may be performed by means of a calibration curve, for example obtained by successive injections of standard proteotypic peptide at different concentrations (external calibration), or preferably by internal calibration using a heavy peptide, as internal standard, for example according to the AQUA, QconCAT or PSAQ methods detailed below. "Heavy peptide" means a peptide corresponding to the proteotypic peptide, but in which one or more atoms of carbon 12 ($^{12}C$) is (are) replaced with carbon 13 ($^{13}C$), and/or one or more atoms of nitrogen 14 ($^{14}N$) is (are) replaced with nitrogen 15 ($^{15}N$).

The use of heavy peptides, as internal standards (AQUA), was also proposed in patent application US 2004/0229283. The principle is to synthesize proteotypic peptides artificially with amino acids comprising isotopes heavier than the usual natural isotopes. Amino acids of this kind are obtained, for example, by replacing some of the atoms of carbon 12 ($^{12}C$) with carbon 13 ($^{13}C$), or by replacing certain of the atoms of nitrogen 14 ($^{14}N$) with nitrogen 15 ($^{15}N$). The artificial peptide (AQUA) thus synthesized has strictly the same physicochemical properties as the natural peptide (except for a higher mass). It is generally added, at a given concentration, to the sample, upstream of assay by mass spectroscopy, for example between the treatment leading to cleavage of the proteins of the sample of interest and fractionation of the peptides obtained after the treatment step. Accordingly, the AQUA peptide is co-purified with the natural peptide to be assayed, during fractionation of the peptides. The two peptides are therefore injected simultaneously into the mass spectrometer, for assay. They are then subjected to the same ionization yields in the source. Comparison of the peak areas of the natural peptides and AQUA peptides, whose concentration is known, makes it possible to calculate the concentration of the natural peptide and thus arrive at the concentration of the protein to be assayed. A variant of the AQUA technique was proposed by J.-M. Pratt et al. [31] under the name QconCat. This variant is also described in patent application WO 2006/128492. It consists of concatenating various AQUA peptides and of producing the artificial polypeptide in the form of heavy recombinant protein. The recombinant protein is synthesized with amino acids comprising heavy isotopes. In this way it is possible to obtain a standard for calibrating the simultaneous assay of several proteins at lower cost. The QconCAT standard is added at the very start, upstream of the treatment leading to cleavage of the proteins and before the steps of fractionation of the proteins, denaturation, reduction and then blocking the thiol functions of the proteins, if the latter are present. The QconCAT standard therefore undergoes the same cycle of treatment leading to cleavage of the proteins as the natural protein, which makes it possible to take account of the yield of the treatment step leading to cleavage of the proteins. In fact, the treatment, notably by digestion, of the natural protein may not be complete. In this case the use of an AQUA standard would lead to underestimating the quantity of natural protein. For an absolute assay, it may therefore be important to take into account the yields of treatment leading to cleavage of the proteins. However, V. Brun et al. [33] showed that sometimes the QconQAT standards did not reproduce exactly the yield of treatment notably by digestion of the natural protein, without doubt owing to a three-dimensional conformation different from the QconCAT protein. V. Brun et al. [32] then proposed using a method dubbed PSAQ and described in patent application WO 2008/145763. In this case, the internal standard is a recombinant protein, having the same sequence as the natural protein but synthesized with heavy amino acids. The synthesis is carried out ex vivo with heavy amino acids. This standard has strictly the same physicochemical properties as the natural protein (except for a higher mass). It is added at the very start, before the step of fractionation of the proteins, when the latter is present. It is therefore co-purified with the native protein, during the step of fractionation of the proteins. It displays the same yield of treatment, notably by digestion, as the native protein. The heavy peptide obtained after cleavage is also co-purified with the natural peptide, if a step of fractionation of the peptides is carried out. The two peptides are therefore injected simultaneously into the mass spectrometer, to be assayed quantitatively. They are then subjected to the same ionization yields in the source. Comparison of the peak areas of the natural peptides and reference peptides in the PSAQ method makes it possible to calculate the concentration of the protein to be assayed taking into account all of the steps of the assay procedure.

All of these techniques, namely AQUA, QconCAT or PSAQ or any other calibration technique used in assays by mass spectrometry and in particular in MRM or MS assays, can be used for performing the calibration, in the context of the invention.

Preferably, the mass spectrometry used in the method of detection according to the invention is of the MS/MS type. More preferably, the mass spectrometry is MRM.

The method of the invention allows detection of resistances to glycopeptides, characterized by the detection of at least one peptide as resistance marker. Preferably, the method according to the invention makes it possible to detect at least one marker of resistance to vancomycin.

According to a first embodiment, the method according to the invention allows direct detection of resistance to a glycopeptide, without bringing the microorganism potentially present in the sample into contact with said glycopeptide, i.e. without a step of induction of said resistance.

According to another embodiment, the method of the invention comprises an additional step, prior to the detection step, consisting of induction of the mechanism of resistance by bringing said sample into contact with said glycopeptide(s).

Preferably, said resistance marker is a peptide derived from the proteins of the Van type, such as the respective variants of type Van A, Van B, Van C, Van D, Van E, Van G, Van L, Van M and Van N.

According to one embodiment of the invention, detection of a mechanism of resistance to glycopeptides, linked to expression of the protein VanA, is characterized by the detection of at least one peptide belonging to the protein VanA and its different variants of sequences SEQ ID No. 1 to SEQ ID No. 4.

```
SEQ ID No. 1:
MKKPLKTVWILKGDRSMNRIKVAILFGGCSEEHDVSVKSAIEIAANI

NKEKYEPLYIGITKSGVWKMCEKPCAEWENDNCYSAVLSPDKKMHGL

LVKKNHEYEINHVDVAFSALHGKSGEDGSIQGLFELSGIPFVGCDIQ

SSAICMDKSLTYIVAKNAGIATPAFWVINKDDRPVAATFTYPVFVKP

ARSGSSFGVKKVNSADELDYAIESARQYDSKILIEQAVSGCEVGCAV

LGNSAALWGEVDQIRLQYGIFRIHQEVEPEKGSENAVITVPADLSAE

ERGRIQETAKKIYKALGCRGLARVDMFLQDNGRIVLNEVNTLPGFTS

YSRYPRMMAAAGIALPELIDRLIVLALKG

SEQ ID No. 2:
MNRIKVAILFGGCSEEHDVSLKSAIEIAANINKEKYEPLYIGITKSG

VWKMCEKPCAEWENDNCYSAVLSPDKKMHGLLVKKNHEYEINHVDVA

FSALHGKSGEDGSIQGLFELSGIPFVGCDIQSSAICMDKSLTYIVAK
```

-continued

```
NAGIATPAFWVINKDDRPVAATFTYPVFVKPARSGSSFGVKKVNSAD

ELDYAIESARQYDSKILIEQAVSGCEVGCAVLGNSAALVVGEVDQIR

LQYGIFRIHQEVEPEKGSENAVITVPADLSAEERGRIQETAKKIYKA

LGCRGLARVDMFLQDNGRIVLNEVNTLPGFTSYSRYPRMMAAAGIAL

PELIDRLIVLALKG

SEQ ID No. 3:
MNRIKVAILFGGCSEEHDVSVKSAIEIAANINKEKYEPLYIGITKSG

VWKMCEKPCAEWENDNCYSAVLSPDKKMHGLLVKKNHEYEINHVDVA

FSALHGKSGEDGSIQGLFELSGIPFVGCDIQSSAICMDKSLTYIVAK

NAGIATPAFWVINKDDRPVAATFTYPVFVKPARSGSSFGVKKVNSAD

ELDYAIESARQYDSKILIEQAVSGCEVGCAVLGNSAALAVGEVDQIR

TAKKIYKALGCRGLARVDMFLQDNGRIVLNEVNTLPGFTSYSRYPRM

MAAAGIALPELIDRLIVLALKG

SEQ ID No. 4:
MNRIKVAILFGGCSEEHDVSVKSAIEIAANINKEKYEPLYIGITKSG

VWKMCEKPCAEWENDNCYSAVLSPDKKMHGLLVKKNHEYEINHVDVA

FSALHGKSGEDGSIQGLFELSGIPFVGCDIQSSAICMDKSLTYIVAK

NAGIATPAFWVINKDDRPVAATFTYPVFVKPARSGSSFGVKKVNSAD

ELDYAIESARQYDSKILIEQAVSGCEVGCAVLGNSAALVVGEVDQIR

LQYGIFRIHQEVEPEKGSENAVITVPADLSAEERGRIQETAKKIYKA

LGCRGLARVDMFLQDNGRIVLNEVNTLPGFTSYSRYPRMMAAAGIAL

PELIDRLIVLALKG
```

said peptides of type VanA preferably being selected from the peptides of sequence SEQ ID No. 5 to SEQ ID No. 16 as defined below:

| Peptide SEQ ID No. | Amino acid sequence | Position of the peptide in the VanA protein or proteins |
|---|---|---|
| SEQ ID No. 5 | IHQEVEPEK | 243-251 for the proteins of SEQ No. 2, 3, 4; 259-267 for the protein of sequence SEQ ID No. 1 |
| SEQ ID No. 6 | LIVLALK | 336-342 for the proteins of SEQ No. 2, 3, 4; 352-358 for the protein of sequence SEQ ID No. 1 |
| SEQ ID No. 7 | LQYGIFR | 236-242 for the proteins of SEQ No. 2, 3, 4; 252-258 for the protein of sequence SEQ ID No. 1 |
| SEQ ID No. 8 | MHGLLVK | 75-81 for the proteins of SEQ No. 2, 3, 4; 91-97 for the protein of sequence SEQ ID No. 1 |
| SEQ ID No. 9 | MMAAAGIALPELIDR | 321-335 for the proteins of SEQ No. 2, 3, 4; 337-351 for the protein of sequence SEQ ID No. 1 |
| SEQ ID No. 10 | NAGIATPAFWVINK | 142-155 for the proteins of SEQ No. 2, 3, 4; 158-171 for the protein of sequence SEQ ID No. 1 |
| SEQ ID No. 11 | SAIEIAANINK | 23-33 for the proteins of SEQ No. 2, 3, 4; 39-49 for the protein of sequence SEQ ID No. 1 |

-continued

| Peptide SEQ ID No. | Amino acid sequence | Position of the peptide in the VanA protein or proteins |
|---|---|---|
| SEQ ID No. 12 | SGSSFGVK | 175-182 for the proteins of SEQ No. 2, 3, 4; 191-198 for the protein of sequence SEQ ID No. 1 |
| SEQ ID No. 13 | SLTYIVAK | 134-141 for the proteins of SEQ No. 2, 3, 4; 150-157 for the protein of sequence SEQ ID No. 1 |
| SEQ ID No. 14 | VDMFLQDNGR | 291-300 for the proteins of SEQ No. 2, 3, 4; 307-316 for the protein of sequence SEQ ID No. 1 |
| SEQ ID No. 15 | VNSADELDYAIESAR | 184-198 for the proteins of SEQ No. 2, 3, 4; 200-214 for the protein of sequence SEQ ID No. 1 |
| SEQ ID No. 16 | YEPLYIGITK | 36-45 for the proteins of SEQ No. 2, 3, 4; 52-61 for the protein of sequence SEQ ID No. 1 |

Advantageously, the markers of type VanA selected from the peptides of sequence SEQ ID No. 5 to SEQ ID No. 16 are detected after induction of the mechanism of resistance.

Advantageously, the markers of type VanA selected from the peptides of sequence SEQ ID No. 6, SEQ ID No. 7, SEQ ID No. 8, SEQ ID No. 11, SEQ ID No. 12, SEQ ID No. 13, SEQ ID No. 15 and SEQ ID No. 16 are detected without an induction step.

According to another embodiment of the invention, detection of a mechanism of resistance to glycopeptides, linked to expression of the protein VanB, is characterized by the detection of at least one peptide belonging to the protein VanB and its different variants of sequences SEQ ID No. 17 to SEQ ID No. 28.

SEQ ID No. 17:
MNKIKVAIIFGGCSEEHDVSVKSAIEIAANINTEKFDPHYIGITKNGVWKLCKKPCTEW

EADSLPAIFSPDRKTHGLLVMKEREYETRRIDVAFPVLHGKCGEDGAIQGLFELSGIP

YVGCDIQSSAACMDKSLAYILTKNAGIAVPEFQMIEKGDKPEARTLTYPVFVKPARSG

SSFGVTKVNSTEELNAAIEAAGQYDGKILIEQAISGCEVGCAVMGNEDDLIVGEVDQIR

LSHGIFRIHQENEPEKGSENAMIIVPADIPVEERNRVQETAKKVYRVLGCRGLARVD

LFLQEDGGIVLNEVNTLPGFTSYSRYPRMAAAAGITLPALIDSLITLAIER

SEQ ID No. 18:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FELSGIPYVGCDIQSSAACMDKSLAYILTKNAGIAVPEFQMIDKGDKPEAGALTY

PVFVKPARSGSSFGVTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMMAAAGITL

PALIDSLITLALKR

SEQ ID No. 19:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQIIDKGDKPEAGALTYP

VFVKPARSGSSFGVTKVNGTEELNAAIEAAGQYDGKILIEQAISGCEVGCAVMG

NEDDLIVGEVDQIRLSHGIFRIHQENEPEKGSENAMITVPADIPVEERNRVQETA

-continued

KKVYRVLGCRGLARVDLFLQEDGGIVLNEVNTMPGFTSYSRYPRMVAAAGITLP

ALIDSLITLALKR

SEQ ID No. 20:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQIIDKGDKPEAGALTYP

VFVKPARSGSSFGVTKVNGTEELNAAIEAAGQYDGKILIEQAISGCEVGCAVMG

NEDDLIVGEVDQIRLSHGIFRIHQENEPEKGSENAMITVPADIPVEERNRVQETA

KKVYRVLGCRGLARVDLFLQEDGGIVLNEVNTMPGFTSYSRYTRMVAAAGITLP

ALIDSLITLALKR

SEQ ID No. 21:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQMIDKGDKPEAGALTY

PVFVKPARSGSSFGLTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMMAAAGITL

PALIDSLITLALKR

SEQ ID No. 22:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQMIDKGDKPEAGALTY

PVFVKPARSGSSFGVTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMMAAAGITL

PALIDSLITLALKR

SEQ ID No. 23:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAVCMDKSLAYILTKNAGIAVPEFQMIDKGDKPEAGALTY

PVFVKPARSGSSFGVTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMVAAAGITL

PALIDSLITLALKR

SEQ ID No. 24:
MNRIKVAIIFGGCSEEHDVSVKSAIEIAANIDTEKFDPHYIGITKNGVWKLCKKPC

TEWEADSLPAILSPDRKTHGLLVMKESEYETRRIDVAFPVLHGKCGGGEDGAIQ

GLFVLSGIPYVGCDIQSSAACMDKSLAYILTKNAGIAVPEFQMIDKGDKPEAGAL

TYPVFVKPARSGSSFGVTKVNGTEELNAAIEAAGQYDGKILIEQAISGCEVGCAV

MGNEDDLIVGEVDQIRLSHGIFRIHQENEPEKGSENAMITVPADIPVEERNRVQE

TAKKVYRVLGCRGLARVDLFLQEDGGIVLNEVNTLPGFTSYSRYPRMMAAAGIT

LPALIDSLITLALKR

-continued

SEQ ID No. 25:
MNRIKVAIIFGGCSEEHDVSVKSAIEIAANINTEKFDPHYIGITKNGVWKLCKKPC

TEWEADSLPAILSPDRKTHGLLVMKESEYETRRIDVAFPVLHGKCGEDGAIQGL

FELSGIPYVGCDIQSSAACMDKSLAYILTKNAGIAVPEFQMIDKGDKPEAGALTY

PVFVKPARSGSSFGVTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMVAAAGITL

PALIDSLITLALKR

SEQ ID No. 26:
MNRIKVATIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQMIDKGDKPEAGALTY

PVFVKPARAGSSFGLTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMMAAAGITL

PALIDSLITLALKR

SEQ ID No. 27:
MNRIKVATIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQMIDKGDKPEAGALTY

PVFVKPARSGSSFGLTKVNGTEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTLPGFTSYSRYPRMMAAAGITL

PAMIDSLITLALKR

SEQ ID No. 28:
MNRIKVATIFGGCSEEHDVSVKSAIEIAANIDTEKFDPHYIGITKNGVWKLCKKPC

TEWEADSLPAILSPDRKTHGLLVMKESEYETRRIDVAFPVLHGKCGEDGAIQGL

FVLSGIPYVGCDIQSSAACMDKSLAYILTKNAGIAVPEFQMIDKGDKPEAGALTY

PVFVKPARSGSSFGVTKVNGPEELNAAIEAAGQYDGKILIEQAISGCEVGCAVM

GNEDDLIVGEVDQIRLSHGIFRIHQENEPEKGSENAMITVPADIPVEERNRVQET

AKKVYRVLGCRGLARVDLFLQEDGGIVLNEVNTMPGFTSYSRYPRMVAAAGITL

PALIDSLITLALKR said markers of type VanB preferably being selected from the peptides of sequence SEQ ID No. 29 to SEQ ID No. 35 as defined below:

| Peptide SEQ ID No. | Amino acid sequence | Position of the peptide in the VanB protein or proteins |
|---|---|---|
| SEQ ID No. 29 | FDPHYIGITK | 36-45 for the proteins of SEQ No. 17, 18, 19, 20, 21, 22, 23, 24, 25, 26, 27, 28 |
| SEQ ID No. 30 | IDVAFPVLHGK | 90-100 for the proteins of SEQ No. 17, 18, 19, 20, 21, 22, 23, 24, 25, 26, 27, 28 |

-continued

| Peptide SEQ ID No. | Amino acid sequence | Position of the peptide in the VanB protein or proteins |
|---|---|---|
| SEQ ID No. 31 | IHQENEPEK | 242-250 for the proteins of SEQ No. 17, 18, 19, 20, 21, 22, 23, 25, 26, 27, 28; 244-252 for the protein of sequence SEQ ID No. 24 |
| SEQ ID No. 32 | LSHGIFR | 235-241 for the proteins of SEQ No. 17, 18, 19, 20, 21, 22, 23, 25, 26, 27, 28; 237-243 for the protein of sequence SEQ ID No. 24 |
| SEQ ID No. 33 | SLAYILTK | 133-140 for the proteins of SEQ No. 17, 18, 19, 20, 21, 22, 23, 25, 26, 27, 28; 135-142 for the protein of sequence SEQ ID No. 24 |
| SEQ ID No. 34 | THGLLVMK | 74-81 for the proteins of SEQ No. 17, 18, 19, 20, 21, 22, 23, 24, 25, 26, 27, 28 |
| SEQ ID No. 35 | VQETAK | 271-276 for the proteins of SEQ No. 17, 18, 19, 20, 21, 22, 23, 25, 26, 27, 28; 273-278 for the protein of sequence SEQ ID No. 24 |

Advantageously, the markers of type VanB selected from the peptides of sequence SEQ ID No. 29, SEQ ID No. 30, SEQ ID No. 32 and SEQ ID No. 33 are detected after induction of the mechanism of resistance.

According to another embodiment of the invention, detection of a mechanism of resistance to glycopeptides, linked to expression of the protein VanC, is characterized by the detection of at least one peptide belonging to the protein VanC and its different variants of sequences SEQ ID No. 36 to SEQ ID No. 58. Notably the variants VanC1 are characterized by the detection of at least one peptide belonging to the protein VanC1 and its different variants of sequences SEQ ID No. 36 to SEQ ID No. 43, the variants VanC2 or VanC3 are characterized by the detection of at least one peptide belonging to the protein VanC2 or Van C3 and its different variants of sequences SEQ ID No. 46 to SEQ ID No. 51 and SEQ ID No. 53 to SEQ ID No. 57, the variants VanC4 are characterized by the detection of at least one peptide belonging to the protein VanC4 and its different variants of sequences SEQ ID No. 44, SEQ ID No. 45, SEQ ID No. 52 and SEQ ID No. 58

SEQ ID No. 36:
MKKIAVLFGGNSPEYSVSLASAASVIQAIDPLKYEVMTIGIAPTMDWYLYQGNLANVRND

TWLEDHKNCHQLTFSSQGFILGEKRIVPDVLFPVLHGKYGEDGCIQGLLELMNLPYVGCH

VAASALCMNKWLLHQLADTMGIASAPTLLLSRYENDPATIDRFIQDHGFPIFIKPNEA

GSSKGITKVTDKTALQSALTTAFAYGSTVLIQKAIAGIEIGCGILGNEQLTIGACDA

ISLVDGFFDFEEKYQLISATITVPAPLPLALESQIKEQAQLLYRNLGLTGLARIDF

FVTNQGAIYLNEINTMPGFTGHSRYPAMMAEVGLSYEILVEQLIALAEEDKR

SEQ ID No. 37:
MKKIAVLFGGNSPEYSVSLASAASVIQAIDPLKYEVMTIGIAPTMDWYWYQGNL

ANVRNDTWLEDHKNCHQLTFSSQGFILGEKRIVPDVLFPVLHGKYGEDGCIQGL

LELMNLPYVGCHVAASALCMNKWLLHQLADTMGIASAPTLLLSRYENDPATIDR

FIQDHGFPIFIKPNEAGSSKGITKVTDKTALQSALTTAFAYGSTVLIQKAIAGIEIGC

GILGNEQLTIGACDAISLVDGFFDFEEKYQLISATITVPAPLPLALESQIKEQAQLL

YRNLGLTGLARIDFFVTNQGAIYLNEINTMPGFTGHSRYPAMMAEVGLSYEILVE

QLIALAEEDKR

SEQ ID No. 38:
MKKIAVLFGGNSPEYSVSLASAASVIQAIDPLKYEVMTIGIAPTMDWYWYQGNL

ANVRNDTWLEDHKNCHQLTFSSQGFILGEKRIVPDVLFPVLHGKYGEDGCIQGL

LELMNLPYVGCHVAATALCMNKWLLHQLADTMGIASAPTLLLSRYENDPATIDR

-continued

FIQDHGFPIFIKPNEAGSSKGITKVTDKTALQSALTTAFAYGSTVLIQKAIAGIEIGC

GILGNEQLTIGACDAISLVDGFFDFEEKYQLISATITVPAPLPLALESQIKEQAQLL

YRNLGLTGLARIDFFVTNQGAIYLNEINTMPGFTGHSRYPAMMAEVGLSYEILVE

QLIALAEEDKR

SEQ ID No. 39:
MKKIAVLFGGNSPEYSVSLTSAASVIQAIDPLKYEVMTIGIAPTMDWYWYQGNLA

NVRNDTWLEDHKNCHQLTFSSQGFILGEKRIVPDVLFPVLHGKYGEDGCIQGLL

ELMNLPYVGCHVAASALCMNKWLLHQLADTMGIASAPTLLLSRYENDPATIDRF

IQDHGFPIFIKPNEAGSSKGITKVTDKTALQSALTTAFAYGSTVLIQKAIAGIEIGC

GILGNEQLTIGACDAISLVDGFFDFEEKYQLISATITVPAPLPLALESQIKEQAQLL

YRNLGLTGLARIDFFVTNQGAIYLNEINTMPGFTGHSRYPAMMAEVGLSYEILVE

QLIALAEEDKR

SEQ ID No. 40:
MKKIAVLFGGNSPEYSVSLTSAASVIQAIDPLKYEVMTIGIAPTMDWYWYQGNLA

NVRNDTWLEDHKNCHQLTFSSQGFILGEKRIVPDVLFPVLHGKYGEDGCIQGLL

ELMNLPYVGCHVAASALCMNKWLLHQLADTMGIASAPTLLLSRYENDPATIDRF

IQDHGFPIFIKPNEAGSSKGITKVTDKTALQSALTTAFAYGSTVLIQKAIAGIEIGC

GILGNEQLTIGACDAISLVDGFFDFEEKYQLISATITVPAPLPLALESQIKEQAQLL

YRNLGLTGLARIDFFVTNQGAIYLNEINTMPGFTGHSRYPAMMAEVGLSYEILVE

KLIALAEEDKR

SEQ ID No. 41:
MKKIAVLFGGNSPEYSVSLTSAESVIQAINPLKYEVMTIGIAPTMDWYWYQGNLA

NVRNDTWLEDHKNCHQLTFSSQGFILGEKRIVPDVLFPVLHGKYGEDGCIQGLL

ELMNLPYVGCHVAASALCMNKWLLHQLADTMGIASAPTLLLSRYENDPATIDRF

IQDHGFPIFIKPNEAGSSKGITKVTDKTALQSALTTAFAYGSTVLIQKAIAGIEIGC

GILGNEQLTIGACDAISLVDGFFDFEEKYQLISATITVPAPLPLALESQIKEQAQLL

YRNLGLTGLARIDFFVTNQGAIYLNEINTMPGFTGHSRYPAMMAEVGLSYEILVE

QLIALAEEDKR

SEQ ID No. 42:
MMKKIAVLFGGNSPEYSVSLASAASVIQAIDPLKYEVMTIGIAPTMDWYWYQGN

LANVRNDTWLEDHKNCHQLTFSSQGFILGEKRIVPDVLFPVLHGKYGEDGCIQG

LLELMNLPYVGCHVAASALCMNKWLLHQLADTMGIASAPTLLLSRYENDPATID

RFIQDHGFPIFIKPNEAGSSKGITKVTDKTALQSALTTAFAYGSTVLIQKAIAGIEIG

CGILGNEQLTIGACDAISLVDGFFDFEEKYQLISATITVPAPLPLALESQIKEQAQL

LYRNLGLTGLARIDFFVTNQGAIYLNEINTMPGFTGHSRYPAMMAEVGLSYEILV

EQLIALAEEDKR

-continued

SEQ ID No. 43:
MMKKIAVLFGGNSPEYSVSLTSAASVIQAIDPLKYEVMTIGIAPTMDWYWYQGN

LANVRNDTWLEDHKNCHQLTFSSQGFILGEKRIVPDVLFPVLHGKYGEDGCIQG

LLELMNLPYVGCHVAASALCMNKWLLHQLADTMGIASAPTLLLSRYENDPATID

RFIQDHGFPIFIKPNEAGSSKGITKVTDKTALQSALTTAFAYGSTVLIQKAIAGIEIG

CGILGNEQLTIGACDAISLVDGFFDFEEKYQLISATITVPAPLPLALESQIKEQAQL

LYRNLGLTGLARIDFFVTNQGAIYLNEINTMPGFTGHSRYPAMMAEVGLSYEILV

EQLIALAEEDKR

SEQ ID No. 44:
MKKIAIIFGGNSPEYAVSLASATSAIEALQSSPDDYDLSLIGIAPDAMDWYLYTGE

LENIRQDTWLLDTKHKQKIQPLFEGNGFWLSEAQQTLVPDVLFPIMHGKYGED

GSIQGLFELMKLPYVGCGVAASALCMNKWLLHQAAAAIGVQSAPTILLTNQANQ

QDQIEAFIQTHGFPVFFKPNEAGSSKGITKVTCVEEIASALKEAFTYCSAVLLQK

NIAGVEIGCGILGNDSLTVGACDAISLVDGFFDFEEKYQLISAKITVPAPLPETIET

KVKEQAQLLYHSLGLKGLARIDFFVTDQGELYLNEINTMPGFTSHSRYPAMMAA

IGLSYQELLQKLLVLAKEEVK

SEQ ID No. 45:
MKKIAIIFGGNSPEYAVSLASATSAIEALQSSPYDYDLSLIGIAPDAMDWYLYTGE

LENIRQDTWLLDTKHKQKIQPLFEGNGFWLSEEQQTLVPDVLFPIMHGKYGED

GSIQGLFELMKLPYVGCGVAASALCMNKWLLHQAAEAIGVQSAPTILLTNQDNQ

QRQIEAFIQTHDFPVFFKPNEAGSSKGITKVTCVEEIAPALKEAFAYCSAVLLQK

NIAGVEIGCGILGNDSLTVGACDAISLVEGFFDFEEKYQLISAKITVPAPLPETIET

KVKEQAQLLYHSLGLKGLARIDFFVTDQGELYLNEINTMPGFTSHSRYPAMMAA

IGLSYQELLQKLLVLAKEEGK

SEQ ID No. 46:
MKKIAIIFGGNSPEYAVSLASATSALEALQSSPYDYDLSLIGIAPDAMDWYLYTGE

LENIRQDTWLLDTKHKQKIQPLFEGNGFWLSEEQQTLVPDVLFPIMHGKYGED

GSIQGLFELMKLPYVGCGVAGSALCMNKWLLHQAAAAIGVQSAPTILLTNQANQ

QEQIEAFIQTHGFPVFFKPNEAGSSKGITKVTCVEEIASALKEAFTYCSAVLLQKN

IAGVEIGCGILGNDSLTVGACDAISLVDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLVLAKEEVK

SEQ ID No. 47:
MKKIAIIFGGNSPEYTVSLASATSAIEALQSSPYDYDLSLIGIAPDAMDWYLYTGE

LENIRQDTWLLDTKHKQKIQPLFEGNGFWLSEEQQTLVPDVLFPIMHGKYGED

GSIQGLFELMKLPYVGCGVAGSALCMNKWLLHQAAAAIGVQSAPTILLTNQANQ

QEQIEAFIQTHGFPVFFKPNEAGSSKGITKVTCVEEIASALKEAFTYCSAVLLQKN

IAGVEIGCGILGNDSLTVGACDAISLVDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLVLAKEEVK

-continued

SEQ ID No. 48:
MKKIAIIFGGNSPEYTVSLASATSAIEALQSSPYDYDLSLIGIAPDAMDWYLYTGE

LENIRQDTWLLDTKHKQKIQPLFEGNGFWLSEEQQTLVPDVLFPIMHGKYGED

GSIQGLFELMKLPYVGCGVAGSALCMNKWLLHQAAAAIGVQSAPTILLTNQANQ

QEQIEAFIQTHGFPVFFKPNEAGSSKGITKVTCVEEIASALKEAFTYCSAVLLQKN

IAGVEIGCGILGNDSLTVGACDAISLVDGFFDFEEKYQLISAKITVPAPLPETIETK

VKEQAQLLYRSLGLKGLARIDFFVTERGELYLNEINTMPGFTSHSRYPAMMAAV

GLSYQELLQKLLVLAKEEVK

SEQ ID No. 49:
MKKIAIIFGGNSPEYTVSLASATSAIEALQSSPYDYDLSLIGIAPDAMDWYLYTGE

LENIRQDTWLLDTKHKQKIQPLFEGNGFWLSEEQQTLVPDVLFPIMHGKYGED

GSIQGLFELMKLPYVGCGVAGSALCMNKWLLHQAAAAIGVQSAPTILLTNQANQ

QEQIEAFIQTHGFPVFFKPNEAGSSKGITKVTCVEEIASALKEAFTYCSAVLLQKN

IVGVEIGCGILGNDSLTVGACDAISLVDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLVLAKEEVK

SEQ ID No. 50:
MKKIAIIFGGNSPEYTVSLASATSAIEALQSSPYDYDLSLIGIAPDAMDWYLYTGE

LENIRQDTWLLDTKHKQKIQPLFEGNGFWLSEEQQTLVPDVLFPIMHGKYGED

GSIQGLFELMKLPYVGCGVASSALCMNKWLLHQAAAAIGVQSAPTILLTNQANQ

QEQIEAFIQTHGFPVFFKPNEAGSSKGITKVTCVEEIASALKEAFTYCSAVLLQKN

IVGVEIGCGILGNDSLTVGACDAISLEDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLILAKEEVK

SEQ ID No. 51:
MKKIAIIFGGNSPEYTVSLASATSAIEALQSSPYDYDLSLIGIAPDAMDWYLYTGE

LENIRQDTWLLDTKHTQKIKPLFEGNGFWLSEEQQTLVPDVLFPIMHGKYGEDG

SIQGLFELMKLPYVGCGVAGSALCMNKWLLHQAAAAIGVQSAPTILLTNQANQQ

EQIEAFIQTHGFPVFFKPNEAGSSKGITKVTCVEEIASALKEAFTYCSAVLLQKNI

AGVEIGCGILGNDSLTVGACDAISLVDGFFDFEEKYQLISAKITVPAPLPETIETKV

KEQAQLLYRSLGLKGLARIDFFVTDQGELYLNEINTMPGFTSHSRYPAMMAAVG

LSYQELLQKLLVLAKEEVK

SEQ ID No. 52:
MKKIAIIFGGNSPEYTVSLASATSAIEALQSSPYDYDLSLIGIAPDAMDWYLYTGE

LENIRQDTWLLDTKHTQKIQPLFEGNGFWISEAQQTLVPDVLFPIMHGKYGEDG

SIQGMFELMKLPYVGCGVAASALCMNKWLLHQAAAAIGVQSAPTILLTNQANQ

QRQIEAFIQTHGFPVFFKPNEAGSSKGITKVTCVEEIAPALKEAFAYCSAVLLQK

NIAGVEIGCGILGNDSLTVGACDAISLVDGFFDFEEKYQLISAKITVPAPLPETIET

KVKEQAQLLYHSLGLKGLARIDFFVTDQGELYLNEINTMPGFTSHSRYPAMMAA

VGLSYQELLQKLLVLAKEEGK

-continued

SEQ ID No. 53:
MKKIAIIFGGNSPEYTVSLASATSAIEALQSSPYDYDLSLIGIAPDAMDWYLYTGE

LENIRQDTWLLDTKQKQKIQPLFEGNGFWLSEEQQTLVPDVLFPIMHGKYGED

GSIQGLFELMKLPYVGCGVAGSALCMNKWLLHQAAAAIGVQSAPTILLTNHANQ

QEQIEAFIQTHGFPVFFKPNEAGSSKGITKVTCVEEIASALKEAFTYCSAVLLQKN

IAGVEIGCGILGNDSLTVGACDAISLVDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLVLAKEEVK

SEQ ID No. 54:
MKKIAIIFGGNSPEYTVSLASATSAIEALQSSPYDYDLSLIGIAPDAMDWYLYTGE

LENIRQDTWLLDTKQKQKIQPLFEGNGFWLSEEQQTLVPDVLFPIMHGKYGED

GSIQGLFELMKLPYVGCGVASSALCMNKWLLHQAAAAIGVQSAPTILLTNQANQ

QEQIEAFIQTHGFPVFFKPNEAGSSKGITKVTCVEEIASALKEAFTYCSAVLLQKN

IVGVEIGCGILGNDSLTVGACDAISLEDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLILAKEEVK

SEQ ID No. 55:
MKKIAIIFGGNSPEYTVSLASATSAIEALQSSPYDYDLSLIGIAPDAMDWYLYTGE

LENIRQDTWLLDTKQKQKIQPLFEGNGFWLSEEQQTLVPDVLFPIMHGKYGED

GSIQGMFELMKLPYVGCGVAGSALCMNKWLLHQAAAAIGVQSAPTILLTNHAN

QQEQIEAFIQTHGFPVFFKPNEAGSSKGITKVTCVEEIASALKEAFTYCSAVLLQ

KNIAGVEIGCGILGNDSLTVGACDAISLVDGFFDFEEKYQLISAKITVPAPLPETIE

TKVKEQAQLLYRSLGLKGLARIDFFVTDQGELYLNEINTMPGFTSHSRYPAMMA

AVGLSYQELLQKLLVLAKEEVK

SEQ ID No. 56:
MKKIAIIFGGNSPEYTVSLASATSAIEALQSSPYDYDLSLIGITPDAMDWYLYTGE

LENIRQDTWLLDTKHKQKIQPLFEGNGFWLSEEQQTLVPDVLFPIMHGKYGED

GSIQGLFELMKLPYVGCGVAGSALCMNKWLLHQAAAAIGVQSAPTILLTNQANQ

QEQIEAFIQTHGFPVFFKPNEAGSSKGITKVTCVEEIASALKEAFTYCSAVLLQKN

IAGVEIGCGILGNDSLTVGACDAISLVDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLVLAKEEVK

SEQ ID No. 57:
MKKIAIIFGGNSPEYTVSLASATSAIEALQSSPYDYDLSLIGITPDAMDWYLYTGE

LENIRQDTWLLDTKHKQKIQPLFEGNGFWLSEEQQTLVPDVLFPIMHGKYGED

GSIQGLFELMKLPYVGCGVAGSALCMNKWLLHQAAAAIGVQSAPTILLTNQANQ

QEQIEAFIQTHGFPVFFKPNEAGSSKGITKVTCVEEIASALKEAFTYCSAVLLQKN

IVGVEIGCGILGNDSLTVGACDTISLVDGFFDFEEKYQLISAKITVPAPLPETIETK

VKEQAQLLYRSLGLKGLARIDFFVTDQGELYLNEINTMPGFTSHSRYPAMMAAV

GLSYQELLQKLLVLAKEEVK

-continued

SEQ ID No. 58:
MKKIAIIFGGNSSEYTVSLASATSAIEALQSSPYDYDLSLIGIAPDAMDWYLYTGE

LENIRQDTWLLDTKHTQKIQPLFEENGFWLSEAQQTLVPDVLFPIMHGKYGEDG

SIQGLFELMKLPYVGCGVAASALCMNKWLLHQAAAAIGVQSAPTILLTNQDNQQ

QQIEAFIQTHGFPVFFKPNEAGSSKGITKVTCVEEIAPALKEAFAYCSAVLLQKNI

AGVEIGCGILGNDSLTVGACDAISLVEGFFDFEEKYQLISAKITVPAPLPETIETKV

KEQAQLLYHSLGLKGLARIDFFVTDQGELYLNEINTMPGFTSHSRYPAMMAAIG

LSYQELLQKLLVLAKEEGK said markers of type VanC preferably being selected from the peptides of sequence SEQ ID No. 59 to SEQ ID No. 71 as defined below:

| Peptide SEQ ID No | Amino acid sequence | Position of the peptide in the VanC protein or proteins |
|---|---|---|
| SEQ ID No. 59 | EQAQLLYR | 279-286 for the proteins of SEQ No. 46, 47, 48, 49, 50, 51, 53, 54, 55, 56, 57; 272-279 for the protein of sequence SEQ ID No. 36; 272-279 for the protein of sequence SEQ ID No. 37; 272-279 for the protein of sequence SEQ ID No. 38; 272-279 for the protein of sequence SEQ ID No. 39; 272-279 for the protein of sequence SEQ ID No. 40; 272-279 for the protein of sequence SEQ ID No. 41; 273-280 for the protein of sequence SEQ ID No. 42; 273-280 for the protein of sequence SEQ ID No. 43 |
| SEQ ID No. 60 | FIQDHGFPIFIKPN EAGSSK | 164-183 for the proteins of SEQ No. 42, 43; 163-182 for the protein of sequence SEQ ID No. 36; 163-182 for the protein of sequence SEQ ID No. 37; 163-182 for the protein of sequence SEQ ID No. 38; 163-182 for the protein of sequence SEQ ID No. 39; 163-182 for the protein of sequence SEQ ID No. 40; 163-182 for the protein of sequence SEQ ID No. 41 |
| SEQ ID No. 61 | IVPDVLFPVLHG K | 87-99 for the proteins of SEQ No. 42, 43; 86-98 for the protein of sequence SEQ ID No. 36; 86-98 for the protein of sequence SEQ ID No. 37; 86-98 for the protein of sequence SEQ ID No. 38; 86-98 for the protein of sequence SEQ ID No. 39; 86-98 for the protein of sequence SEQ ID No. 40; 86-98 for the protein of sequence SEQ ID No. 41 |
| SEQ ID No. 62 | NCHQLTFSSQGFI LGEK | 69-85 for the proteins of SEQ No. 42, 43; 68-84 for the protein of sequence SEQ ID No. 36; 68-84 for the protein of sequence SEQ ID No. 37; 68-84 for the protein of sequence SEQ ID No. 38; 68-84 for the protein of sequence SEQ ID No. 39; 68-84 for the protein of sequence SEQ ID No. 40; 68-84 for the protein of sequence SEQ ID No. 41 |
| SEQ ID No. 63 | NDTWLEDHK | 60-68 for the proteins of SEQ No. 42, 43; 59-67 for the protein of sequence SEQ ID No. 36; 59-67 for the protein of sequence SEQ ID No. 37; 59-67 for the protein of sequence SEQ ID No. 38; 59-67 for the protein of sequence SEQ ID No. 39; 59-67 for the protein of sequence SEQ ID No. 40; 59-67 for the protein of sequence SEQ ID No. 41 |
| SEQ ID No. 64 | NLGLTGLAR | 281-289 for the proteins of SEQ No. 42, 43; 280-288 for the protein of sequence SEQ ID No. 36; 280-288 for the protein of sequence SEQ ID No. 37; 280-288 for the protein of sequence SEQ ID No. 38; 280-288 for the protein of sequence SEQ ID No. 39; 280-288 |

-continued

| Peptide SEQ ID No | Amino acid sequence | Position of the peptide in the VanC protein or proteins |
|---|---|---|
| | | for the protein of sequence SEQ ID No. 40; 280-288 for the protein of sequence SEQ ID No. 41 |
| SEQ ID No. 65 | TALQSALTTAFA YGSTVLIQK | 192-212 for the proteins of SEQ No. 42, 43; 191-211 for the protein of sequence SEQ ID No. 36; 191-211 for the protein of sequence SEQ ID No. 37; 191-211 for the protein of sequence SEQ ID No. 38; 191-211 for the protein of sequence SEQ ID No. 39; 191-211 for the protein of sequence SEQ ID No. 40; 191-211 for the protein of sequence SEQ ID No. 41 |
| SEQ ID No. 66 | WLLHQLADTMG IASAPTLLLSR | 132-153 for the proteins of SEQ No. 42, 43; 131-152 for the protein of sequence SEQ ID No. 36; 131-152 for the protein of sequence SEQ ID No. 37; 131-152 for the protein of sequence SEQ ID No. 38; 131-152 for the protein of sequence SEQ ID No. 39; 131-152 for the protein of sequence SEQ ID No. 40; 131-152 for the protein of sequence SEQ ID No. 41 |
| SEQ ID No. 67 | YENDPATIDR | 154-163 for the proteins of SEQ No. 42, 43; 153-162 for the protein of sequence SEQ ID No. 36; 153-162 for the protein of sequence SEQ ID No. 37; 153-162 for the protein of sequence SEQ ID No. 38; 153-162 for the protein of sequence SEQ ID No. 39; 153-162 for the protein of sequence SEQ ID No. 40; 153-162 for the protein of sequence SEQ ID No. 41 |
| SEQ ID No. 68 | YQLISATITVPAP LPLALESQIK | 250-272 for the proteins of SEQ No. 42, 43; 249-271 for the protein of sequence SEQ ID No. 36; 249-271 for the protein of sequence SEQ ID No. 37; 249-271 for the protein of sequence SEQ ID No. 38; 249-271 for the protein of sequence SEQ ID No. 39; 249-271 for the protein of sequence SEQ ID No. 40; 249-271 for the protein of sequence SEQ ID No. 41 |
| SEQ ID No. 69 | ITVPAPLPETIET K | 263-276 for the proteins of SEQ No. 44, 45, 46, 47, 48, 49, 50, 51, 52, 53, 54, 55, 56, 57, 58 |
| SEQ ID No. 70 | QDTWLLDTK | 62-70 for the proteins of SEQ No. 44, 45, 46, 47, 48, 49, 50, 51, 52, 53, 54, 55, 56, 57, 58 |
| SEQ ID No. 71 | YQLISAK | 256-262 for the proteins of SEQ No. 44, 45, 46, 47, 48, 49, 50, 51, 52, 53, 54, 55, 56, 57, 58 |

According to another embodiment of the invention, detection of a mechanism of resistance to glycopeptides, linked to expression of the protein VanD, is characterized by the detection of at least one peptide belonging to the protein VanD and its different variants of sequences SEQ ID No. 72 to SEQ ID No. 79.

SEQ ID No. 72:
MFKIKVAVLFGGCSEEHNVSIKSAMEIAANIDTKKYQPYYIGITKSGVWK

MCEKPCLEWEQYAGDPVVFSPDRSTHGLLIQKDKGYEIQPVDVVLPMIHG

KFGEDGSIQGLLELSGIPYVGCDIQSSVTCMDKALAYTVVKNAGIAVPGF

RILQEGDRLETEDFVYPVFVKPARSGSSFGVNKVCKAEELQAAIEEARKY

DSKILIEEAVTGSEVGCAILGNGNDLMAGEVDQIELRHGFFKIHQEAQPE

KGSENAVIRVPAALPDEVRERIQKTAMKIYRILGCRGLARIDLFLREDGC

IVLNEVNTMPGFTSYSRYPRMMTAAGFTLTEILDRLIELSLRR

SEQ ID No. 73:
MFKIKVAVLFGGCSEEHNVSIKSAMEIAANIDTKKYQPYYIGITKSGVWK

MCEKPCLGWEQYAGDPVVFSPDRSTHGLLIQKDTGYEIQPVDVVFPMIHG

-continued

KFGEDGSIQGLLELSGIPYVGCDIQSSVICMDKALAYTVVKNAGIAVPGF

RILQEGDRLETEDLVYPVFVKPARSGSSFGVNKVCKAEELQAAIREARKY

DSKILIEEAVTGSEVGCAILGNENDLMAGEVDQIELRHGFFKIHQEAQPE

KGSENAVIRVPAALPDEVRERIRKTAMKIYRILGCRGLARIDLFLREDGC

IVLNEVNTMPGFTSYSRYPRMMTAAGFTLSEILDRLIEFSLRR

SEQ ID No. 74:
MFRIKVAVLFGGCSEEHNVSIKSAMEIAANIDTKKYQPYYIGITKSGVWK

MCEKPCLEWEQYAGDPVVFSPDRSTHGLLIQKDKGYEIQPVDVVFPMIHG

KFGEDGSIQGLLELSGIPYVGCDIQSSVICMDKALAYTVVKNAGITVPGF

RILQEGDRLETEDFVYPVFVKPARSGSSFGVNKVCKAEELQAAIEEARKY

DSKILIEEAVTGSEVGCAILGNGNDLMAGEVDQIELRHGFFKIHQEAQPE

KGSENAVIRVPAALPDEVREQIQETAMKIYRILGCRGLARIDLFLREDGC

IVLNEVNTMPGFTSYSRYPRMMTAAGFTLSEILDRLIELSLRR

-continued

SEQ ID No. 75:
MFRIKVAVLFGGCSEEHNVSIKSAMEIAANIDTKKYQPYYIGITKSGVWK

MCEKPCLEWEQYAGDPVVFSPDRSTHGLLIQKDTGYEIQPVDVGLPMIHG

KFGEDGSIQGLLELSGIPYVGCDIQSSVTCMDKALAYTVVKNAGIAVPGF

RILQEGDRLETEDFVYPVFVKPARSGSSFGVNKVCKAEELQAAIEDARKY

DSKILIEEAVTGSEVGCAILGNGNDLMAGEVDQIELRHGFFKIHQEAQPE

KGSENAVIRVPAALPDEVIERIQKTAMKIYRILGCRGLARIDLFLREDGC

IVLNEVNTMPGFTSYSRYPRMMTAAGFTLTEILDRLIELSLRR

SEQ ID No. 76:
MYKLKIAVLFGGCSEEHDVSVKSAMEVAANINKEKYQPFYIGITKSGAWK

LCDKPCRDWENYAGYPAVISPDRRIHGLLIQKDGGYESQPVDVVLPMIHG

KFGEDGTIQGLLELSGIPYVGCDIQSSVICMDKSLAYMVVKNAGIEVPGF

RVLQKGDSLEAETLSYPVFVKPARSGSSFGVNKVCRAEELQAAVTEAGKY

-continued

DSKILVEEAVSGSEVGCAILGNGNDLITGEVDQIELKHGFFKIHQEAQPE

KGSENAVIRVPAALPDEVREQIQETAKKIYRVLGCRGLARIDLFLREDGS

IVLNEVNTMPGFTSYSRYPRMMTAAGFTLSEILDRLIGLSLRR

SEQ ID No. 77:
MYKLKIAVLFGGCSEEHDVSVKSAMEVAANINKEKYQPFYIGITKSGAWK

LCDKPCRDWENYAGYPAVISPDRRIHGLLIQKDGGYESQPVDVVLPMIHG

KFGEDGTIQGLLELSGIPYVVCDIQSSVICMDKSLAYMVVKNAGIEVPGF

RVLQKGDSLEAETLSYPVFVKPARSGSSFGVNKVCRAEELQAAVTEAGKY

DSKILVEEAVSGSEVGCAILGNGNDLITGEVDQIELKHGFFKIHQEAQPE

KGSENAVIRVPAALPDEVREQIQETAKKIYRVLGCRGLARIDLFLREDGS

IVLNEVNTMPGFTSYSRYPRMMTAAGFTLSEILDRLIGLSLRR

SEQ ID No. 78:
MYKLKIAVLFGGCSEEHDVSVKSAMEVAANINKEKYQPFYIGITKSGAWK

LCDKPCRDWENYAGYPAVISPDRRTHGLLIQKDGGYESQPVDVVLPMIHG

KFGEDGTIQGLLELSGIPYVGCDIQSSVTCMDKSLAYMVVKNAGIEVPGF

RVLQKGDSLKAETLSYPVFVKPARSGSSFGVNKVCRAEELQAAVTEAGKY

DCKILVEEAVSGSEVGCAILGNENALMAGEVDQIELRHGFFKIHQEAQPE

-continued

KGSENAVIRVPAVLPDEVRERIQKTAMKIYRILGCRGLARIDLFLREDGC

IVLNEVNTMPGFTSYSRYPRMMTAAGFTLTEILDRLIELSLRR

SEQ ID No. 79:
MYRINVAVLFGGCSEEHTVSIKSAMELAANIDTEKYQPFYIGITKSGVWK

LCEKPCLDWEQYAKYPVVFSPGRNTHGFLIQKEDRYEIQPVDVVFPIIHG

KFGEDGSIQGLLELSGIPYVGCDIQSSVICMDKSLAYTTVKNAGIEVPDF

QIIQDGDSPKTECFSFPLFVKPARSGSSFGVNKVDKAEDLCAAINEARQY

DRKVLIEQAVSGSEVGCAVLGTGTDLIVGEVDQISLKHGFFKIHQEAQPE

KGSENATIEVPADLPAKVRERIQKTAKKIYQVLGCRGLARIDLFLREDGH

IVLNEVNTMPGFTSYSRYPCMMTAAGFTLSELIDRLIELALRR said peptides of type VanD preferably being selected from the peptides of sequence SEQ ID No. 80 to SEQ ID No. 83 as defined below:

| Peptide SEQ ID No. | Amino acid sequence | Position of the peptide in the VanD protein or proteins |
|---|---|---|
| SEQ ID No. 80 | GSENAVIR | 252-259 for the proteins of SEQ No. 72, 73, 74, 75, 76, 77, 78 |
| SEQ ID No. 81 | IDLFLR | 291-296 for the proteins of SEQ No. 72, 73, 74, 75, 76, 77, 78, 79 |
| SEQ ID No. 82 | IHQEAQPEK | 243-251 for the proteins of SEQ No. 72, 73, 74, 75, 76, 77, 78, 79 |
| SEQ ID No. 83 | SGSSFGVNK | 175-183 for the proteins of SEQ No. 72, 73, 74, 75, 76, 77, 78, 79 |

Advantageously, the markers of type VanD selected from the peptides of sequence SEQ ID No. 80, SEQ ID No. 81 and SEQ ID No. 83 are detected after induction of the mechanism of resistance.

Advantageously, the markers of type VanD selected from the peptides of sequence SEQ ID No. 80, SEQ ID No. 81 and SEQ ID No. 83 are detected without an induction step.

According to another embodiment of the invention, detection of a mechanism of resistance to glycopeptides, induced by expression of the protein VanE, is characterized by the detection of at least one peptide belonging to the protein VanE of sequence SEQ ID No. 84.

SEQ ID No. 84:
MKTVAIIFGGVSSEYEVSLKSAVAIIKNMESIDYNVMKIGITEEGHWYLF

EGTTDKIKKDRWFLDESCEEIVVDFAKKSFVLKNSKKIIKPDILFPVLHG

GYGENGAMQGVFELLDIPYVGCGIGAAAISMNKIMLHQFAEAIGVKSTPS

MIIEKGQDLQKVDAFAKIHGFPLYIKPNEAGSSKGISKVERKSDLYKAID

EASKYDSRILIQKEVKGVEIGCGILGNEQLVVGECDQISLVDGFFDYEEK

YNLVTAEILLPAKLSIDKKEDIQMKAKKLYRLLGCKGLARIDFFLTDDGE

ILLNEINTMPGFTEHSRFPMMMNEIGMDYKEIIENLLVLAVENHEKKLST

ID said markers of type VanE preferably being selected from the peptides of sequence SEQ ID No. 85 to SEQ ID No. 91 as defined below:

| Peptide SEQ ID No. | Amino acid sequence | Position of the peptide in the VanE protein or proteins |
|---|---|---|
| SEQ ID No. 85 | AIDEASK | 198-204 for the protein of SEQ No. 84 |
| SEQ ID No. 86 | FPMMMNEIGMDYK | 318-330 for the protein of SEQ No. 84 |
| SEQ ID No. 87 | IMLHQFAEAIGVK | 134-146 for the protein of SEQ No. 84 |
| SEQ ID No. 88 | NMESIDYNVMK | 28-38 for the protein of SEQ No. 84 |
| SEQ ID No. 89 | SAVAIIK | 21-27 for the protein of SEQ No. 84 |
| SEQ ID No. 90 | STPSMIIEK | 147-155 for the protein of SEQ No. 84 |
| SEQ ID No. 91 | YNLVTAEILLPAK | 251-263 for the protein of SEQ No. 84 |

Advantageously, the marker of type VanE corresponding to the peptide of sequence SEQ ID No. 89 is detected after induction of the mechanism of resistance.

According to another embodiment of the invention, detection of a mechanism of resistance to glycopeptides, linked to expression of the protein VanG, is characterized by the detection of at least one peptide belonging to the protein VanG and its different variants of sequences SEQ ID No. 92 to SEQ ID No. 94.

SEQ ID No. 92:
MIKKRIAIIFGGNSTEYEVSLQSASAVFENINTKKFDIVPIGITRNGDWY

HYTGKKEKIANNTWFEDNENLYSVAVSQNRSVKGFIEFKEEKFYIIKVDL

IFPVLHGKNGEDGTLQGLFELAGIPVVGCDTLSSALCMDKDKAHKLVSLA

GISVPKSVTFKFSGKKAALKKIEKELSYPLFVKPVRAGSSFGITKVTKQQ

ELENAIQLAFEHDAEVIVEETINGFEVGCAVLGIDELIVGRVDEIELSSG

FFDYTEKYTLKSSKIYMPARIDAEAEKRIQETAVTIYKALGCSGFSRVDM

FYTPSGEIVFNEVNTIPGFTSHSRYPNMMKGIGLSFAQMLDKLIGLYVE

SEQ ID No. 93:
MQNKKIAVIFGGNSTEYEVSLQSASAVFENINTNKFDIIPIGITRSGEWY

HYTGEKEKILNNTWFEDSKNLCPVVVSQNRSVKGFLEIASDKYRIIKVDL

-continued

VFPVLHGKNGEDGTLQGIFELAGIPVVGCDTLSSALCMDKDRAHKLVSLA

GISVPKSVTFKRFNEEAAMKEIEANLTYPLFIKPVRAGSSFGITKVIEKQ

ELDAAIELAFEHDTEVIVEETINGFEVGCAVLGIDELIVGRVDEIELSSG

FFDYTEKYTLKSSKIYMPARIDAEAEKRIQEAAVTIYKALGCSGFSRVDM

FYTPSGEIVFNEVNTIPGFTSHSRYPNMMKGIGLSFSQMLDKLIGLYVE

SEQ ID No. 94:
MQNKKIAVIFGGNSTEYEVSLQSASAVFENINTNKFDIIPIGITRSGEWY

HYTGEKEKILNNTWFEDSKNLCPVVVSQNRSVKGFLEIASDKYRIIKVDL

VFPVLHGKNGENGTLQGIFELAGIPVVGCDTLSSALCMDKDRAHKLVSLA

GISVPKSVTFKRFNEEAAMKEIEANLTYPLFIKPVRAGSSFGITKVIEKQ

ELDAAIELAFEHDTEVIVEETINGFEVGCAVLGIDELIVGRVDEIELSSG

FFDYTEKYTLKSSKIYMPARIDAEAEKRIQEAAVTIYKALGCSGFSRVDM

FYTPSGEIVFNEVNTIPGFTSHSRYPNMMKGIGLSFSQMLDKLIGLYVE said markers of type VanG preferably being selected from the peptides of sequence SEQ ID No. 95 to SEQ ID No. 102 as defined below:

| Peptide SEQ ID No. | Amino acid sequence | Position of the peptide in the VanG protein or proteins |
|---|---|---|
| SEQ ID No. 95 | AGSSFGITK | 187-195 for the proteins of SEQ No. 92, 93, 94 |
| SEQ ID No. 96 | ALGCSGFSR | 289-297 for the proteins of SEQ No. 92, 93, 94 |
| SEQ ID No. 97 | IDAEAEK | 271-277 for the proteins of SEQ No. 92, 93, 94 |
| SEQ ID No. 98 | IYMPAR | 265-270 for the proteins of SEQ No. 92, 93, 94 |
| SEQ ID No. 99 | LIGLYVE | 343-349 for the proteins of SEQ No. 92, 93, 94 |

-continued

| Peptide SEQ ID No. | Amino acid sequence | Position of the peptide in the VanG protein or proteins |
|---|---|---|
| SEQ ID No. 100 | LVSLAGISVPK | 146-156 for the proteins of SEQ No. 92, 93, 94 |
| SEQ ID No. 101 | VDEIELSSGFFDYTEK | 242-257 for the proteins of SEQ No. 92, 93, 94 |
| SEQ ID No. 102 | YPNMMK | 325-330 for the proteins of SEQ No. 92, 93, 94 |

Advantageously, the markers of type VanG selected from the peptides of sequence SEQ ID No. 95, SEQ ID No. 96, SEQ ID No. 97, SEQ ID No. 98, SEQ ID No. 100 and SEQ ID No. 102 are detected after induction of the mechanism of resistance.

Advantageously, the markers of type VanG selected from the peptides of sequence SEQ ID No. 97 and SEQ ID No. 100 are detected without an induction step.

According to another embodiment of the invention, detection of a mechanism of resistance to glycopeptides, induced by expression of the protein VanL, is characterized by the detection of at least one peptide belonging to the protein VanL of sequence SEQ ID No. 103.

SEQ ID No. 103:
MMKLKKIAIIFGGQSSEYEVSLKSTVSVLETLSTCNFEIIKIGIDLGGKW

YLTTSNNKDIEYDVWQTDPSLQEIIPCFNNRGFYNKTTNKYFRPDVLFPI

LHGGTGEDGTLQGVFELMNIPYVGCGVTPSAICMDKYLLHEFAQSVGVKS

APTLIIRTRNCKDEIDKFIEKNDFPIFVKPNEAGSSKGINKVNEPDKLED

ALTEAFKYSKSVIIQKAIIGREIGCAVLGNEKLLVGECDEVSLNSDFFDY

TEKYQMISAKVNIPASISVEFSNEMKKQAQLLYRLLGCSGLARIDFFLSD

NNEILLNEINTLPGFTEHSRYPKMMEAVGVTYKEIITKLINLAEEKYYG said peptides of type VanL preferably being selected from the peptides of sequence SEQ ID No. 104 to SEQ ID No. 120 as defined below:

| Peptide SEQ ID No. | Amino acid sequence | Position of the peptide in the VanL protein or proteins |
|---|---|---|
| SEQ ID No. 104 | DIEYDVWQTDPSLQEIIPCFNNR | 59-81 for the protein of SEQ No. 103 |
| SEQ ID No. 105 | EIGCAVLGNEK | 222-232 for the protein of SEQ No. 103 |
| SEQ ID No. 106 | IAIIFGGQSSEYEVSLK | 7-23 for the protein of SEQ No. 103 |
| SEQ ID No. 107 | IGIDLGGK | 42-49 for the protein of SEQ No. 103 |
| SEQ ID No. 108 | LEDALTEAFK | 198-207 for the protein of SEQ No. 103 |
| SEQ ID No. 109 | LINLAEEK | 339-346 for the protein of SEQ No. 103 |
| SEQ ID No. 110 | LLGCSGLAR | 285-293 for the protein of SEQ No. 103 |
| SEQ ID No. 111 | LLVGECDEVSLNSDFFDYTEK | 233-253 for the protein of SEQ No. 103 |
| SEQ ID No. 112 | MMEAVGVTYK | 324-333 for the protein of SEQ No. 103 |
| SEQ ID No. 113 | NDFPIFVKPNEAGSSK | 172-187 for the protein of SEQ No. 103 |
| SEQ ID No. 114 | QAQLLYR | 278-284 for the protein of SEQ No. 103 |
| SEQ ID No. 115 | SAPTLIIR | 150-157 for the protein of SEQ No. 103 |
| SEQ ID No. 116 | STVSVLETLSTCNFEIIK | 24-41 for the protein of SEQ No. 103 |

-continued

| Peptide SEQ ID No. | Amino acid sequence | Position of the peptide in the VanL protein or proteins |
|---|---|---|
| SEQ ID No. 117 | VNIPASISVEFSNEMK | 261-276 for the protein of SEQ No. 103 |
| SEQ ID No. 118 | WYLTTSNNK | 50-58 for the protein of SEQ No. 103 |
| SEQ ID No. 119 | YLLHEFAQSVGVK | 137-149 for the protein of SEQ No. 103 |
| SEQ ID No. 120 | YQMISAK | 254-260 for the protein of SEQ No. 103 |

According to another embodiment of the invention, detection of a mechanism of resistance to glycopeptides, induced by expression of the protein VanM, is characterized by the detection of at least one peptide belonging to the protein VanM of sequence SEQ ID No. 121.

SEQ ID No. 121:
MNRLKIAILFGGCSEEHNVSVKSAAEIANNIDIGKYEPIYIGITQSGVWK

TCEKPCIDWDNEHCRSAVLSPDKKMHGLLIMQDKGYQIQRIDVVFSVLHG

-continued

KSGEDGAIQGLFELSGIPYVGCDIQSSAVCMDKSLAYIIAKNAGIATPEF

QVIYKDDKPAADSFTYPVFVKPARSGSSYGVNKVNSADELDSAIDLARQY

DSKILIEQGVLGYEVGCAVLGNSFDLIVGEVDQIRLQHGIFRIHQEAEPE

KGSENATITVPAELSAEERERIKEAAKNIYKALGCRGLSRVDMFLQDNGR

IVLNEVNTMPGFTSYSRYPRMMVSAGITIPELIDHLIVLAVKE said peptides of type VanM preferably being selected from the peptides of sequence SEQ ID No. 122 to SEQ ID No. 139 as defined below:

| Peptide SEQ ID No. | Amino acid sequence | Position of the peptide in the VanM protein or proteins |
|---|---|---|
| SEQ ID No. 122 | DDKPAADSFTYPVFVKPAR | 156-174 for the protein of SEQ No. 121 |
| SEQ ID No. 123 | GSENATITVPAELSAEER | 252-269 for the protein of SEQ No. 121 |
| SEQ ID No. 124 | IAILFGGCSEEHNVSVK | 6-22 for the protein of SEQ No. 121 |
| SEQ ID No. 125 | IDVVFSVLHGK | 91-101 for the protein of SEQ No. 121 |
| SEQ ID No. 126 | IHQEAEPEK | 243-251 for the protein of SEQ No. 121 |
| SEQ ID No. 127 | IVLNEVNTMPGFTSYSR | 301-317 for the protein of SEQ No. 121 |
| SEQ ID No. 128 | LQHGIFR | 236-242 for the protein of SEQ No. 121 |
| SEQ ID No. 129 | MHGLLIMQDK | 75-84 for the protein of SEQ No. 121 |
| SEQ ID No. 130 | MMVSAGITIPELIDHLIVLAVK | 321-342 for the protein of SEQ No. 121 |
| SEQ ID No. 131 | NAGIATPEFQVIYK | 142-155 for the protein of SEQ No. 121 |
| SEQ ID No. 132 | SAAEIANNIDIGK | 23-35 for the protein of SEQ No. 121 |
| SEQ ID No. 133 | SAVLSPDK | 66-73 for the protein of SEQ No. 121 |
| SEQ ID No. 134 | SGSSYGVNK | 175-183 for the protein of SEQ No. 121 |

-continued

| Peptide SEQ ID No. | Amino acid sequence | Position of the peptide in the VanM protein or proteins |
|---|---|---|
| SEQ ID No. 135 | SLAYIIAK | 134-141 for the protein of SEQ No. 121 |
| SEQ ID No. 136 | TCEKPCIDWDNEHCR | 51-65 for the protein of SEQ No. 121 |
| SEQ ID No. 137 | VDMFLQDNGR | 291-300 for the protein of SEQ No. 121 |
| SEQ ID No. 138 | VNSADELDSAIDLAR | 184-198 for the protein of SEQ No. 121 |
| SEQ ID No. 139 | YEPIYIGITQSGVWK | 36-50 for the protein of SEQ No. 121 |

According to another embodiment of the invention, detection of a mechanism of resistance to glycopeptides, induced by expression of the protein VanN, is characterized by the detection of at least one peptide belonging to the protein VanN of sequence SEQ ID No. 140.

SEQ ID No. 140:
MKKIALIFGGTSAEYEVSLKSAASVLSVLENLNVEIYRIGIASNGKWYLT

FSDNETIANDLWLQDKKLNEITPSFDGRGFYDQAEKVYFKPDVLFPMLHG

-continued

GTGENGTLQGVFECMQIPYVGCGVASSAICMNKYLLHQFAKSVGVMSTPT

QLISSTDEQQVIKNFTELYGFPIFIKPNEAGSSKGISKVHTEAELTKALT

EAFQFSQTVILQKAVSGVEIGCAILGNDQLLVGECDEVSLATDFFDYTEK

YQMTTAKLTVPAKIPVATSREIKRQAQLLYQLLGCQGLARIDFFLTEAGE

ILLNEINTMPGFTNHSRFPAMMAATGITYQELISTLITLAEDK said peptides of type VanN preferably being selected from the peptides of sequence SEQ ID No. 141 to SEQ ID No. 154 as defined below:

| Peptide SEQ ID No. | Amino acid sequence | Position of the peptide in the protein VanN |
|---|---|---|
| SEQ ID No. 141 | ALTEAFQFSQTVILQK | 198-213 for the protein of SEQ No. 140 |
| SEQ ID No. 142 | GFYDQAEK | 79-86 for the protein of SEQ No. 140 |
| SEQ ID No. 143 | IALIFGGTSAEYEVSLK | 4-20 for the protein of SEQ No. 140 |
| SEQ ID No. 144 | IGIASNGK | 39-46 for the protein of SEQ No. 140 |
| SEQ ID No. 145 | IPVATSR | 264-270 for the protein of SEQ No. 140 |
| SEQ ID No. 146 | LNEITPSFDGR | 68-78 for the protein of SEQ No. 140 |
| SEQ ID No. 147 | NFTELYGFPIFIKPNEAGSSK | 164-184 for the protein of SEQ No. 140 |
| SEQ ID No. 148 | QAQLLYQLLGCQGLAR | 275-290 for the protein of SEQ No. 140 |
| SEQ ID No. 149 | SAASVLSVLENLNVEIYR | 21-38 for the protein of SEQ No. 140 |
| SEQ ID No. 150 | SVGVMSTPTQLISSTDEQQVIK | 142-163 for the protein of SEQ No. 140 |
| SEQ ID No. 151 | VHTEAELTK | 189-197 for the protein of SEQ No. 140 |
| SEQ ID No. 152 | WYLTFSDNETIANDLWLQDK | 47-66 for the protein of SEQ No. 140 |

-continued

| Peptide SEQ ID No. | Amino acid sequence | Position of the peptide in the protein VanN |
|---|---|---|
| SEQ ID No. 153 | YLLHQFAK | 134-141 for the protein of SEQ No. 140 |
| SEQ ID No. 154 | YQMTTAK | 251-257 for the protein of SEQ No. 140 |

The method of the invention and its advantages will become clearer from the rest of the present description, which presents several nonlimiting embodiment examples of said method.

EXAMPLE 1

Preparation of a Primary Urine Sample by Enrichment with Microorganisms

The following protocol is carried out in 16 steps (steps 5 to 12 are optional and could be omitted if the enriched sample is treated subsequently according to example 6 and the subsequent examples):

1. Centrifugation of 5 mL of contaminated urine, at 2000 g for 30 seconds
2. Recovery of the supernatant
3. Centrifugation at 15000 g for 5 minutes
4. Removal of the supernatant
5. Washing of the pellet with 3 mL of distilled water by resuspension
6. Centrifugation at 15000 g for 5 minutes
7. Removal of the supernatant
8. Put the pellet in contact with solvent (8 volumes acetone to 1 volume of methanol) at 1/10 dilution
9. Leave for 1 hour at −20° C.
10. Centrifugation at 15000 g for 5 minutes
11. Removal of the supernatant
12. Put the pellet in contact with solvent (8 volumes acetone to 1 volume of methanol) at 1/10 dilution
13. Leave for 1 hour at −20° C.
14. Centrifugation at 15000 g for 5 minutes
15. Removal of the supernatant The pellet constitutes the sample enriched with microorganism.

EXAMPLE 2

Culture of the Sample on Culture Medium in the Absence of Antibiotic

The optimal culture media and the optimal culture conditions are different depending on the species of microorganism. By default, the sample is seeded on various media:

Columbia sheep blood agar (bioMérieux reference 43041) for 18 to 24 h at 35° C., in aerobic or anaerobic atmosphere;

TSA agar (bioMérieux reference 43011) for 18 to 24 h at 37° C.

EXAMPLE 3

Culture of the Sample on Culture Medium in the Presence of Antibiotic

The sample is seeded on medium:

VRE agar (bioMérieux reference 43002) for 18 to 24 h at 35° C., in aerobic or anaerobic atmosphere. This medium contains vancomycin.

EXAMPLE 4

Identification of Microorganisms by Biochemical Profile

Identification is performed as follows:

1. Selection of isolated colonies obtained according to example 2 or example 3, or by enrichment of microorganisms present in a primary sample according to example 1.
2. Observing aseptic conditions, transfer of 3.0 mL of sterile aqueous saline solution (at 0.45-0.50% of NaCl, of pH 4.5 to 7.0) to a transparent plastic (polystyrene) test tube
3. Using a rod or a sterile swab, transfer of a sufficient number of identical colonies to the tube of saline solution prepared in step 2 and adjustment of the bacterial suspension between 0.50 and 0.63 McFarland with a calibrated DENSICHEK of the VITEK®
4. Placement of the tube of bacterial suspension and of a VITEK® identification card on a VITEK® cassette
5. Loading of the cassette in the VITEK® instrument
6. The operations of filling, sealing, incubation and reading are automatic
7. Acquisition of a biochemical profile Identification with the VITEK® system carried out by comparison with biochemical profiles of known strains

EXAMPLE 5

Identification of Microorganisms from a Sample by MALDI-TOF

Identification is performed as follows:

1. Transfer, using a 1 μl loop, of a portion of microorganism colony obtained according to example 2 or 3, or of an enriched sample according to example 1, and uniform deposition on a plate for mass spectrometry by MALDI-TOF
2. Covering the deposit with 1 μl of matrix. The matrix used is a saturated solution of HCCA (alpha-cyano-4-hydroxycinnamic acid) in organic solvent (50% acetonitrile and 2.5% trifluoroacetic acid)
3. Drying at room temperature 4. Putting the plate in the mass spectrometer
5. Acquisition of a mass spectrum
6. Comparison of the spectrum obtained with the spectra contained in a knowledge base
7. Identification of the microorganism by comparing the peaks obtained with those in the knowledge base

EXAMPLE 6

Identification of Microorganisms from a Sample by ESI-MS

Identification is performed as follows:
1. Sampling of a microorganism colony obtained according to example 2 or 3, or of an enriched sample according to example 1, and suspension in 100 μl of demineralized water.
2. Centrifugation at 3000 g for 5 minutes.
3. Removal of the supernatant.
4. Resuspension in 100 μl of demineralized water.
5. Centrifugation at 3000 g for 5 minutes.
6. Removal of the supernatant.
7. Resuspension in 100 μl of a mixture of acetonitrile, demineralized water, formic acid (50/50/0.1%).
8. Filtration with a filter of porosity 0.45 μm.
9. Injection in a mass spectrometer in single MS mode.
10. Acquisition of a mass spectrum.
11. Comparison of the spectrum obtained with the spectra contained in a knowledge base.
12. Identification of the microorganism by reference to reference spectra.

EXAMPLE 7

Obtaining Digested Proteins from Microorganisms

The following protocol is carried out in 17 steps:
1. Sampling a microorganism colony, obtained according to example 2 or 3, or an enriched sample according to example 1, and suspension in 10 to 100 μl of a 6M solution of guanidine hydrochloride, 50 mM Tris-HCl, pH=8.0.
2. Addition of dithiothreitol (DTT) to obtain a final concentration of 5 mM.
3. Reduction for 20 minutes at 95° C. in a water bath.
4. Cooling of the tubes to room temperature.
5. Addition of iodoacetamide to obtain a final concentration of 12.5 mM.
6. Alkylation for 40 minutes at room temperature in the dark.
7. Dilution by a factor of 6 with a 50 mM solution of $NH_4HCO_3$, pH=8.0 to obtain a final concentration of guanidine hydrochloride of 1M.
8. Addition of 1 μg of trypsin.
9. Digestion at 37° C. for 6 hours overnight.
10. Addition of formic acid until the pH is below 4 to stop the reaction.
11. The sample volume is made up to 1 mL with water/formic acid 0.5% (v/v).
12. Equilibration of the Waters Oasis HLB columns with 1 ml of methanol and then 1 ml $H_2O$/formic acid 0.1% (v/v)
13. Deposition of the sample, which flows by gravity
14. Washing with 1 ml $H_2O$/formic acid 0.1% (v/v)
15. Elution with 1 ml of a mixture of 80% of methanol and 20% of water/formic acid 0.1% (v/v)
16. The eluate is evaporated with an evaporator of the SpeedVac® SPD2010 type (Thermo Electron Corporation, Waltham, Mass., United States of America), for 2 hours, to obtain a volume of about 100 μl.

The eluate is then taken up in a solution of water/formic acid 0.5% (v/v) quantity sufficient (Q.S.) for 200 μl

EXAMPLE 8

Identification of Resistance to Glycopeptides, without Induction, of Type VanA, VanB, VanC1, VanD, VanE and VanG Samples Smp1 to Smp13 are identified according to one of the methods described in examples 1 to 6. Identification of the species is reported in TABLE 1.

TABLE 1

| Name | Species |
|---|---|
| Smp1 | *E. faecalis* |
| Smp2 | *E. gallinarum* |
| Smp3 | *E. faecalis* |
| Smp4 | *E. faecalis* |
| Smp5 | *E. faecalis* |
| Smp6 | *E. faecalis* |
| Smp7 | *E. faecalis* |
| Smp8 | *E. faecium* |
| Smp9 | *E. faecium* |
| Smp10 | *E. faecalis* |
| Smp11 | *E. faecium* |

Samples Smp1 to Smp11 correspond to a species that may comprise a mechanism of resistance of the Van type. The following method is then employed for investigating such a mechanism.

The microorganism colony is obtained according to example 2, treated according to example 7, and then a volume of 50 μl of digested proteins is injected and analyzed according to the following conditions:

Dionex Ultimate 3000 chromatographic chain from the company Dionex Corporation (Sunnyvale, United States of America).

Waters BEH130 C18 column, 2.1 mm inside diameter, length 100 mm, particle size 3.5 μm (Waters, Saint-Quentin en Yvelines, France).

Solvent A: $H_2O$+0.1% formic acid.

Solvent B: ACN+0.1% formic acid.

HPLC gradient defined in TABLE 2 below.

TABLE 2

| Time (min) | Flow (μl) | Solvent A (%) | Solvent B (%) |
|---|---|---|---|
| 0 | 300 | 98 | 2 |
| 3 | 300 | 98 | 2 |
| 28 | 300 | 63 | 37 |
| 30 | 300 | 0 | 100 |
| 38 | 300 | 0 | 100 |
| 38.1 | 300 | 98 | 2 |
| 45 | 300 | 98 | 2 |

The eluate leaving the chromatographic column is directly injected in the ionization source of the mass spectrometer of the QTRAP® 5500 type from the company Applied Biosystems (Foster City, United States of America).

The peptides resulting from digestion of the proteins of the microorganism are analyzed by the mass spectrometer in MRM mode. Only the peptides shown in TABLE 3 are detected. For this, the fragment or fragments shown in TABLE 3 are detected.

TABLE 3

| Transition number | Protein | Peptide | State of charge of precursor | First-generation ion fragment |
|---|---|---|---|---|
| 1 | VanA | IHQEVEPEK (SEQ ID No. 5) | 2 | y5 single-charged |
| 2 | VanA | IHQEVEPEK (SEQ ID No. 5) | 2 | y6 single-charged |
| 3 | VanA | IHQEVEPEK (SEQ ID No. 5) | 2 | y7 single-charged |
| 4 | VanA | LIVLALK (SEQ ID No. 6) | 2 | y4 single-charged |
| 5 | VanA | LIVLALK (SEQ ID No. 6) | 2 | y5 single-charged |
| 6 | VanA | LIVLALK (SEQ ID No. 6) | 2 | y6 single-charged |
| 7 | VanA | LQYGIFR (SEQ ID No. 7) | 2 | y4 single-charged |
| 8 | VanA | LQYGIFR (SEQ ID No. 7) | 2 | y5 single-charged |
| 9 | VanA | LQYGIFR (SEQ ID No. 7) | 2 | y6 single-charged |
| 10 | VanA | MHGLLVK (SEQ ID No. 8) | 2 | b5 single-charged |
| 11 | VanA | MHGLLVK (SEQ ID No. 8) | 2 | y5 single-charged |
| 12 | VanA | MHGLLVK (SEQ ID No. 8) | 2 | y6 single-charged |
| 13 | VanA | MMAAAGIALPELIDR (SEQ ID No. 9) | 2 | y6 single-charged |
| 14 | VanA | MMAAAGIALPELIDR (SEQ ID No. 9) | 2 | y7 single-charged |
| 15 | VanA | MMAAAGIALPELIDR (SEQ ID No. 9) | 2 | y8 single-charged |
| 16 | VanA | NAGIATPAFWVINK (SEQ ID No. 10) | 2 | y10 single-charged |
| 17 | VanA | NAGIATPAFWVINK (SEQ ID No. 10) | 2 | y8 single-charged |
| 18 | VanA | NAGIATPAFWVINK (SEQ ID No. 10) | 2 | y9 single-charged |
| 19 | VanA | SAIEIAANINK (SEQ ID No. 11) | 2 | y6 single-charged |
| 20 | VanA | SAIEIAANINK (SEQ ID No. 11) | 2 | y7 single-charged |
| 21 | VanA | SAIEIAANINK (SEQ ID No. 11) | 2 | y8 single-charged |
| 22 | VanA | SGSSFGVK (SEQ ID No. 12) | 2 | y5 single-charged |
| 23 | VanA | SGSSFGVK (SEQ ID No. 12) | 2 | y6 single-charged |
| 24 | VanA | SGSSFGVK (SEQ ID No. 12) | 2 | y7 single-charged |
| 25 | VanA | SLTYIVAK (SEQ ID No. 13) | 2 | y4 single-charged |

TABLE 3-continued

| Transition number | Protein | Peptide | State of charge of precursor | First-generation ion fragment |
|---|---|---|---|---|
| 26 | VanA | SLTYIVAK (SEQ ID No. 13) | 2 | y5 single-charged |
| 27 | VanA | SLTYIVAK (SEQ ID No. 13) | 2 | y6 single-charged |
| 28 | VanA | VDMFLQDNGR (SEQ ID No. 14) | 2 | y6 single-charged |
| 29 | VanA | VDMFLQDNGR (SEQ ID No. 14) | 2 | y7 single-charged |
| 30 | VanA | VDMFLQDNGR (SEQ ID No. 14) | 2 | y8 single-charged |
| 31 | VanA | VNSADELDYAIESAR (SEQ ID No. 15) | 2 | y6 single-charged |
| 32 | VanA | VNSADELDYAIESAR (SEQ ID No. 15) | 2 | y7 single-charged |
| 33 | VanA | VNSADELDYAIESAR (SEQ ID No. 15) | 2 | y8 single-charged |
| 34 | VanA | YEPLYIGITK (SEQ ID No. 16) | 2 | y7 single-charged |
| 35 | VanA | YEPLYIGITK (SEQ ID No. 16) | 2 | y8 single-charged |
| 36 | VanA | YEPLYIGITK (SEQ ID No. 16) | 2 | y8 double-charged |
| 37 | VanB | FDPHYIGITK (SEQ ID No. 29) | 2 | y6 single-charged |
| 38 | VanB | FDPHYIGITK (SEQ ID No. 29) | 2 | y7 double-charged |
| 39 | VanB | FDPHYIGITK (SEQ ID No. 29) | 2 | y8 double-charged |
| 40 | VanB | IDVAFPVLHGK (SEQ ID No. 30) | 2 | y6 single-charged |
| 41 | VanB | IDVAFPVLHGK (SEQ ID No. 30) | 2 | y7 single-charged |
| 42 | VanB | IDVAFPVLHGK (SEQ ID No. 30) | 2 | y8 single-charged |
| 43 | VanB | IHQENEPEK (SEQ ID No. 31) | 2 | y5 single-charged |
| 44 | VanB | IHQENEPEK (SEQ ID No. 31) | 2 | y6 single-charged |
| 45 | VanB | IHQENEPEK (SEQ ID No. 31) | 2 | y7 single-charged |
| 46 | VanB | LSHGIFR (SEQ ID No. 32) | 2 | y4 single-charged |
| 47 | VanB | LSHGIFR (SEQ ID No. 32) | 2 | y5 single-charged |
| 48 | VanB | LSHGIFR (SEQ ID No. 32) | 2 | y6 single-charged |
| 49 | VanB | SLAYILTK (SEQ ID No. 33) | 2 | y5 single-charged |
| 50 | VanB | SLAYILTK (SEQ ID No. 33) | 2 | y6 single-charged |

TABLE 3-continued

| Transition number | Protein | Peptide | State of charge of precursor | First-generation ion fragment |
|---|---|---|---|---|
| 51 | VanB | SLAYILTK (SEQ ID No. 33) | 2 | y7 single-charged |
| 52 | VanB | THGLLVMK (SEQ ID No. 34) | 2 | b5 single-charged |
| 53 | VanB | THGLLVMK (SEQ ID No. 34) | 2 | b6 single-charged |
| 54 | VanB | THGLLVMK (SEQ ID No. 34) | 2 | y6 single-charged |
| 55 | VanB | VQETAK (SEQ ID No. 35) | 2 | y3 single-charged |
| 56 | VanB | VQETAK (SEQ ID No. 35) | 2 | y4 single-charged |
| 57 | VanB | VQETAK (SEQ ID No. 35) | 2 | y5 single-charged |
| 58 | VanC1 | EQAQLLYR (SEQ ID No. 59) | 2 | y3 single-charged |
| 59 | VanC1 | EQAQLLYR (SEQ ID No. 59) | 2 | y4 single-charged |
| 60 | VanC1 | EQAQLLYR (SEQ ID No. 59) | 2 | y6 single-charged |
| 61 | VanC1 | FIQDHGFPIFIKPNEAGSSK (SEQ ID No. 60) | 3 | b7 single-charged |
| 62 | VanC1 | FIQDHGFPIFIKPNEAGSSK (SEQ ID No. 60) | 3 | y8 single-charged |
| 63 | VanC1 | FIQDHGFPIFIKPNEAGSSK (SEQ ID No. 60) | 3 | y9 single-charged |
| 64 | VanC1 | IVPDVLFPVLHGK (SEQ ID No. 61) | 2 | y11 double-charged |
| 65 | VanC1 | IVPDVLFPVLHGK (SEQ ID No. 61) | 3 | y11 double-charged |
| 66 | VanC1 | IVPDVLFPVLHGK (SEQ ID No. 61) | 3 | y11 triple-charged |
| 67 | VanC1 | NC[CAM]HQLTFSSQGFILGEK (SEQ ID No. 62) | 3 | y5 single-charged |
| 68 | VanC1 | NC[CAM]HQLTFSSQGFILGEK (SEQ ID No. 62) | 3 | y7 single-charged |
| 69 | VanC1 | NC[CAM]HQLTFSSQGFILGEK (SEQ ID No. 62) | 3 | y8 single-charged |
| 70 | VanC1 | NDTWLEDHK (SEQ ID No. 63) | 2 | y5 single-charged |
| 71 | VanC1 | NDTWLEDHK (SEQ ID No. 63) | 2 | y6 single-charged |
| 72 | VanC1 | NDTWLEDHK (SEQ ID No. 63) | 2 | y7 single-charged |
| 73 | VanC1 | NLGLTGLAR (SEQ ID No. 64) | 2 | y4 single-charged |
| 74 | VanC1 | NLGLTGLAR (SEQ ID No. 64) | 2 | y5 single-charged |
| 75 | VanC1 | NLGLTGLAR (SEQ ID No. 64) | 2 | y7 single-charged |

TABLE 3-continued

| Transition number | Protein | Peptide | State of charge of precursor | First-generation ion fragment |
|---|---|---|---|---|
| 76 | VanC1 | TALQSALTTAFAYGSTVLIQK (SEQ ID No. 65) | 3 | y7 single-charged |
| 77 | VanC1 | TALQSALTTAFAYGSTVLIQK (SEQ ID No. 65) | 3 | y8 single-charged |
| 78 | VanC1 | TALQSALTTAFAYGSTVLIQK (SEQ ID No. 65) | 3 | y9 single-charged |
| 79 | VanC1 | WLLHQLADTMGIASAPTLLLSR (SEQ ID No. 66) | 3 | y10 single-charged |
| 80 | VanC1 | WLLHQLADTMGIASAPTLLLSR (SEQ ID No. 66) | 3 | y7 single-charged |
| 81 | VanC1 | WLLHQLADTMGIASAPTLLLSR (SEQ ID No. 66) | 3 | y9 single-charged |
| 82 | VanC1 | YENDPATIDR (SEQ ID No. 67) | 2 | b4 single-charged |
| 83 | VanC1 | YENDPATIDR (SEQ ID No. 67) | 2 | y6 single-charged |
| 84 | VanC1 | YENDPATIDR (SEQ ID No. 67) | 2 | y8 single-charged |
| 85 | VanC1 | YQLISATITVPAPLPLALESQIK (SEQ ID No. 68) | 3 | y11 double-charged |
| 86 | VanC1 | YQLISATITVPAPLPLALESQIK (SEQ ID No. 68) | 3 | y13 double-charged |
| 87 | VanC1 | YQLISATITVPAPLPLALESQIK (SEQ ID No. 68) | 3 | y9 single-charged |
| 88 | VanC2 | ITVPAPLPETIETK (SEQ ID No. 69) | 2 | y11 double-charged |
| 89 | VanC2 | ITVPAPLPETIETK (SEQ ID No. 69) | 2 | y7 single-charged |
| 90 | VanC2 | ITVPAPLPETIETK (SEQ ID No. 69) | 2 | y9 single-charged |
| 91 | VanC2 | QDTWLLDTK (SEQ ID No. 70) | 2 | y4 single-charged |
| 92 | VanC2 | QDTWLLDTK (SEQ ID No. 70) | 2 | y5 single-charged |
| 93 | VanC2 | QDTWLLDTK (SEQ ID No. 70) | 2 | y6 single-charged |
| 94 | VanC2 | YQLISAK (SEQ ID No. 71) | 2 | y3 single-charged |
| 95 | VanC2 | YQLISAK (SEQ ID No. 71) | 2 | y5 single-charged |
| 96 | VanC2 | YQLISAK (SEQ ID No. 71) | 2 | y6 single-charged |
| 97 | VanD | GSENAVIR (SEQ ID No. 80) | 2 | y4 single-charged |
| 98 | VanD | GSENAVIR (SEQ ID No. 80) | 2 | y5 single-charged |
| 99 | VanD | GSENAVIR (SEQ ID No. 80) | 2 | y6 single-charged |
| 100 | VanD | IDLFLR (SEQ ID No. 81) | 2 | y3 single-charged |

TABLE 3-continued

| Transition number | Protein | Peptide | State of charge of precursor | First-generation ion fragment |
|---|---|---|---|---|
| 101 | VanD | IDLFLR (SEQ ID No. 81) | 2 | y4 single-charged |
| 102 | VanD | IDLFLR (SEQ ID No. 81) | 2 | y5 single-charged |
| 103 | VanD | IHQEAQPEK (SEQ ID No. 82) | 2 | y3 single-charged |
| 104 | VanD | IHQEAQPEK (SEQ ID No. 82) | 2 | y7 single-charged |
| 105 | VanD | IHQEAQPEK (SEQ ID No. 82) | 2 | y8 double-charged |
| 106 | VanD | SGSSFGVNK (SEQ ID No. 83) | 2 | y5 single-charged |
| 107 | VanD | SGSSFGVNK (SEQ ID No. 83) | 2 | y6 single-charged |
| 108 | VanD | SGSSFGVNK (SEQ ID No. 83) | 2 | y7 single-charged |
| 109 | VanE | AIDEASK (SEQ ID No. 85) | 2 | y4 single-charged |
| 110 | VanE | AIDEASK (SEQ ID No. 85) | 2 | y5 single-charged |
| 111 | VanE | AIDEASK (SEQ ID No. 85) | 2 | y6 single-charged |
| 112 | VanE | FPMMMNEIGMDYK (SEQ ID No. 86) | 2 | y9 single-charged |
| 113 | VanE | FPMMMNEIGMDYK (SEQ ID No. 86) | 2 | y12 double-charged |
| 114 | VanE | FPMMMNEIGMDYK (SEQ ID No. 86) | 2 | y5 single-charged |
| 115 | VanE | IMLHQFAEAIGVK (SEQ ID No. 87) | 2 | y10 double-charged |
| 116 | VanE | IMLHQFAEAIGVK (SEQ ID No. 87) | 2 | y8 single-charged |
| 117 | VanE | IMLHQFAEAIGVK (SEQ ID No. 87) | 2 | y9 single-charged |
| 118 | VanE | NMESIDYNVMK (SEQ ID No. 88) | 2 | y6 single-charged |
| 119 | VanE | NMESIDYNVMK (SEQ ID No. 88) | 2 | y7 single-charged |
| 120 | VanE | NMESIDYNVMK (SEQ ID No. 88) | 2 | y8 single-charged |
| 121 | VanE | SAVAIIK (SEQ ID No. 89) | 2 | y4 single-charged |
| 122 | VanE | SAVAIIK (SEQ ID No. 89) | 2 | y5 single-charged |
| 123 | VanE | SAVAIIK (SEQ ID No. 89) | 2 | y6 single-charged |
| 124 | VanE | STPSMIIEK (SEQ ID No. 90) | 2 | y6 single-charged |
| 125 | VanE | STPSMIIEK (SEQ ID No. 90) | 2 | y7 single-charged |

TABLE 3-continued

| Transition number | Protein | Peptide | State of charge of precursor | First-generation ion fragment |
|---|---|---|---|---|
| 126 | VanE | STPSMIIEK (SEQ ID No. 90) | 2 | y7 double-charged |
| 127 | VanE | YNLVTAEILLPAK (SEQ ID No. 91) | 2 | y4 single-charged |
| 128 | VanE | YNLVTAEILLPAK (SEQ ID No. 91) | 2 | y8 single-charged |
| 129 | VanE | YNLVTAEILLPAK (SEQ ID No. 91) | 2 | y9 single-charged |
| 130 | VanG | AGSSFGITK (SEQ ID No. 95) | 2 | y5 single-charged |
| 131 | VanG | AGSSFGITK (SEQ ID No. 95) | 2 | y7 single-charged |
| 132 | VanG | AGSSFGITK (SEQ ID No. 95) | 2 | y8 single-charged |
| 133 | VanG | ALGC[CAM]SGFSR (SEQ ID No. 96) | 2 | y5 single-charged |
| 134 | VanG | ALGC[CAM]SGFSR (SEQ ID No. 96) | 2 | y6 single-charged |
| 135 | VanG | ALGC[CAM]SGFSR (SEQ ID No. 96) | 2 | y7 single-charged |
| 136 | VanG | IDAEAEK (SEQ ID No. 97) | 2 | y4 single-charged |
| 137 | VanG | IDAEAEK (SEQ ID No. 97) | 2 | y5 single-charged |
| 138 | VanG | IDAEAEK (SEQ ID No. 97) | 2 | y6 single-charged |
| 139 | VanG | IYMPAR (SEQ ID No. 98) | 2 | y3 single-charged |
| 140 | VanG | IYMPAR (SEQ ID No. 98) | 2 | y4 single-charged |
| 141 | VanG | IYMPAR (SEQ ID No. 98) | 2 | y5 single-charged |
| 142 | VanG | LIGLYVE (SEQ ID No. 99) | 2 | b4 single-charged |
| 143 | VanG | LIGLYVE (SEQ ID No. 99) | 2 | b5 single-charged |
| 144 | VanG | LIGLYVE (SEQ ID No. 99) | 2 | b6 single-charged |
| 145 | VanG | LVSLAGISVPK (SEQ ID No. 100) | 2 | y6 single-charged |
| 146 | VanG | LVSLAGISVPK (SEQ ID No. 100) | 2 | y7 single-charged |
| 147 | VanG | LVSLAGISVPK (SEQ ID No. 100) | 2 | y9 single-charged |
| 148 | VanG | VDEIELSSGFFDYTEK (SEQ ID No. 101) | 2 | y10 single-charged |
| 149 | VanG | VDEIELSSGFFDYTEK (SEQ ID No. 101) | 2 | y4 single-charged |
| 150 | VanG | VDEIELSSGFFDYTEK (SEQ ID No. 101) | 2 | y6 single-charged |

TABLE 3-continued

| Transition number | Protein | Peptide | State of charge of precursor | First-generation ion fragment |
|---|---|---|---|---|
| 151 | VanG | YPNMMK (SEQ ID No. 102) | 2 | y3 single-charged |
| 152 | VanG | YPNMMK (SEQ ID No. 102) | 2 | y4 single-charged |
| 153 | VanG | YPNMMK (SEQ ID No. 102) | 2 | y5 single-charged |

The transitions mentioned in TABLE 3 are detected using the parameters shown in TABLES 4 and 5.

TABLE 4

| Transition number | Retention time | (m/z) filtered in Q1 | (m/z) filtered in Q3 | Collision energy (eV) |
|---|---|---|---|---|
| 1 | 8.75 | 554.79 | 601.32 | 29 |
| 2 | 8.75 | 554.79 | 730.36 | 29 |
| 3 | 8.75 | 554.79 | 858.42 | 29 |
| 4 | 19.71 | 385.28 | 444.32 | 22 |
| 5 | 19.71 | 385.28 | 543.39 | 22 |
| 6 | 19.71 | 385.28 | 656.47 | 22 |
| 7 | 17.91 | 448.75 | 492.29 | 25 |
| 8 | 17.91 | 448.75 | 655.36 | 25 |
| 9 | 17.91 | 448.75 | 783.41 | 25 |
| 10 | 13.32 | 399.24 | 552.3 | 23 |
| 11 | 13.32 | 399.24 | 529.37 | 23 |
| 12 | 13.32 | 399.24 | 666.43 | 23 |
| 13 | 23.29 | 786.42 | 742.41 | 32 |
| 14 | 23.29 | 786.42 | 855.49 | 31 |
| 15 | 23.29 | 786.42 | 926.53 | 34 |
| 16 | 22.44 | 751.41 | 1146.63 | 38 |
| 17 | 22.44 | 751.41 | 974.55 | 38 |
| 18 | 22.44 | 751.41 | 1075.59 | 38 |
| 19 | 15.89 | 572.32 | 630.36 | 25 |
| 20 | 15.89 | 572.32 | 743.44 | 26 |
| 21 | 15.89 | 572.32 | 872.48 | 25 |
| 22 | 10.67 | 384.7 | 537.3 | 20.5 |
| 23 | 10.67 | 384.7 | 624.34 | 18.5 |
| 24 | 10.67 | 384.7 | 681.36 | 19.5 |
| 25 | 15.29 | 447.77 | 430.3 | 25 |
| 26 | 15.29 | 447.77 | 593.37 | 25 |
| 27 | 15.29 | 447.77 | 694.41 | 25 |
| 28 | 16.64 | 597.78 | 702.35 | 29 |
| 29 | 16.64 | 597.78 | 849.42 | 29 |
| 30 | 16.64 | 597.78 | 980.46 | 27 |
| 31 | 18.52 | 826.89 | 646.35 | 41 |
| 32 | 18.52 | 826.89 | 809.42 | 41 |
| 33 | 18.52 | 826.89 | 924.44 | 41 |
| 34 | 19.2 | 598.83 | 807.5 | 31 |
| 35 | 19.2 | 598.83 | 904.55 | 22 |
| 36 | 19.2 | 598.83 | 452.78 | 25 |
| 37 | 15.89 | 595.81 | 694.41 | 33 |
| 38 | 15.89 | 595.81 | 416.24 | 35 |
| 39 | 15.89 | 595.81 | 464.77 | 28 |
| 40 | 19.1 | 598.35 | 650.4 | 29 |
| 41 | 19.1 | 598.35 | 797.47 | 28 |
| 42 | 19.1 | 598.35 | 868.5 | 28 |
| 43 | 4.97 | 562.27 | 616.29 | 30 |
| 44 | 4.97 | 562.27 | 745.34 | 30 |
| 45 | 4.97 | 562.27 | 873.39 | 30 |
| 46 | 12.85 | 415.24 | 492.29 | 23 |
| 47 | 12.85 | 415.24 | 629.35 | 23 |
| 48 | 12.85 | 415.24 | 716.38 | 23 |
| 49 | 17.9 | 454.78 | 637.39 | 25 |
| 50 | 17.9 | 454.78 | 708.43 | 25 |
| 51 | 17.9 | 454.78 | 821.51 | 25 |
| 52 | 14.32 | 449.76 | 522.3 | 25 |
| 53 | 14.32 | 449.76 | 621.37 | 25 |
| 54 | 14.32 | 449.76 | 660.41 | 25 |
| 55 | 1.53 | 338.19 | 319.2 | 20 |

TABLE 4-continued

| Transition number | Retention time | (m/z) filtered in Q1 | (m/z) filtered in Q3 | Collision energy (eV) |
|---|---|---|---|---|
| 56 | 1.53 | 338.19 | 448.24 | 20 |
| 57 | 1.53 | 338.19 | 576.3 | 20 |
| 58 | 14.16 | 510.78 | 451.27 | 24 |
| 59 | 14.16 | 510.78 | 564.35 | 25 |
| 60 | 14.16 | 510.78 | 763.45 | 27 |
| 61 | 19.45 | 744.72 | 845.39 | 43 |
| 62 | 19.45 | 744.72 | 789.37 | 41 |
| 63 | 19.45 | 744.72 | 917.47 | 40 |
| 64 | 22.56 | 717.43 | 611.35 | 30 |
| 65 | 22.56 | 478.62 | 611.35 | 16 |
| 66 | 22.56 | 478.62 | 407.9 | 19 |
| 67 | 19.53 | 655.98 | 559.34 | 34 |
| 68 | 19.53 | 655.98 | 763.43 | 27 |
| 69 | 19.53 | 655.98 | 891.49 | 25 |
| 70 | 12.98 | 579.26 | 641.33 | 31 |
| 71 | 12.98 | 579.26 | 827.4 | 29 |
| 72 | 12.98 | 579.26 | 928.45 | 27 |
| 73 | 16.92 | 457.77 | 416.26 | 22 |
| 74 | 16.92 | 457.77 | 517.31 | 21 |
| 75 | 16.92 | 457.77 | 687.41 | 22 |
| 76 | 27.6 | 728.74 | 788.89 | 29 |
| 77 | 27.6 | 728.74 | 845.51 | 31 |
| 78 | 27.6 | 728.74 | 1008.57 | 31 |
| 79 | 26.39 | 803.11 | 1028.61 | 35 |
| 80 | 26.39 | 803.11 | 799.5 | 30 |
| 81 | 26.39 | 803.11 | 957.57 | 35 |
| 82 | 11.46 | 597.28 | 522.18 | 26 |
| 83 | 11.46 | 597.28 | 672.37 | 33 |
| 84 | 11.46 | 597.28 | 901.44 | 26 |
| 85 | 26.58 | 822.81 | 604.87 | 30 |
| 86 | 26.58 | 822.81 | 688.91 | 26 |
| 87 | 26.58 | 822.81 | 998.59 | 39 |
| 88 | 19.29 | 754.93 | 598.33 | 30 |
| 89 | 19.29 | 754.93 | 817.43 | 45 |
| 90 | 19.29 | 754.93 | 1027.57 | 38 |
| 91 | 18.18 | 560.29 | 476.27 | 30 |
| 92 | 18.18 | 560.29 | 589.36 | 30 |
| 93 | 18.18 | 560.29 | 775.43 | 30 |
| 94 | 13.88 | 411.74 | 305.18 | 23 |
| 95 | 13.88 | 411.74 | 531.35 | 23 |
| 96 | 13.88 | 411.74 | 659.41 | 23 |
| 97 | 9.97 | 423.23 | 458.31 | 25 |
| 98 | 9.97 | 423.23 | 572.35 | 23 |
| 99 | 9.97 | 423.23 | 701.39 | 21 |
| 100 | 19.92 | 388.74 | 435.27 | 19 |
| 101 | 19.92 | 388.74 | 548.36 | 17 |
| 102 | 19.92 | 388.74 | 663.38 | 19 |
| 103 | 5.57 | 540.28 | 373.21 | 35 |
| 104 | 5.57 | 540.28 | 829.41 | 26 |
| 105 | 5.57 | 540.28 | 483.74 | 29 |
| 106 | 10.45 | 441.72 | 564.31 | 23 |
| 107 | 10.45 | 441.72 | 651.35 | 22 |
| 108 | 10.45 | 441.72 | 738.38 | 21 |
| 109 | 4.52 | 367.19 | 434.22 | 21 |
| 110 | 4.52 | 367.19 | 549.25 | 17 |
| 111 | 4.52 | 367.19 | 662.34 | 18 |
| 112 | 21.88 | 803.84 | 1100.48 | 41 |
| 113 | 21.88 | 803.84 | 730.31 | 38 |

TABLE 4-continued

| Transition number | Retention time | (m/z) filtered in Q1 | (m/z) filtered in Q3 | Collision energy (eV) |
|---|---|---|---|---|
| 114 | 21.88 | 803.84 | 613.27 | 46 |
| 115 | 20.03 | 728.9 | 550.3 | 39 |
| 116 | 20.03 | 728.9 | 834.47 | 41 |
| 117 | 20.03 | 728.9 | 962.53 | 39 |
| 118 | 16.81 | 672.3 | 769.35 | 26 |
| 119 | 16.81 | 672.3 | 882.44 | 26 |
| 120 | 16.81 | 672.3 | 969.47 | 26 |
| 121 | 13.59 | 351.23 | 444.32 | 18 |
| 122 | 13.59 | 351.23 | 543.39 | 16 |
| 123 | 13.59 | 351.23 | 614.42 | 17 |
| 124 | 14.51 | 503.27 | 720.4 | 28 |
| 125 | 14.51 | 503.27 | 817.45 | 19 |
| 126 | 14.51 | 503.27 | 409.23 | 20 |
| 127 | 22.39 | 722.92 | 428.29 | 37 |
| 128 | 22.39 | 722.92 | 854.53 | 37 |
| 129 | 22.39 | 722.92 | 955.58 | 37 |
| 130 | 12.77 | 434.23 | 565.33 | 24 |
| 131 | 12.77 | 434.23 | 739.4 | 21 |
| 132 | 12.77 | 434.23 | 796.42 | 22 |
| 133 | 12.41 | 477.73 | 553.27 | 27 |
| 134 | 12.41 | 477.73 | 713.3 | 26 |
| 135 | 12.41 | 477.73 | 770.33 | 24 |
| 136 | 7.63 | 388.2 | 476.24 | 22 |
| 137 | 7.63 | 388.2 | 547.27 | 19 |
| 138 | 7.63 | 388.2 | 662.3 | 19 |
| 139 | 12.85 | 375.7 | 343.21 | 22 |
| 140 | 12.85 | 375.7 | 474.25 | 22 |
| 141 | 12.85 | 375.7 | 637.31 | 22 |
| 142 | 20.72 | 403.74 | 397.28 | 23 |
| 143 | 20.72 | 403.74 | 560.34 | 23 |
| 144 | 20.72 | 403.74 | 659.41 | 23 |
| 145 | 19.66 | 542.34 | 600.37 | 23 |
| 146 | 19.66 | 542.34 | 671.41 | 25 |
| 147 | 19.66 | 542.34 | 871.52 | 23 |
| 148 | 22.14 | 939.94 | 1180.52 | 46 |
| 149 | 22.14 | 939.94 | 540.27 | 46 |
| 150 | 22.14 | 939.94 | 802.36 | 46 |
| 151 | 12.66 | 392.18 | 409.19 | 22 |
| 152 | 12.66 | 392.18 | 523.24 | 22 |
| 153 | 12.66 | 392.18 | 620.29 | 22 |

TABLE 5

| Transition number | Orifice potential | inlet potential before Q0 | Potential at collision cell outlet | Positivity threshold |
|---|---|---|---|---|
| 1 | 80 | 10 | 35 | 2000 |
| 2 | 80 | 10 | 35 | 2000 |
| 3 | 80 | 10 | 35 | 2000 |
| 4 | 80 | 10 | 35 | 1400 |
| 5 | 80 | 10 | 35 | 2000 |
| 6 | 80 | 10 | 35 | 2000 |
| 7 | 80 | 10 | 35 | 2000 |
| 8 | 80 | 10 | 35 | 2000 |
| 9 | 80 | 10 | 35 | 1500 |
| 10 | 80 | 10 | 35 | 4000 |
| 11 | 80 | 10 | 35 | 4000 |
| 12 | 80 | 10 | 35 | 4000 |
| 13 | 120 | 10 | 18 | 2000 |
| 14 | 120 | 10 | 18 | 2000 |
| 15 | 120 | 10 | 18 | 2000 |
| 16 | 80 | 10 | 35 | 2000 |
| 17 | 80 | 10 | 35 | 2000 |
| 18 | 80 | 10 | 35 | 2000 |
| 19 | 90 | 10 | 15 | 2000 |
| 20 | 90 | 10 | 15 | 2000 |
| 21 | 90 | 10 | 15 | 2000 |
| 22 | 85 | 10 | 24 | 2000 |
| 23 | 85 | 10 | 24 | 2000 |
| 24 | 85 | 10 | 24 | 2000 |
| 25 | 80 | 10 | 35 | 2000 |

TABLE 5-continued

| Transition number | Orifice potential | inlet potential before Q0 | Potential at collision cell outlet | Positivity threshold |
|---|---|---|---|---|
| 26 | 80 | 10 | 35 | 1500 |
| 27 | 80 | 10 | 35 | 2000 |
| 28 | 100 | 10 | 17 | 2000 |
| 29 | 100 | 10 | 17 | 2000 |
| 30 | 100 | 10 | 17 | 2000 |
| 31 | 80 | 10 | 35 | 1000 |
| 32 | 80 | 10 | 35 | 2000 |
| 33 | 80 | 10 | 35 | 2000 |
| 34 | 105 | 10 | 20 | 1400 |
| 35 | 105 | 10 | 20 | 2000 |
| 36 | 105 | 10 | 20 | 2000 |
| 37 | 100 | 10 | 11 | 2000 |
| 38 | 100 | 10 | 16 | 2000 |
| 39 | 100 | 10 | 11 | 2000 |
| 40 | 90 | 10 | 16 | 2000 |
| 41 | 90 | 10 | 18 | 2000 |
| 42 | 90 | 10 | 22 | 2000 |
| 43 | 80 | 10 | 35 | 2000 |
| 44 | 80 | 10 | 35 | 2000 |
| 45 | 80 | 10 | 35 | 2000 |
| 46 | 80 | 10 | 35 | 2000 |
| 47 | 80 | 10 | 35 | 2000 |
| 48 | 80 | 10 | 35 | 2000 |
| 49 | 80 | 10 | 35 | 2000 |
| 50 | 80 | 10 | 35 | 2000 |
| 51 | 80 | 10 | 35 | 2000 |
| 52 | 80 | 10 | 35 | 2000 |
| 53 | 80 | 10 | 35 | 2000 |
| 54 | 80 | 10 | 35 | 2000 |
| 55 | 80 | 10 | 35 | 2000 |
| 56 | 80 | 10 | 35 | 2000 |
| 57 | 80 | 10 | 35 | 2000 |
| 58 | 75 | 12 | 11 | 2000 |
| 59 | 75 | 12 | 14 | 2000 |
| 60 | 75 | 12 | 18 | 2000 |
| 61 | 140 | 10 | 35 | 2000 |
| 62 | 140 | 10 | 35 | 2000 |
| 63 | 140 | 10 | 35 | 2000 |
| 64 | 120 | 10 | 35 | 2000 |
| 65 | 70 | 10 | 35 | 2000 |
| 66 | 70 | 10 | 35 | 2000 |
| 67 | 100 | 10 | 35 | 2000 |
| 68 | 100 | 10 | 35 | 2000 |
| 69 | 100 | 10 | 35 | 2000 |
| 70 | 80 | 12 | 15 | 2000 |
| 71 | 80 | 12 | 19 | 2000 |
| 72 | 80 | 12 | 22 | 2000 |
| 73 | 70 | 12 | 10 | 4000 |
| 74 | 70 | 12 | 13 | 4000 |
| 75 | 70 | 12 | 16 | 4000 |
| 76 | 120 | 10 | 35 | 2000 |
| 77 | 120 | 10 | 35 | 2000 |
| 78 | 120 | 10 | 35 | 2000 |
| 79 | 120 | 10 | 35 | 2000 |
| 80 | 120 | 10 | 35 | 2000 |
| 81 | 120 | 10 | 35 | 2000 |
| 82 | 85 | 12 | 13 | 2000 |
| 83 | 85 | 12 | 16 | 2000 |
| 84 | 85 | 12 | 21 | 2000 |
| 85 | 100 | 10 | 35 | 2000 |
| 86 | 100 | 10 | 35 | 2000 |
| 87 | 100 | 10 | 35 | 2000 |
| 88 | 100 | 10 | 35 | 2000 |
| 89 | 100 | 10 | 35 | 2000 |
| 90 | 100 | 10 | 35 | 2000 |
| 91 | 80 | 10 | 35 | 2000 |
| 92 | 80 | 10 | 35 | 2000 |
| 93 | 80 | 10 | 35 | 2000 |
| 94 | 80 | 10 | 35 | 2000 |
| 95 | 80 | 10 | 35 | 2000 |
| 96 | 80 | 10 | 35 | 2000 |
| 97 | 75 | 10 | 11 | 2000 |
| 98 | 75 | 10 | 14 | 2000 |
| 99 | 75 | 10 | 16 | 1800 |
| 100 | 140 | 6 | 10 | 1300 |

TABLE 5-continued

| Transition number | Orifice potential | inlet potential before Q0 | Potential at collision cell outlet | Positivity threshold |
|---|---|---|---|---|
| 101 | 140 | 6 | 14 | 2000 |
| 102 | 140 | 6 | 16 | 2000 |
| 103 | 110 | 12 | 10 | 2000 |
| 104 | 110 | 12 | 20 | 2000 |
| 105 | 110 | 12 | 6 | 2000 |
| 106 | 75 | 12 | 14 | 2000 |
| 107 | 75 | 12 | 16 | 2000 |
| 108 | 75 | 12 | 18 | 2000 |
| 109 | 65 | 12 | 18 | 2000 |
| 110 | 65 | 12 | 23 | 2000 |
| 111 | 65 | 12 | 15 | 2000 |
| 112 | 100 | 10 | 35 | 2000 |
| 113 | 100 | 10 | 35 | 2000 |
| 114 | 100 | 10 | 35 | 2000 |
| 115 | 140 | 9 | 14 | 2000 |
| 116 | 140 | 9 | 34 | 2000 |
| 117 | 140 | 9 | 24 | 2000 |
| 118 | 125 | 9 | 18 | 2000 |
| 119 | 125 | 9 | 21 | 2000 |
| 120 | 125 | 9 | 41 | 2000 |
| 121 | 70 | 12 | 10 | 2000 |
| 122 | 70 | 12 | 23 | 2000 |
| 123 | 70 | 12 | 14 | 2000 |
| 124 | 70 | 12 | 17 | 8000 |
| 125 | 70 | 12 | 20 | 2000 |
| 126 | 70 | 12 | 10 | 2000 |
| 127 | 80 | 10 | 35 | 2000 |
| 128 | 80 | 10 | 35 | 2000 |
| 129 | 80 | 10 | 35 | 2000 |
| 130 | 70 | 12 | 14 | 2000 |
| 131 | 70 | 12 | 18 | 2000 |
| 132 | 70 | 12 | 19 | 2000 |
| 133 | 80 | 12 | 14 | 2000 |
| 134 | 80 | 12 | 18 | 2000 |
| 135 | 80 | 12 | 18 | 2000 |
| 136 | 70 | 12 | 12 | 1600 |
| 137 | 70 | 12 | 13 | 2000 |
| 138 | 70 | 12 | 16 | 2000 |
| 139 | 80 | 10 | 35 | 2000 |
| 140 | 80 | 10 | 35 | 2000 |
| 141 | 80 | 10 | 35 | 2000 |
| 142 | 80 | 10 | 35 | 2000 |
| 143 | 80 | 10 | 35 | 2000 |
| 144 | 80 | 10 | 35 | 2000 |
| 145 | 80 | 12 | 16 | 2000 |
| 146 | 80 | 12 | 14 | 2000 |
| 147 | 80 | 12 | 21 | 2000 |
| 148 | 80 | 10 | 35 | 2000 |
| 149 | 80 | 10 | 35 | 2000 |
| 150 | 80 | 10 | 35 | 2000 |
| 151 | 80 | 10 | 35 | 3000 |
| 152 | 80 | 10 | 35 | 2000 |
| 153 | 80 | 10 | 35 | 2000 |

The other machine variables used are as follows:

Type of scan: MRM
MRM planned: yes
Polarity: Positive
Ionization source: Turbo V™ (Applied BioSystems)
Q1 setting: Filtering with unit resolution
Q3 setting: Filtering with unit resolution
Inter-scan pause: 5.00 ms
Scanning speed: 10 Da/s
Curtain gas: 50.00 psi
Cone voltage: 5500.00 V
Source temperature: 550.00° C.
Spraying gas: 50.00 psi
Heating gas: 40.00 psi
Collision gas inducing dissociation: 9.00 psi
Dynamic filling: inactivated
Total cycle time: 1.2 s
Detection window: 90 s The areas obtained for each of the transitions and for each of the microorganisms investigated were measured. When the area of a transition is greater than or equal to the positivity threshold described in TABLE 5, detection of the transition is regarded as positive and is marked "1" in TABLE 6. When the area of a transition is below the positivity threshold described in TABLE 5, detection of the transition is regarded as negative and is marked "0" in TABLE 6. When the 3 transitions of one and the same peptide are marked "1", detection of the peptide is regarded as positive. One particular case is an exception to this rule. The peptide corresponding to the transitions with numbers 49, 50 and 51 has a transition of very low intensity. In this precise case, when transitions 49 and 50 are marked "1", detection of this peptide will be regarded as positive.

TABLE 6

| Transition number | Smp1 | Smp2 | Smp3 | Smp4 | Smp5 | Smp6 | Smp7 | Smp8 | Smp9 | Smp10 | Smp11 |
|---|---|---|---|---|---|---|---|---|---|---|---|
| 1 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 |
| 4 | 0 | 0 | 0 | 0 | 0 | 0 | 0 | 0 | 0 | 1 | 0 |
| 5 | 0 | 0 | 0 | 0 | 0 | 0 | 0 | 0 | 0 | 1 | 0 |
| 6 | 0 | 0 | 0 | 0 | 0 | 0 | 0 | 0 | 0 | 1 | 0 |
| 7 | 0 | 0 | 0 | 0 | 0 | 0 | 0 | 0 | 0 | 1 | 0 |
| 8 | 0 | 0 | 0 | 0 | 0 | 0 | 0 | 0 | 0 | 1 | 0 |
| 9 | 0 | 0 | 0 | 0 | 0 | 0 | 0 | 0 | 0 | 1 | 0 |
| 10 | 0 | 0 | 0 | 0 | 0 | 0 | 0 | 0 | 0 | 1 | 0 |
| 11 | 0 | 0 | 0 | 0 | 0 | 0 | 0 | 0 | 0 | 1 | 0 |
| 12 | 0 | 0 | 0 | 0 | 0 | 0 | 0 | 0 | 0 | 1 | 0 |
| 13 | 0 | 0 | 0 | 0 | 0 | 0 | 0 | 0 | 0 | 0 | 0 |
| 14 | 0 | 0 | 0 | 0 | 0 | 0 | 0 | 0 | 0 | 0 | 0 |
| 15 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 |
| 18 | 0 | 0 | 0 | 0 | 0 | 0 | 0 | 0 | 0 | 0 | 0 |
| 19 | 0 | 0 | 1 | 0 | 0 | 0 | 0 | 0 | 0 | 1 | 1 |
| 20 | 0 | 0 | 1 | 0 | 0 | 0 | 0 | 0 | 0 | 1 | 1 |

TABLE 6-continued

| Transition number | Smp1 | Smp2 | Smp3 | Smp4 | Smp5 | Smp6 | Smp7 | Smp8 | Smp9 | Smp10 | Smp11 |
|---|---|---|---|---|---|---|---|---|---|---|---|
| 21 | 0 | 0 | 1 | 0 | 0 | 0 | 0 | 0 | 0 | 1 | 1 |
| 22 | 0 | 0 | 1 | 0 | 0 | 0 | 0 | 0 | 0 | 1 | 0 |
| 23 | 0 | 0 | 1 | 0 | 0 | 0 | 0 | 0 | 0 | 1 | 0 |
| 24 | 0 | 0 | 1 | 0 | 0 | 0 | 0 | 0 | 0 | 1 | 0 |
| 25 | 0 | 0 | 0 | 0 | 0 | 0 | 0 | 0 | 0 | 1 | 0 |
| 26 | 0 | 0 | 0 | 0 | 0 | 0 | 0 | 0 | 0 | 1 | 0 |
| 27 | 0 | 0 | 0 | 0 | 0 | 0 | 0 | 0 | 0 | 1 | 0 |
| 28 | 0 | 0 | 0 | 0 | 0 | 0 | 0 | 0 | 0 | 1 | 0 |
| 29 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 |
| 31 | 0 | 0 | 0 | 0 | 0 | 0 | 0 | 0 | 0 | 1 | 0 |
| 32 | 0 | 0 | 0 | 0 | 0 | 0 | 0 | 0 | 0 | 1 | 0 |
| 33 | 0 | 0 | 0 | 0 | 0 | 0 | 0 | 0 | 0 | 1 | 0 |
| 34 | 0 | 0 | 1 | 0 | 0 | 0 | 0 | 0 | 0 | 1 | 1 |
| 35 | 0 | 0 | 1 | 0 | 0 | 0 | 0 | 0 | 0 | 1 | 1 |
| 36 | 0 | 0 | 1 | 0 | 0 | 0 | 0 | 0 | 0 | 1 | 1 |
| 37 | 0 | 0 | 0 | 0 | 0 | 0 | 0 | 0 | 0 | 0 | 0 |
| 38 | 0 | 0 | 0 | 0 | 0 | 0 | 0 | 0 | 0 | 0 | 0 |
| 39 | 0 | 0 | 0 | 0 | 0 | 0 | 0 | 0 | 0 | 0 | 0 |
| 40 | 0 | 0 | 0 | 0 | 0 | 0 | 0 | 0 | 0 | 0 | 0 |
| 41 | 0 | 0 | 0 | 0 | 0 | 0 | 0 | 0 | 0 | 0 | 0 |
| 42 | 0 | 0 | 0 | 0 | 0 | 0 | 0 | 0 | 0 | 0 | 0 |
| 43 | 0 | 0 | 0 | 0 | 0 | 0 | 0 | 0 | 0 | 0 | 0 |
| 44 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 |
| 49 | 0 | 0 | 0 | 0 | 0 | 0 | 0 | 0 | 0 | 0 | 0 |
| 50 | 0 | 0 | 0 | 0 | 0 | 0 | 0 | 0 | 0 | 0 | 0 |
| 51 | 0 | 0 | 0 | 0 | 0 | 0 | 0 | 0 | 0 | 0 | 0 |
| 52 | 0 | 0 | 0 | 0 | 0 | 0 | 0 | 0 | 0 | 0 | 0 |
| 53 | 0 | 0 | 0 | 0 | 0 | 0 | 0 | 0 | 0 | 0 | 0 |
| 54 | 0 | 0 | 0 | 0 | 0 | 0 | 0 | 0 | 0 | 0 | 0 |
| 55 | 0 | 0 | 0 | 0 | 0 | 0 | 0 | 0 | 0 | 0 | 0 |
| 56 | 0 | 0 | 0 | 0 | 0 | 0 | 0 | 0 | 0 | 0 | 0 |
| 57 | 0 | 0 | 0 | 0 | 0 | 0 | 0 | 0 | 0 | 0 | 0 |
| 58 | 0 | 0 | 0 | 0 | 0 | 0 | 0 | 0 | 0 | 0 | 0 |
| 59 | 0 | 0 | 0 | 0 | 0 | 0 | 0 | 0 | 0 | 0 | 1 |
| 60 | 0 | 0 | 0 | 0 | 0 | 0 | 0 | 0 | 0 | 0 | 0 |
| 61 | 0 | 0 | 0 | 0 | 0 | 0 | 0 | 0 | 0 | 0 | 0 |
| 62 | 0 | 0 | 0 | 0 | 0 | 0 | 0 | 0 | 0 | 0 | 0 |
| 63 | 0 | 0 | 0 | 0 | 0 | 0 | 0 | 0 | 0 | 0 | 0 |
| 64 | 0 | 0 | 0 | 0 | 0 | 0 | 0 | 0 | 0 | 0 | 0 |
| 65 | 0 | 0 | 0 | 0 | 0 | 0 | 0 | 0 | 0 | 0 | 0 |
| 66 | 0 | 0 | 0 | 0 | 0 | 0 | 0 | 0 | 0 | 0 | 0 |
| 67 | 0 | 0 | 0 | 0 | 0 | 0 | 0 | 0 | 0 | 0 | 0 |
| 68 | 0 | 0 | 0 | 0 | 0 | 0 | 0 | 0 | 0 | 0 | 0 |
| 69 | 0 | 0 | 0 | 0 | 0 | 0 | 0 | 0 | 0 | 0 | 0 |
| 70 | 0 | 0 | 0 | 0 | 0 | 0 | 0 | 0 | 0 | 0 | 0 |
| 71 | 0 | 0 | 0 | 0 | 0 | 0 | 0 | 0 | 0 | 0 | 0 |
| 72 | 0 | 0 | 0 | 0 | 0 | 0 | 0 | 0 | 0 | 0 | 0 |
| 73 | 0 | 0 | 0 | 0 | 0 | 0 | 0 | 0 | 0 | 0 | 0 |
| 74 | 0 | 0 | 0 | 0 | 0 | 0 | 0 | 0 | 0 | 0 | 0 |
| 75 | 0 | 0 | 0 | 0 | 0 | 0 | 0 | 0 | 0 | 0 | 0 |
| 76 | 0 | 0 | 0 | 0 | 0 | 0 | 0 | 0 | 0 | 0 | 0 |
| 77 | 0 | 0 | 0 | 0 | 0 | 0 | 0 | 0 | 0 | 0 | 0 |
| 78 | 0 | 0 | 0 | 0 | 0 | 0 | 0 | 0 | 0 | 0 | 0 |
| 79 | 0 | 0 | 0 | 0 | 0 | 0 | 0 | 0 | 0 | 0 | 0 |
| 80 | 0 | 1 | 0 | 0 | 0 | 0 | 0 | 0 | 0 | 0 | 0 |
| 81 | 0 | 0 | 0 | 0 | 0 | 0 | 0 | 0 | 0 | 0 | 0 |
| 82 | 0 | 0 | 0 | 0 | 0 | 0 | 0 | 0 | 0 | 0 | 0 |
| 83 | 0 | 0 | 0 | 0 | 0 | 0 | 0 | 0 | 0 | 0 | 0 |
| 84 | 0 | 0 | 0 | 0 | 0 | 0 | 0 | 0 | 0 | 0 | 0 |
| 85 | 0 | 0 | 0 | 0 | 0 | 0 | 0 | 0 | 0 | 0 | 0 |
| 86 | 0 | 0 | 0 | 0 | 0 | 0 | 0 | 0 | 0 | 0 | 0 |
| 87 | 0 | 0 | 0 | 0 | 0 | 0 | 0 | 0 | 0 | 0 | 0 |
| 88 | 0 | 0 | 0 | 0 | 0 | 0 | 0 | 0 | 0 | 0 | 0 |
| 89 | 0 | 0 | 0 | 0 | 0 | 0 | 0 | 0 | 0 | 0 | 0 |
| 90 | 0 | 0 | 0 | 0 | 0 | 0 | 0 | 0 | 0 | 0 | 0 |
| 91 | 0 | 0 | 0 | 0 | 0 | 0 | 0 | 0 | 0 | 0 | 0 |

TABLE 6-continued

| Transition number | Smp1 | Smp2 | Smp3 | Smp4 | Smp5 | Smp6 | Smp7 | Smp8 | Smp9 | Smp10 | Smp11 |
|---|---|---|---|---|---|---|---|---|---|---|---|
| 92 | 0 | 0 | 0 | 0 | 0 | 0 | 0 | 0 | 0 | 0 | 0 |
| 93 | 0 | 0 | 0 | 0 | 0 | 0 | 0 | 0 | 0 | 0 | 0 |
| 94 | 0 | 0 | 0 | 0 | 0 | 0 | 0 | 0 | 0 | 0 | 0 |
| 95 | 0 | 0 | 0 | 0 | 0 | 0 | 0 | 0 | 0 | 0 | 0 |
| 96 | 0 | 0 | 0 | 0 | 0 | 0 | 0 | 0 | 0 | 0 | 0 |
| 97 | 0 | 0 | 0 | 0 | 0 | 0 | 0 | 0 | 1 | 0 | 0 |
| 98 | 0 | 0 | 0 | 0 | 0 | 0 | 0 | 0 | 1 | 0 | 0 |
| 99 | 0 | 0 | 0 | 0 | 0 | 0 | 0 | 0 | 1 | 0 | 0 |
| 100 | 0 | 0 | 0 | 0 | 0 | 0 | 0 | 0 | 1 | 0 | 0 |
| 101 | 0 | 0 | 0 | 0 | 0 | 0 | 0 | 0 | 1 | 0 | 0 |
| 102 | 0 | 0 | 0 | 0 | 0 | 0 | 0 | 0 | 1 | 0 | 0 |
| 103 | 0 | 0 | 0 | 0 | 0 | 0 | 0 | 0 | 0 | 0 | 0 |
| 104 | 0 | 0 | 0 | 0 | 0 | 0 | 0 | 0 | 0 | 0 | 0 |
| 105 | 0 | 0 | 0 | 0 | 0 | 0 | 0 | 0 | 0 | 0 | 0 |
| 106 | 0 | 0 | 0 | 0 | 0 | 0 | 0 | 0 | 1 | 0 | 0 |
| 107 | 0 | 0 | 0 | 0 | 0 | 0 | 0 | 0 | 1 | 0 | 0 |
| 108 | 0 | 0 | 0 | 0 | 0 | 0 | 0 | 0 | 1 | 0 | 0 |
| 109 | 0 | 0 | 0 | 0 | 0 | 0 | 0 | 0 | 0 | 0 | 0 |
| 110 | 0 | 0 | 0 | 0 | 0 | 0 | 0 | 0 | 0 | 0 | 0 |
| 111 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 |
| 113 | 0 | 0 | 0 | 0 | 0 | 0 | 0 | 0 | 0 | 0 | 0 |
| 114 | 0 | 0 | 0 | 0 | 0 | 0 | 0 | 0 | 0 | 0 | 0 |
| 115 | 0 | 0 | 0 | 0 | 0 | 0 | 0 | 0 | 0 | 0 | 0 |
| 116 | 0 | 0 | 0 | 0 | 0 | 0 | 0 | 0 | 0 | 0 | 0 |
| 117 | 0 | 0 | 0 | 0 | 0 | 0 | 0 | 0 | 0 | 0 | 0 |
| 118 | 0 | 0 | 0 | 0 | 0 | 0 | 0 | 0 | 0 | 1 | 0 |
| 119 | 0 | 0 | 0 | 0 | 0 | 0 | 0 | 0 | 0 | 1 | 0 |
| 120 | 0 | 1 | 0 | 0 | 0 | 0 | 0 | 0 | 0 | 0 | 0 |
| 121 | 0 | 0 | 0 | 0 | 0 | 0 | 1 | 0 | 0 | 0 | 0 |
| 122 | 0 | 0 | 0 | 0 | 0 | 0 | 0 | 0 | 0 | 0 | 0 |
| 123 | 0 | 0 | 0 | 0 | 0 | 0 | 0 | 0 | 0 | 0 | 0 |
| 124 | 0 | 0 | 0 | 0 | 0 | 0 | 0 | 0 | 0 | 0 | 0 |
| 125 | 1 | 0 | 1 | 0 | 0 | 1 | 0 | 0 | 0 | 0 | 0 |
| 126 | 1 | 0 | 1 | 0 | 0 | 1 | 0 | 0 | 0 | 0 | 0 |
| 127 | 0 | 0 | 0 | 0 | 0 | 0 | 0 | 0 | 0 | 0 | 0 |
| 128 | 0 | 0 | 0 | 0 | 0 | 0 | 0 | 0 | 0 | 0 | 0 |
| 129 | 0 | 0 | 0 | 0 | 0 | 0 | 0 | 0 | 0 | 0 | 0 |
| 130 | 0 | 0 | 0 | 0 | 0 | 0 | 0 | 0 | 0 | 0 | 0 |
| 131 | 0 | 0 | 0 | 0 | 0 | 1 | 0 | 0 | 0 | 0 | 0 |
| 132 | 0 | 0 | 0 | 0 | 0 | 0 | 0 | 0 | 0 | 0 | 0 |
| 133 | 0 | 0 | 0 | 0 | 0 | 0 | 0 | 0 | 0 | 0 | 0 |
| 134 | 0 | 0 | 0 | 0 | 0 | 0 | 0 | 0 | 0 | 0 | 0 |
| 135 | 0 | 0 | 0 | 0 | 0 | 0 | 0 | 0 | 0 | 0 | 0 |
| 136 | 0 | 0 | 0 | 0 | 0 | 1 | 0 | 0 | 0 | 0 | 0 |
| 137 | 0 | 0 | 0 | 0 | 0 | 1 | 1 | 0 | 0 | 0 | 0 |
| 138 | 0 | 0 | 0 | 0 | 0 | 1 | 0 | 0 | 0 | 0 | 0 |
| 139 | 0 | 0 | 0 | 0 | 0 | 0 | 0 | 0 | 0 | 0 | 0 |
| 140 | 0 | 0 | 0 | 0 | 0 | 0 | 0 | 0 | 0 | 0 | 0 |
| 141 | 0 | 0 | 0 | 0 | 0 | 0 | 0 | 0 | 0 | 0 | 0 |
| 142 | 0 | 0 | 0 | 0 | 0 | 0 | 0 | 0 | 0 | 0 | 0 |
| 143 | 0 | 0 | 0 | 0 | 0 | 0 | 0 | 0 | 0 | 0 | 0 |
| 144 | 0 | 0 | 0 | 0 | 0 | 0 | 0 | 0 | 0 | 0 | 0 |
| 145 | 0 | 0 | 0 | 0 | 0 | 1 | 0 | 0 | 0 | 0 | 0 |
| 146 | 0 | 0 | 0 | 0 | 0 | 1 | 0 | 0 | 0 | 0 | 0 |
| 147 | 0 | 0 | 0 | 0 | 0 | 1 | 0 | 0 | 0 | 0 | 0 |
| 148 | 0 | 0 | 0 | 0 | 0 | 0 | 0 | 0 | 0 | 0 | 0 |
| 149 | 0 | 0 | 0 | 0 | 0 | 0 | 0 | 0 | 0 | 0 | 0 |
| 150 | 0 | 0 | 0 | 0 | 0 | 0 | 0 | 0 | 0 | 0 | 0 |
| 151 | 0 | 0 | 1 | 0 | 0 | 0 | 0 | 0 | 0 | 0 | 0 |
| 152 | 0 | 0 | 1 | 0 | 0 | 0 | 0 | 0 | 0 | 0 | 0 |
| 153 | 0 | 0 | 1 | 0 | 0 | 0 | 0 | 0 | 0 | 0 | 0 |

Samples Smp1, Smp2, Smp4, Smp5, Smp7 and Smp9 do not have any peptide characteristic of resistance of the Van type. The bacteria present in samples Smp1, Smp2, Smp4, Smp5, Smp7 and Smp9 may be sensitive to the glycopeptides of the vancomycin or teicoplanin type.

Samples Smp3, Smp10 and Smp11 comprise at least one peptide characteristic of VanA. The bacteria present in samples Smp3, Smp10 and Smp11 therefore express the ligase VanA, which endows them with resistance to vancomycin and to teicoplanin.

Sample Smp6 comprises at least one peptide characteristic of VanG. The bacterium present in sample Smp6 therefore expresses the ligase VanG, which endows it with resistance to vancomycin.

Sample Smp8 comprises at least one peptide characteristic of VanD. The bacterium present in sample Smp8 therefore expresses the ligase VanD, which endows it with resistance to vancomycin and to teicoplanin.

Thus, advantageously, several mechanisms of resistance to glycopeptides are investigated simultaneously. Particularly advantageously, a mechanism of inducible resistance, such as the mechanism of resistance linked to expression of VanA, is detected without an induction phase during culture of the microorganism. This method therefore makes it possible to investigate the mechanisms of resistance to glycopeptides without a priori on their possible existence.

EXAMPLE 9

Identification of Resistance to Glycopeptides, with Induction, of Type VanA, VanB, VanD, VanE and VanG Samples Smp1 to Smp11 are identified according to one of the methods described in examples 1 to 6. Identification of the species is reported in TABLE 7.

TABLE 7

| Name | Species |
|---|---|
| Smp12 | *E. faecalis* |
| Smp13 | *E. faecalis* |
| Smp14 | *E. faecalis* |
| Smp15 | *E. faecalis* |
| Smp16 | *E. faecalis* |
| Smp17 | *E. faecium* |
| Smp18 | *E. faecium* |
| Smp19 | *E. faecalis* |
| Smp20 | *E. faecium* |

Samples Smp12 to Smp20 correspond to a species that may comprise a mechanism of resistance of the Van type. The following method is then employed for investigating such a mechanism.

The microorganism colony is obtained according to example 3 and then treated according to example 7 and analyzed according to example 8.

The areas obtained for each of the transitions and for each of the microorganisms studied were measured. When the area of a transition is greater than or equal to the positivity threshold described in TABLE 5, detection of the transition is regarded as positive and is marked "1" in TABLE 8. When the area of a transition is below the positivity threshold described in TABLE 5, detection of the transition is regarded as negative and is marked "0" in TABLE 8. When the 3 transitions of one and the same peptide are marked "1", detection of the peptide is regarded as positive. One particular case is an exception to this rule. The peptide corresponding to the transitions numbered 49, 50 and 51 has a transition of very low intensity. In this precise case, when the transitions 49 and 50 are marked "1", detection of this peptide will be regarded as positive.

TABLE 8

| Transition number | Smp12 | Smp13 | Smp14 | Smp15 | Smp16 | Smp17 | Smp18 | Smp19 | Smp20 |
|---|---|---|---|---|---|---|---|---|---|
| 1 | 0 | 0 | 0 | 0 | 0 | 0 | 0 | 0 | 0 |
| 2 | 0 | 0 | 0 | 0 | 0 | 0 | 0 | 0 | 0 |
| 3 | 0 | 0 | 0 | 0 | 0 | 0 | 0 | 1 | 0 |
| 4 | 0 | 0 | 0 | 0 | 0 | 0 | 0 | 0 | 0 |
| 5 | 0 | 0 | 0 | 0 | 0 | 0 | 0 | 0 | 1 |
| 6 | 0 | 0 | 0 | 0 | 0 | 0 | 0 | 0 | 0 |
| 7 | 0 | 0 | 0 | 0 | 0 | 0 | 0 | 1 | 1 |
| 8 | 0 | 0 | 0 | 0 | 0 | 0 | 0 | 1 | 1 |
| 9 | 0 | 0 | 0 | 0 | 0 | 0 | 0 | 1 | 1 |
| 10 | 0 | 0 | 0 | 0 | 0 | 0 | 0 | 1 | 1 |
| 11 | 0 | 0 | 0 | 0 | 0 | 0 | 0 | 1 | 1 |
| 12 | 0 | 0 | 0 | 0 | 0 | 0 | 0 | 1 | 1 |
| 13 | 0 | 0 | 0 | 0 | 0 | 0 | 0 | 1 | 1 |
| 14 | 0 | 0 | 0 | 0 | 0 | 0 | 0 | 1 | 1 |
| 15 | 0 | 0 | 0 | 0 | 0 | 0 | 0 | 1 | 1 |
| 16 | 0 | 0 | 0 | 0 | 0 | 0 | 0 | 0 | 0 |
| 17 | 0 | 0 | 0 | 0 | 0 | 0 | 0 | 0 | 0 |
| 18 | 0 | 0 | 0 | 0 | 0 | 0 | 0 | 0 | 0 |
| 19 | 0 | 0 | 0 | 0 | 0 | 0 | 0 | 1 | 1 |
| 20 | 0 | 0 | 0 | 0 | 0 | 0 | 0 | 1 | 1 |
| 21 | 0 | 0 | 0 | 0 | 0 | 0 | 0 | 1 | 1 |
| 22 | 0 | 0 | 0 | 0 | 0 | 0 | 0 | 1 | 1 |
| 23 | 0 | 0 | 0 | 0 | 0 | 0 | 0 | 1 | 1 |
| 24 | 0 | 0 | 0 | 0 | 0 | 0 | 0 | 1 | 1 |
| 25 | 0 | 0 | 0 | 1 | 0 | 0 | 0 | 1 | 0 |
| 26 | 0 | 0 | 0 | 0 | 0 | 0 | 0 | 1 | 0 |
| 27 | 0 | 0 | 0 | 0 | 0 | 0 | 0 | 1 | 0 |
| 28 | 0 | 0 | 0 | 0 | 0 | 0 | 0 | 1 | 1 |
| 29 | 0 | 0 | 0 | 0 | 0 | 0 | 0 | 1 | 1 |
| 30 | 0 | 0 | 0 | 0 | 0 | 0 | 0 | 1 | 1 |
| 31 | 0 | 0 | 0 | 0 | 0 | 0 | 0 | 1 | 1 |
| 32 | 0 | 0 | 0 | 0 | 0 | 0 | 0 | 1 | 0 |
| 33 | 0 | 0 | 0 | 0 | 0 | 0 | 0 | 1 | 0 |
| 34 | 0 | 0 | 0 | 0 | 0 | 0 | 0 | 1 | 1 |
| 35 | 0 | 0 | 0 | 0 | 0 | 0 | 0 | 1 | 1 |
| 36 | 0 | 0 | 0 | 0 | 0 | 0 | 0 | 1 | 1 |
| 37 | 0 | 1 | 1 | 0 | 0 | 0 | 0 | 0 | 0 |
| 38 | 0 | 1 | 1 | 0 | 0 | 0 | 0 | 0 | 0 |
| 39 | 0 | 1 | 1 | 0 | 0 | 0 | 1 | 0 | 0 |
| 40 | 0 | 1 | 1 | 0 | 0 | 0 | 1 | 0 | 0 |
| 41 | 0 | 1 | 1 | 0 | 0 | 0 | 0 | 0 | 0 |

TABLE 8-continued

| Transition number | Smp12 | Smp13 | Smp14 | Smp15 | Smp16 | Smp17 | Smp18 | Smp19 | Smp20 |
|---|---|---|---|---|---|---|---|---|---|
| 42 | 0 | 1 | 1 | 0 | 0 | 0 | 0 | 0 | 0 |
| 43 | 0 | 0 | 0 | 0 | 0 | 0 | 0 | 0 | 0 |
| 44 | 0 | 0 | 0 | 0 | 0 | 0 | 0 | 0 | 0 |
| 45 | 0 | 0 | 0 | 0 | 0 | 0 | 0 | 0 | 0 |
| 46 | 0 | 1 | 1 | 0 | 0 | 1 | 1 | 0 | 0 |
| 47 | 0 | 1 | 1 | 0 | 0 | 0 | 1 | 0 | 0 |
| 48 | 0 | 1 | 1 | 0 | 0 | 0 | 1 | 0 | 0 |
| 49 | 0 | 1 | 1 | 0 | 0 | 0 | 0 | 0 | 0 |
| 50 | 0 | 1 | 1 | 0 | 0 | 0 | 0 | 0 | 0 |
| 51 | 0 | 0 | 0 | 0 | 0 | 0 | 0 | 0 | 0 |
| 52 | 0 | 0 | 0 | 0 | 0 | 0 | 0 | 0 | 0 |
| 53 | 0 | 0 | 0 | 0 | 0 | 0 | 0 | 0 | 0 |
| 54 | 0 | 1 | 0 | 0 | 0 | 0 | 0 | 0 | 0 |
| 55 | 0 | 0 | 0 | 0 | 0 | 0 | 0 | 0 | 0 |
| 56 | 0 | 0 | 0 | 0 | 0 | 0 | 0 | 0 | 0 |
| 57 | 0 | 0 | 0 | 0 | 0 | 0 | 0 | 0 | 0 |
| 58 | 0 | 0 | 0 | 0 | 0 | 0 | 0 | 0 | 0 |
| 59 | 0 | 0 | 0 | 0 | 0 | 0 | 0 | 0 | 0 |
| 60 | 0 | 0 | 0 | 0 | 0 | 0 | 0 | 0 | 0 |
| 61 | 0 | 0 | 0 | 0 | 0 | 0 | 0 | 0 | 0 |
| 62 | 0 | 0 | 0 | 0 | 0 | 0 | 0 | 0 | 0 |
| 63 | 0 | 0 | 0 | 0 | 0 | 0 | 0 | 0 | 0 |
| 64 | 0 | 0 | 0 | 0 | 0 | 0 | 0 | 0 | 0 |
| 65 | 0 | 0 | 0 | 0 | 0 | 0 | 0 | 0 | 0 |
| 66 | 0 | 0 | 0 | 0 | 0 | 0 | 0 | 0 | 0 |
| 67 | 0 | 0 | 0 | 0 | 0 | 0 | 0 | 0 | 0 |
| 68 | 0 | 0 | 0 | 0 | 0 | 0 | 0 | 0 | 0 |
| 69 | 0 | 0 | 0 | 0 | 0 | 0 | 0 | 0 | 0 |
| 70 | 0 | 0 | 0 | 0 | 0 | 0 | 0 | 0 | 0 |
| 71 | 0 | 0 | 0 | 0 | 0 | 0 | 0 | 0 | 0 |
| 72 | 0 | 0 | 0 | 0 | 0 | 0 | 0 | 0 | 0 |
| 73 | 0 | 0 | 0 | 0 | 0 | 1 | 0 | 0 | 0 |
| 74 | 0 | 0 | 0 | 0 | 0 | 0 | 0 | 0 | 0 |
| 75 | 0 | 0 | 0 | 0 | 0 | 0 | 0 | 0 | 0 |
| 76 | 0 | 0 | 0 | 0 | 0 | 0 | 0 | 0 | 0 |
| 77 | 0 | 0 | 0 | 0 | 0 | 0 | 0 | 0 | 0 |
| 78 | 0 | 0 | 0 | 0 | 0 | 0 | 0 | 0 | 0 |
| 79 | 0 | 0 | 0 | 0 | 0 | 0 | 0 | 0 | 0 |
| 80 | 0 | 0 | 0 | 0 | 0 | 0 | 0 | 0 | 0 |
| 81 | 0 | 0 | 0 | 0 | 0 | 0 | 0 | 0 | 0 |
| 82 | 0 | 0 | 0 | 0 | 0 | 0 | 0 | 0 | 0 |
| 83 | 0 | 0 | 0 | 0 | 0 | 0 | 0 | 0 | 0 |
| 84 | 0 | 0 | 0 | 0 | 0 | 0 | 0 | 0 | 0 |
| 85 | 0 | 0 | 0 | 0 | 0 | 0 | 0 | 0 | 0 |
| 86 | 0 | 0 | 0 | 0 | 0 | 0 | 0 | 0 | 0 |
| 87 | 0 | 0 | 0 | 0 | 0 | 0 | 0 | 0 | 0 |
| 88 | 0 | 0 | 0 | 0 | 0 | 0 | 0 | 0 | 0 |
| 89 | 0 | 0 | 0 | 0 | 0 | 0 | 0 | 0 | 0 |
| 90 | 0 | 0 | 0 | 0 | 0 | 0 | 0 | 0 | 0 |
| 91 | 0 | 0 | 0 | 0 | 0 | 0 | 0 | 0 | 0 |
| 92 | 0 | 0 | 0 | 0 | 0 | 0 | 0 | 0 | 0 |
| 93 | 0 | 0 | 0 | 0 | 0 | 0 | 0 | 0 | 0 |
| 94 | 0 | 0 | 0 | 0 | 0 | 0 | 0 | 0 | 0 |
| 95 | 0 | 0 | 0 | 0 | 0 | 0 | 0 | 0 | 0 |
| 96 | 0 | 0 | 0 | 0 | 0 | 0 | 0 | 0 | 0 |
| 97 | 0 | 0 | 0 | 0 | 0 | 1 | 0 | 0 | 0 |
| 98 | 0 | 0 | 0 | 0 | 0 | 1 | 0 | 0 | 0 |
| 99 | 0 | 0 | 0 | 0 | 0 | 1 | 0 | 0 | 0 |
| 100 | 0 | 0 | 0 | 0 | 0 | 1 | 0 | 0 | 0 |
| 101 | 0 | 0 | 0 | 0 | 0 | 1 | 0 | 0 | 0 |
| 102 | 0 | 0 | 0 | 0 | 0 | 1 | 0 | 0 | 1 |
| 103 | 0 | 0 | 0 | 0 | 0 | 0 | 0 | 0 | 0 |
| 104 | 0 | 0 | 0 | 0 | 0 | 0 | 0 | 0 | 0 |
| 105 | 0 | 0 | 0 | 0 | 0 | 0 | 0 | 0 | 0 |
| 106 | 0 | 0 | 0 | 0 | 0 | 1 | 0 | 0 | 0 |
| 107 | 0 | 0 | 0 | 0 | 0 | 1 | 0 | 0 | 0 |
| 108 | 0 | 0 | 0 | 0 | 0 | 1 | 0 | 0 | 0 |
| 109 | 0 | 0 | 0 | 0 | 0 | 0 | 0 | 0 | 0 |
| 110 | 0 | 0 | 0 | 0 | 1 | 0 | 0 | 0 | 0 |
| 111 | 0 | 0 | 0 | 0 | 0 | 0 | 0 | 0 | 0 |
| 112 | 0 | 0 | 0 | 0 | 0 | 0 | 0 | 0 | 0 |
| 113 | 0 | 0 | 0 | 0 | 0 | 0 | 0 | 0 | 0 |
| 114 | 0 | 0 | 0 | 0 | 0 | 0 | 0 | 0 | 0 |

TABLE 8-continued

| Transition number | Smp12 | Smp13 | Smp14 | Smp15 | Smp16 | Smp17 | Smp18 | Smp19 | Smp20 |
|---|---|---|---|---|---|---|---|---|---|
| 115 | 0 | 0 | 0 | 0 | 0 | 0 | 0 | 0 | 0 |
| 116 | 0 | 0 | 0 | 0 | 0 | 0 | 0 | 0 | 0 |
| 117 | 0 | 0 | 0 | 0 | 0 | 0 | 0 | 0 | 0 |
| 118 | 0 | 0 | 0 | 0 | 0 | 0 | 0 | 0 | 0 |
| 119 | 0 | 0 | 0 | 0 | 0 | 0 | 0 | 0 | 0 |
| 120 | 0 | 0 | 0 | 0 | 0 | 0 | 0 | 0 | 0 |
| 121 | 0 | 0 | 0 | 0 | 1 | 0 | 0 | 0 | 0 |
| 122 | 0 | 0 | 0 | 0 | 1 | 0 | 0 | 0 | 0 |
| 123 | 0 | 0 | 0 | 0 | 1 | 0 | 0 | 0 | 0 |
| 124 | 0 | 0 | 0 | 0 | 0 | 0 | 0 | 0 | 0 |
| 125 | 0 | 0 | 1 | 0 | 1 | 0 | 0 | 0 | 0 |
| 126 | 0 | 0 | 1 | 0 | 1 | 0 | 0 | 0 | 0 |
| 127 | 0 | 0 | 0 | 0 | 0 | 1 | 0 | 0 | 0 |
| 128 | 0 | 0 | 0 | 0 | 0 | 1 | 0 | 0 | 0 |
| 129 | 0 | 0 | 0 | 0 | 0 | 0 | 0 | 0 | 0 |
| 130 | 0 | 0 | 0 | 1 | 0 | 0 | 0 | 0 | 0 |
| 131 | 0 | 0 | 0 | 1 | 0 | 0 | 0 | 0 | 0 |
| 132 | 0 | 0 | 0 | 1 | 0 | 0 | 0 | 0 | 0 |
| 133 | 0 | 0 | 0 | 1 | 0 | 0 | 0 | 0 | 0 |
| 134 | 0 | 0 | 0 | 1 | 0 | 0 | 0 | 0 | 0 |
| 135 | 0 | 0 | 0 | 1 | 0 | 0 | 0 | 0 | 0 |
| 136 | 0 | 0 | 0 | 1 | 0 | 0 | 0 | 0 | 0 |
| 137 | 0 | 0 | 0 | 1 | 0 | 0 | 0 | 0 | 0 |
| 138 | 0 | 0 | 0 | 1 | 0 | 0 | 0 | 0 | 0 |
| 139 | 0 | 0 | 0 | 1 | 0 | 0 | 0 | 0 | 0 |
| 140 | 0 | 0 | 0 | 1 | 0 | 0 | 0 | 0 | 0 |
| 141 | 0 | 0 | 0 | 1 | 0 | 0 | 0 | 0 | 0 |
| 142 | 0 | 0 | 0 | 0 | 0 | 0 | 0 | 0 | 0 |
| 143 | 0 | 0 | 0 | 0 | 0 | 0 | 0 | 0 | 0 |
| 144 | 0 | 0 | 0 | 0 | 0 | 0 | 0 | 0 | 0 |
| 145 | 0 | 0 | 0 | 1 | 0 | 0 | 0 | 0 | 0 |
| 146 | 0 | 0 | 0 | 1 | 0 | 0 | 0 | 0 | 0 |
| 147 | 0 | 0 | 0 | 1 | 0 | 0 | 0 | 0 | 0 |
| 148 | 0 | 0 | 0 | 0 | 0 | 0 | 0 | 0 | 0 |
| 149 | 0 | 0 | 0 | 0 | 0 | 0 | 0 | 0 | 0 |
| 150 | 0 | 0 | 0 | 0 | 0 | 0 | 0 | 0 | 0 |
| 151 | 0 | 0 | 0 | 1 | 0 | 0 | 0 | 0 | 0 |
| 152 | 0 | 0 | 0 | 1 | 0 | 0 | 0 | 0 | 0 |
| 153 | 0 | 0 | 0 | 1 | 0 | 0 | 0 | 0 | 0 |

Sample Smp12 does not have any peptide characteristic of resistance of the Van type. The bacterium present in sample Smp12 may be sensitive to the glycopeptides of the vancomycin or teicoplanin type.

Samples Smp19 and Smp20 comprise at least one peptide characteristic of VanA. The bacteria present in samples Smp19 and Smp20 therefore express the ligase VanA, which endows them with resistance to vancomycin and to teicoplanin.

Samples Smp13, Smp14 and Smp18 comprise at least one peptide characteristic of VanB. The bacteria present in samples Smp13, Smp14 and Smp18 therefore express the ligase VanB, which endows them with resistance to vancomycin.

Sample Smp15 comprises at least one peptide characteristic of VanG. The bacterium present in sample Smp15 expresses the ligase VanG, which endows it with resistance to vancomycin.

Sample Smp16 comprises at least one peptide characteristic of VanE. The bacterium present in sample Smp16 expresses the ligase VanE, which endows it with resistance to vancomycin.

Sample Smp17 comprises at least one peptide characteristic of VanD. The bacterium present in sample Smp17 expresses the ligase VanD, which endows it with resistance to vancomycin and to teicoplanin.

Thus, advantageously, several mechanisms of resistance to glycopeptides may be investigated simultaneously.

EXAMPLE 10

Obtaining Digested Proteins from Microorganisms

The following protocol is carried out in 16 steps:

1. Taking a sample of a microorganism colony, obtained according to example 8 and suspended in 100 µl of a solution of ammonium bicarbonate, 50 mM, pH=8.0 in a tube containing glass beads with diameter from 0.05 mm to 2 mm
2. Addition of dithiothreitol (DTT) to obtain a final concentration of 5 mM.
3. Reduction for 5 minutes at 95° C. on a Hielscher probe (instrument settings: amplitude: 100, cycle: 1)
4. Cooling of the tubes to room temperature.
5. Addition of iodoacetamide to obtain a final concentration of 12.5 mM.
6. Alkylation for 5 minutes at room temperature and away from the light.
7. Addition of 1 µg of trypsin.
8. Digestion at 50° C. for 15 minutes
9. Addition of formic acid until the pH is below 4 to stop the reaction.
10. Centrifugation for 5 minutes at 15 000 g, the supernatant is recovered and made up to 1 mL with water/formic acid 0.5% (v/v)
11. Equilibration of the Waters Oasis HLB columns with 1 ml of methanol and then 1 ml $H_2O$/formic acid 0.1% (v/v)

12. Deposition of the sample, which flows by gravity
13. Washing with 1 ml $H_2O$/formic acid 0.1% (v/v)
14. Elution with 1 ml of a mixture of 80% methanol and 20% water/formic acid 0.1% (v/v)
15. The eluate is evaporated with an evaporator of the SpeedVac® SPD2010 type (Thermo Electron Corporation, Waltham, Mass., United States of America), for 2 hours, in order to obtain a volume of about 100 µl.
16. The eluate is then taken up in a solution of water/formic acid 0.5% (v/v), sufficient quantity (Q.S.) for 150 µl

EXAMPLE 11

Identification of Resistance to Glycopeptides, without induction, of Type VanA Samples Smp21 and Smp22 are identified according to one of the methods described in examples 1 to 6. Identification of the species is reported in TABLE 9.

TABLE 9

| Name | Species |
|---|---|
| Smp21 | *E. faecalis* |
| Smp22 | *E. faecalis* |

Samples Smp21 and Smp22 correspond to the species *Enterococcus faecalis*, which may comprise a mechanism of resistance of the Van type. The following method is then employed for investigating such a mechanism.

Each sample is treated according to example 10 and analyzed according to example 8 apart from the elements mentioned below.

The transitions mentioned in TABLE 3 are detected using the parameters shown in TABLES 10 and 11.

TABLE 10

| Transition number | Retention time | (m/z) filtered in Q1 | (m/z) filtered in Q3 | Collision energy (eV) |
|---|---|---|---|---|
| 1 | 8.75 | 554.79 | 601.32 | 29 |
| 2 | 8.75 | 554.79 | 730.36 | 29 |
| 3 | 8.75 | 554.79 | 858.42 | 29 |
| 4 | 19.71 | 385.28 | 444.32 | 22 |
| 5 | 19.71 | 385.28 | 543.39 | 22 |
| 6 | 19.71 | 385.28 | 656.47 | 22 |
| 7 | 17.91 | 448.75 | 492.29 | 25 |
| 8 | 17.91 | 448.75 | 655.36 | 25 |
| 9 | 17.91 | 448.75 | 783.41 | 25 |
| 10 | 13.32 | 399.24 | 552.3 | 23 |
| 11 | 13.32 | 399.24 | 529.37 | 23 |
| 12 | 13.32 | 399.24 | 666.43 | 23 |
| 13 | 23.29 | 786.42 | 742.41 | 32 |
| 14 | 23.29 | 786.42 | 855.49 | 31 |
| 15 | 23.29 | 786.42 | 926.53 | 34 |
| 16 | 22.44 | 751.41 | 1146.63 | 38 |
| 17 | 22.44 | 751.41 | 974.55 | 38 |
| 18 | 22.44 | 751.41 | 1075.59 | 38 |
| 19 | 15.89 | 572.32 | 630.36 | 25 |
| 20 | 15.89 | 572.32 | 743.44 | 26 |
| 21 | 15.89 | 572.32 | 872.48 | 25 |
| 22 | 10.67 | 384.7 | 537.3 | 20.5 |
| 23 | 10.67 | 384.7 | 624.34 | 18.5 |
| 24 | 10.67 | 384.7 | 681.36 | 19.5 |
| 25 | 15.29 | 447.77 | 430.3 | 25 |
| 26 | 15.29 | 447.77 | 593.37 | 25 |
| 27 | 15.29 | 447.77 | 694.41 | 25 |
| 28 | 16.64 | 597.78 | 702.35 | 29 |
| 29 | 16.64 | 597.78 | 849.42 | 29 |

TABLE 10-continued

| Transition number | Retention time | (m/z) filtered in Q1 | (m/z) filtered in Q3 | Collision energy (eV) |
|---|---|---|---|---|
| 30 | 16.64 | 597.78 | 980.46 | 27 |
| 31 | 18.52 | 826.89 | 646.35 | 41 |
| 32 | 18.52 | 826.89 | 809.42 | 41 |
| 33 | 18.52 | 826.89 | 924.44 | 41 |
| 34 | 19.2 | 598.83 | 807.5 | 31 |
| 35 | 19.2 | 598.83 | 904.55 | 22 |
| 36 | 19.2 | 598.83 | 452.78 | 25 |
| 37 | 15.89 | 595.81 | 694.41 | 33 |
| 38 | 15.89 | 595.81 | 416.24 | 35 |
| 39 | 15.89 | 595.81 | 464.77 | 28 |
| 40 | 19.1 | 598.35 | 650.4 | 29 |
| 41 | 19.1 | 598.35 | 797.47 | 28 |
| 42 | 19.1 | 598.35 | 868.5 | 28 |
| 43 | 4.97 | 562.27 | 616.29 | 30 |
| 44 | 4.97 | 562.27 | 745.34 | 30 |
| 45 | 4.97 | 562.27 | 873.39 | 30 |
| 46 | 12.85 | 415.24 | 492.29 | 23 |
| 47 | 12.85 | 415.24 | 629.35 | 23 |
| 48 | 12.85 | 415.24 | 716.38 | 23 |
| 49 | 17.9 | 454.78 | 637.39 | 25 |
| 50 | 17.9 | 454.78 | 708.43 | 25 |
| 51 | 17.9 | 454.78 | 821.51 | 25 |
| 52 | 14.32 | 449.76 | 522.3 | 25 |
| 53 | 14.32 | 449.76 | 621.37 | 25 |
| 54 | 14.32 | 449.76 | 660.41 | 25 |
| 55 | 1.53 | 338.19 | 319.2 | 20 |
| 56 | 1.53 | 338.19 | 448.24 | 20 |
| 57 | 1.53 | 338.19 | 576.3 | 20 |
| 58 | 14.16 | 510.78 | 451.27 | 24 |
| 59 | 14.16 | 510.78 | 564.35 | 25 |
| 60 | 14.16 | 510.78 | 763.45 | 27 |
| 61 | 19.45 | 744.72 | 845.39 | 43 |
| 62 | 19.45 | 744.72 | 789.37 | 41 |
| 63 | 19.45 | 744.72 | 917.47 | 40 |
| 64 | 22.56 | 717.43 | 611.35 | 30 |
| 65 | 22.56 | 478.62 | 611.35 | 16 |
| 66 | 22.56 | 478.62 | 407.9 | 19 |
| 67 | 19.53 | 655.98 | 559.34 | 34 |
| 68 | 19.53 | 655.98 | 763.43 | 27 |
| 69 | 19.53 | 655.98 | 891.49 | 25 |
| 70 | 12.98 | 579.26 | 641.33 | 31 |
| 71 | 12.98 | 579.26 | 827.4 | 29 |
| 72 | 12.98 | 579.26 | 928.45 | 27 |
| 73 | 16.92 | 457.77 | 416.26 | 22 |
| 74 | 16.92 | 457.77 | 517.31 | 21 |
| 75 | 16.92 | 457.77 | 687.41 | 22 |
| 76 | 27.6 | 728.74 | 788.89 | 29 |
| 77 | 27.6 | 728.74 | 845.51 | 31 |
| 78 | 27.6 | 728.74 | 1008.57 | 31 |
| 79 | 26.39 | 803.11 | 1028.61 | 35 |
| 80 | 26.39 | 803.11 | 799.5 | 30 |
| 81 | 26.39 | 803.11 | 957.57 | 35 |
| 82 | 11.46 | 597.28 | 522.18 | 26 |
| 83 | 11.46 | 597.28 | 672.37 | 33 |
| 84 | 11.46 | 597.28 | 901.44 | 26 |
| 85 | 26.58 | 822.81 | 604.87 | 30 |
| 86 | 26.58 | 822.81 | 688.91 | 26 |
| 87 | 26.58 | 822.81 | 998.59 | 39 |
| 88 | 19.29 | 754.93 | 598.33 | 30 |
| 89 | 19.29 | 754.93 | 817.43 | 45 |
| 90 | 19.29 | 754.93 | 1027.57 | 38 |
| 91 | 18.18 | 560.29 | 476.27 | 30 |
| 92 | 18.18 | 560.29 | 589.36 | 30 |
| 93 | 18.18 | 560.29 | 775.43 | 30 |
| 94 | 13.88 | 411.74 | 305.18 | 23 |
| 95 | 13.88 | 411.74 | 531.35 | 23 |
| 96 | 13.88 | 411.74 | 659.41 | 23 |
| 97 | 9.97 | 423.23 | 458.31 | 25 |
| 98 | 9.97 | 423.23 | 572.35 | 23 |
| 99 | 9.97 | 423.23 | 701.39 | 21 |
| 100 | 19.92 | 388.74 | 435.27 | 19 |
| 101 | 19.92 | 388.74 | 548.36 | 17 |
| 102 | 19.92 | 388.74 | 663.38 | 19 |
| 103 | 5.57 | 540.28 | 373.21 | 35 |
| 104 | 5.57 | 540.28 | 829.41 | 26 |
| 105 | 5.57 | 540.28 | 483.74 | 29 |

TABLE 10-continued

| Transition number | Retention time | (m/z) filtered in Q1 | (m/z) filtered in Q3 | Collision energy (eV) |
|---|---|---|---|---|
| 106 | 10.45 | 441.72 | 564.31 | 23 |
| 107 | 10.45 | 441.72 | 651.35 | 22 |
| 108 | 10.45 | 441.72 | 738.38 | 21 |
| 109 | 4.52 | 367.19 | 434.22 | 21 |
| 110 | 4.52 | 367.19 | 549.25 | 17 |
| 111 | 4.52 | 367.19 | 662.34 | 18 |
| 112 | 21.88 | 803.84 | 1100.48 | 41 |
| 113 | 21.88 | 803.84 | 730.31 | 38 |
| 114 | 21.88 | 803.84 | 613.27 | 46 |
| 115 | 20.03 | 728.9 | 550.3 | 39 |
| 116 | 20.03 | 728.9 | 834.47 | 41 |
| 117 | 20.03 | 728.9 | 962.53 | 39 |
| 118 | 16.81 | 672.3 | 769.35 | 26 |
| 119 | 16.81 | 672.3 | 882.44 | 26 |
| 120 | 16.81 | 672.3 | 969.47 | 26 |
| 121 | 13.59 | 351.23 | 444.32 | 18 |
| 122 | 13.59 | 351.23 | 543.39 | 16 |
| 123 | 13.59 | 351.23 | 614.42 | 17 |
| 124 | 14.51 | 503.27 | 720.4 | 28 |
| 125 | 14.51 | 503.27 | 817.45 | 19 |
| 126 | 14.51 | 503.27 | 409.23 | 20 |
| 127 | 22.39 | 722.92 | 428.29 | 37 |
| 128 | 22.39 | 722.92 | 854.53 | 37 |
| 129 | 22.39 | 722.92 | 955.58 | 37 |
| 130 | 12.77 | 434.23 | 565.33 | 24 |
| 131 | 12.77 | 434.23 | 739.4 | 21 |
| 132 | 12.77 | 434.23 | 796.42 | 22 |
| 133 | 12.41 | 477.73 | 553.27 | 27 |
| 134 | 12.41 | 477.73 | 713.3 | 26 |
| 135 | 12.41 | 477.73 | 770.33 | 24 |
| 136 | 7.63 | 388.2 | 476.24 | 22 |
| 137 | 7.63 | 388.2 | 547.27 | 19 |
| 138 | 7.63 | 388.2 | 662.3 | 19 |
| 139 | 12.85 | 375.7 | 343.21 | 22 |
| 140 | 12.85 | 375.7 | 474.25 | 22 |
| 141 | 12.85 | 375.7 | 637.31 | 22 |
| 142 | 20.72 | 403.74 | 397.28 | 23 |
| 143 | 20.72 | 403.74 | 560.34 | 23 |
| 144 | 20.72 | 403.74 | 659.41 | 23 |
| 145 | 19.66 | 542.34 | 600.37 | 23 |
| 146 | 19.66 | 542.34 | 671.41 | 25 |
| 147 | 19.66 | 542.34 | 871.52 | 23 |
| 148 | 22.14 | 939.94 | 1180.52 | 46 |
| 149 | 22.14 | 939.94 | 540.27 | 46 |
| 150 | 22.14 | 939.94 | 802.36 | 46 |
| 151 | 12.66 | 392.18 | 409.19 | 22 |
| 152 | 12.66 | 392.18 | 523.24 | 22 |
| 153 | 12.66 | 392.18 | 620.29 | 22 |

TABLE 11

| Transition number | Orifice potential | inlet potential before Q0 | Potential at collision cell outlet | Positivity threshold |
|---|---|---|---|---|
| 1 | 80 | 10 | 35 | 2000 |
| 2 | 80 | 10 | 35 | 2000 |
| 3 | 80 | 10 | 35 | 2000 |
| 4 | 80 | 10 | 35 | 600 |
| 5 | 80 | 10 | 35 | 2000 |
| 6 | 80 | 10 | 35 | 1000 |
| 7 | 80 | 10 | 35 | 2000 |
| 8 | 80 | 10 | 35 | 2000 |
| 9 | 80 | 10 | 35 | 2000 |
| 10 | 80 | 10 | 35 | 2000 |
| 11 | 80 | 10 | 35 | 2000 |
| 12 | 80 | 10 | 35 | 2000 |
| 13 | 120 | 10 | 18 | 2000 |
| 14 | 120 | 10 | 18 | 2000 |
| 15 | 120 | 10 | 18 | 2000 |
| 16 | 80 | 10 | 35 | 2000 |
| 17 | 80 | 10 | 35 | 2000 |

TABLE 11-continued

| Transition number | Orifice potential | inlet potential before Q0 | Potential at collision cell outlet | Positivity threshold |
|---|---|---|---|---|
| 18 | 80 | 10 | 35 | 2000 |
| 19 | 90 | 10 | 15 | 2000 |
| 20 | 90 | 10 | 15 | 2000 |
| 21 | 90 | 10 | 15 | 2000 |
| 22 | 85 | 10 | 24 | 2000 |
| 23 | 85 | 10 | 24 | 2000 |
| 24 | 85 | 10 | 24 | 2000 |
| 25 | 80 | 10 | 35 | 2000 |
| 26 | 80 | 10 | 35 | 2000 |
| 27 | 80 | 10 | 35 | 2000 |
| 28 | 100 | 10 | 17 | 2000 |
| 29 | 100 | 10 | 17 | 2000 |
| 30 | 100 | 10 | 17 | 2000 |
| 31 | 80 | 10 | 35 | 2000 |
| 32 | 80 | 10 | 35 | 2000 |
| 33 | 80 | 10 | 35 | 2000 |
| 34 | 105 | 10 | 20 | 2000 |
| 35 | 105 | 10 | 20 | 2000 |
| 36 | 105 | 10 | 20 | 2000 |
| 37 | 100 | 10 | 11 | 2000 |
| 38 | 100 | 10 | 16 | 2000 |
| 39 | 100 | 10 | 11 | 2000 |
| 40 | 90 | 10 | 16 | 2000 |
| 41 | 90 | 10 | 18 | 2000 |
| 42 | 90 | 10 | 22 | 2000 |
| 43 | 80 | 10 | 35 | 2000 |
| 44 | 80 | 10 | 35 | 2000 |
| 45 | 80 | 10 | 35 | 2000 |
| 46 | 80 | 10 | 35 | 2000 |
| 47 | 80 | 10 | 35 | 2000 |
| 48 | 80 | 10 | 35 | 2000 |
| 49 | 80 | 10 | 35 | 2000 |
| 50 | 80 | 10 | 35 | 2000 |
| 51 | 80 | 10 | 35 | 2000 |
| 52 | 80 | 10 | 35 | 2000 |
| 53 | 80 | 10 | 35 | 2000 |
| 54 | 80 | 10 | 35 | 2000 |
| 55 | 80 | 10 | 35 | 2000 |
| 56 | 80 | 10 | 35 | 2000 |
| 57 | 80 | 10 | 35 | 2000 |
| 58 | 75 | 12 | 11 | 2000 |
| 59 | 75 | 12 | 14 | 2000 |
| 60 | 75 | 12 | 18 | 2000 |
| 61 | 140 | 10 | 35 | 2000 |
| 62 | 140 | 10 | 35 | 2000 |
| 63 | 140 | 10 | 35 | 2000 |
| 64 | 120 | 10 | 35 | 2000 |
| 65 | 70 | 10 | 35 | 2000 |
| 66 | 70 | 10 | 35 | 2000 |
| 67 | 100 | 10 | 35 | 2000 |
| 68 | 100 | 10 | 35 | 2000 |
| 69 | 100 | 10 | 35 | 2000 |
| 70 | 80 | 12 | 15 | 3500 |
| 71 | 80 | 12 | 19 | 2500 |
| 72 | 80 | 12 | 22 | 4500 |
| 73 | 70 | 12 | 10 | 2000 |
| 74 | 70 | 12 | 13 | 2000 |
| 75 | 70 | 12 | 16 | 2000 |
| 76 | 120 | 10 | 35 | 2000 |
| 77 | 120 | 10 | 35 | 2000 |
| 78 | 120 | 10 | 35 | 2000 |
| 79 | 120 | 10 | 35 | 2000 |
| 80 | 120 | 10 | 35 | 2000 |
| 81 | 120 | 10 | 35 | 2000 |
| 82 | 85 | 12 | 13 | 2000 |
| 83 | 85 | 12 | 16 | 2000 |
| 84 | 85 | 12 | 21 | 2000 |
| 85 | 100 | 10 | 35 | 2000 |
| 86 | 100 | 10 | 35 | 2000 |
| 87 | 100 | 10 | 35 | 2000 |
| 88 | 100 | 10 | 35 | 2000 |
| 89 | 100 | 10 | 35 | 4000 |
| 90 | 100 | 10 | 35 | 2000 |
| 91 | 80 | 10 | 35 | 4000 |
| 92 | 80 | 10 | 35 | 3500 |

TABLE 11-continued

| Transition number | Orifice potential | inlet potential before Q0 | Potential at collision cell outlet | Positivity threshold |
|---|---|---|---|---|
| 93 | 80 | 10 | 35 | 6000 |
| 94 | 80 | 10 | 35 | 2000 |
| 95 | 80 | 10 | 35 | 2000 |
| 96 | 80 | 10 | 35 | 2000 |
| 97 | 75 | 10 | 11 | 2000 |
| 98 | 75 | 10 | 14 | 2000 |
| 99 | 75 | 10 | 16 | 2000 |
| 100 | 140 | 6 | 10 | 2000 |
| 101 | 140 | 6 | 14 | 2000 |
| 102 | 140 | 6 | 16 | 2000 |
| 103 | 110 | 12 | 10 | 2000 |
| 104 | 110 | 12 | 20 | 2000 |
| 105 | 110 | 12 | 6 | 2000 |
| 106 | 75 | 12 | 14 | 2000 |
| 107 | 75 | 12 | 16 | 2000 |
| 108 | 75 | 12 | 18 | 2000 |
| 109 | 65 | 12 | 18 | 2000 |
| 110 | 65 | 12 | 23 | 2000 |
| 111 | 65 | 12 | 15 | 2000 |
| 112 | 100 | 10 | 35 | 2000 |
| 113 | 100 | 10 | 35 | 2000 |
| 114 | 100 | 10 | 35 | 2000 |
| 115 | 140 | 9 | 14 | 2000 |
| 116 | 140 | 9 | 34 | 2000 |
| 117 | 140 | 9 | 24 | 2000 |
| 118 | 125 | 9 | 18 | 2000 |
| 119 | 125 | 9 | 21 | 2000 |
| 120 | 125 | 9 | 41 | 2000 |
| 121 | 70 | 12 | 10 | 2000 |
| 122 | 70 | 12 | 23 | 2000 |
| 123 | 70 | 12 | 14 | 2000 |
| 124 | 70 | 12 | 17 | 2500 |
| 125 | 70 | 12 | 20 | 2500 |
| 126 | 70 | 12 | 10 | 2500 |
| 127 | 80 | 10 | 35 | 2000 |
| 128 | 80 | 10 | 35 | 2000 |
| 129 | 80 | 10 | 35 | 2000 |
| 130 | 70 | 12 | 14 | 2000 |
| 131 | 70 | 12 | 18 | 2000 |
| 132 | 70 | 12 | 19 | 2000 |
| 133 | 80 | 12 | 14 | 2000 |
| 134 | 80 | 12 | 18 | 2000 |
| 135 | 80 | 12 | 18 | 2000 |
| 136 | 70 | 12 | 12 | 2000 |
| 137 | 70 | 12 | 13 | 2000 |
| 138 | 70 | 12 | 16 | 2000 |
| 139 | 80 | 10 | 35 | 2000 |
| 140 | 80 | 10 | 35 | 2000 |
| 141 | 80 | 10 | 35 | 2000 |
| 142 | 80 | 10 | 35 | 2000 |
| 143 | 80 | 10 | 35 | 2000 |
| 144 | 80 | 10 | 35 | 2000 |
| 145 | 80 | 12 | 16 | 2000 |
| 146 | 80 | 12 | 14 | 2000 |
| 147 | 80 | 12 | 21 | 2000 |
| 148 | 80 | 10 | 35 | 2000 |
| 149 | 80 | 10 | 35 | 2000 |
| 150 | 80 | 10 | 35 | 2000 |
| 151 | 80 | 10 | 35 | 2800 |
| 152 | 80 | 10 | 35 | 2000 |
| 153 | 80 | 10 | 35 | 2000 |

The other machine variables used are as follows:

Type of scan: MRM
MRM planned: yes
Polarity: Positive
Ionization source: Turbo V™ (Applied BioSystems)
Setting Q1: Filtering with unit resolution
Setting Q3: Filtering with unit resolution
Inter-scan pause: 5.00 ms
Scanning speed: 10 Da/s
Curtain gas: 50.00 psi
Cone voltage: 5500.00 V Source temperature: 550.00° C.
Spraying gas: 50.00 psi
Heating gas: 40.00 psi
Collision gas inducing dissociation: 9.00 psi
Dynamic filling: inactivated
Total cycle time: 1.2 s
Detection window: 90 s The areas obtained for each of the transitions and for each of the microorganisms studied were measured. When the area of a transition is greater than or equal to the positivity threshold described in TABLE 11, detection of the transition is regarded as positive and is marked “1” in TABLE 12. When the area of a transition is below the positivity threshold described in TABLE 11, detection of the transition is regarded as negative and is marked “0” in TABLE 12. When the 3 transitions of one and the same peptide are marked “1”, detection of the peptide is regarded as positive. One particular case is an exception to this rule. The peptide corresponding to the transitions numbered 49, 50 and 51 has a transition of very low intensity. In this precise case, when the transitions 49 and 50 are marked “1”, detection of this peptide will be regarded as positive.

TABLE 12

| Transition number | Smp21 | Smp22 |
|---|---|---|
| 1 | 0 | 1 |
| 2 | 0 | 1 |
| 3 | 0 | 1 |
| 4 | 1 | 1 |
| 5 | 1 | 1 |
| 6 | 1 | 1 |
| 7 | 1 | 1 |
| 8 | 1 | 1 |
| 9 | 1 | 1 |
| 10 | 1 | 1 |
| 11 | 1 | 1 |
| 12 | 1 | 1 |
| 13 | 0 | 1 |
| 14 | 0 | 1 |
| 15 | 0 | 1 |
| 16 | 0 | 1 |
| 17 | 0 | 1 |
| 18 | 0 | 1 |
| 19 | 1 | 1 |
| 20 | 1 | 1 |
| 21 | 1 | 1 |
| 22 | 1 | 1 |
| 23 | 1 | 1 |
| 24 | 1 | 1 |
| 25 | 0 | 1 |
| 26 | 0 | 1 |
| 27 | 0 | 1 |
| 28 | 0 | 1 |
| 29 | 0 | 1 |
| 30 | 0 | 1 |
| 31 | 0 | 1 |
| 32 | 0 | 1 |
| 33 | 0 | 1 |
| 34 | 1 | 1 |
| 35 | 1 | 1 |
| 36 | 1 | 1 |
| 37 | 0 | 0 |
| 38 | 0 | 0 |
| 39 | 0 | 0 |
| 40 | 0 | 0 |
| 41 | 0 | 0 |
| 42 | 0 | 0 |
| 43 | 0 | 0 |
| 44 | 0 | 0 |
| 45 | 0 | 0 |
| 46 | 0 | 0 |
| 47 | 0 | 0 |
| 48 | 0 | 0 |

TABLE 12-continued

| Transition number | Smp21 | Smp22 |
|---|---|---|
| 49 | 0 | 0 |
| 50 | 0 | 0 |
| 51 | 0 | 0 |
| 52 | 0 | 0 |
| 53 | 0 | 0 |
| 54 | 0 | 0 |
| 55 | 0 | 0 |
| 56 | 0 | 0 |
| 57 | 0 | 0 |
| 58 | 0 | 0 |
| 59 | 0 | 0 |
| 60 | 0 | 0 |
| 61 | 0 | 0 |
| 62 | 0 | 0 |
| 63 | 0 | 0 |
| 64 | 0 | 0 |
| 65 | 0 | 0 |
| 66 | 0 | 0 |
| 67 | 0 | 0 |
| 68 | 0 | 0 |
| 69 | 0 | 0 |
| 70 | 0 | 0 |
| 71 | 0 | 0 |
| 72 | 0 | 0 |
| 73 | 0 | 0 |
| 74 | 0 | 0 |
| 75 | 0 | 0 |
| 76 | 0 | 0 |
| 77 | 0 | 0 |
| 78 | 0 | 0 |
| 79 | 0 | 0 |
| 80 | 0 | 0 |
| 81 | 0 | 0 |
| 82 | 0 | 0 |
| 83 | 0 | 0 |
| 84 | 0 | 0 |
| 85 | 0 | 0 |
| 86 | 0 | 0 |
| 87 | 0 | 0 |
| 88 | 0 | 0 |
| 89 | 0 | 0 |
| 90 | 0 | 0 |
| 91 | 0 | 0 |
| 92 | 0 | 0 |
| 93 | 0 | 0 |
| 94 | 0 | 0 |
| 95 | 0 | 0 |
| 96 | 0 | 0 |
| 97 | 0 | 0 |
| 98 | 0 | 0 |
| 99 | 0 | 0 |
| 100 | 0 | 0 |
| 101 | 0 | 0 |
| 102 | 0 | 0 |
| 103 | 0 | 0 |
| 104 | 0 | 0 |
| 105 | 0 | 0 |
| 106 | 0 | 0 |
| 107 | 0 | 0 |
| 108 | 0 | 0 |
| 109 | 0 | 0 |
| 110 | 0 | 0 |
| 111 | 0 | 0 |
| 112 | 0 | 0 |
| 113 | 0 | 0 |
| 114 | 0 | 0 |
| 115 | 0 | 0 |
| 116 | 0 | 0 |
| 117 | 0 | 0 |
| 118 | 0 | 0 |
| 119 | 0 | 0 |
| 120 | 0 | 0 |
| 121 | 0 | 0 |
| 122 | 0 | 0 |
| 123 | 0 | 0 |
| 124 | 0 | 0 |
| 125 | 0 | 0 |

TABLE 12-continued

| Transition number | Smp21 | Smp22 |
|---|---|---|
| 126 | 0 | 0 |
| 127 | 0 | 0 |
| 128 | 0 | 0 |
| 129 | 0 | 0 |
| 130 | 0 | 0 |
| 131 | 0 | 0 |
| 132 | 0 | 0 |
| 133 | 0 | 0 |
| 134 | 0 | 0 |
| 135 | 0 | 0 |
| 136 | 0 | 0 |
| 137 | 0 | 0 |
| 138 | 0 | 0 |
| 139 | 0 | 0 |
| 140 | 0 | 0 |
| 141 | 0 | 0 |
| 142 | 0 | 0 |
| 143 | 0 | 0 |
| 144 | 0 | 0 |
| 145 | 0 | 0 |
| 146 | 0 | 0 |
| 147 | 0 | 0 |
| 148 | 0 | 0 |
| 149 | 0 | 0 |
| 150 | 0 | 0 |
| 151 | 0 | 0 |
| 152 | 0 | 0 |
| 153 | 0 | 0 |

Samples Smp21 and Smp22 comprise at least one peptide characteristic of VanA. The bacteria present in samples Smp21 and Smp22 express the ligase VanA, which endows them with resistance to vancomycin and to teicoplanin.

Thus, particularly advantageously, a mechanism of inducible resistance, such as the mechanism of resistance linked to expression of VanA, is detected without an induction phase during culture of the microorganism, after a sample preparation phase performed in less than 3 hours. This method therefore allows quick investigation of the mechanisms of resistance to glycopeptides without a priori on their possible existence.

EXAMPLE 12

Identification of Resistance to Glycopeptides, without Induction

Samples Smp23 and Smp24 are identified according to one of the methods described in examples 1 to 6. Identification of the species is reported in TABLE 13.

TABLE 13

| Name | Species |
|---|---|
| Smp23 | *E. faecium* |
| Smp24 | *E. faecalis* |
| Smp25 | *E. faecium* |

Samples Smp23, Smp24 and Smp25 correspond to the species *Enterococcus faecalis* or *Enterococcus faecium*, which may comprise a mechanism of resistance of the Van type.

The following method is then employed for investigating such a mechanism. Each sample is treated according to example 10, with the following modifications:

Step 1: a colony line of 3 cm is taken with a 10 μl loop (against a colony previously).

Step 7: addition of 2 μg of trypsin.

Each sample is analyzed according to example 8 apart from the elements mentioned below.

The transitions mentioned in TABLE 3 are detected using the parameters shown in TABLES 4 and 11.

As in example 8, the positive areas are marked “1” in TABLE 14. The positive peptides are detected according to the rules of example 8.

TABLE 14

| Transition number | Smp23 | Smp24 | Smp25 |
|---|---|---|---|
| 1 | 0 | 0 | 1 |
| 2 | 0 | 0 | 1 |
| 3 | 0 | 0 | 1 |
| 4 | 0 | 0 | 1 |
| 5 | 0 | 0 | 1 |
| 6 | 0 | 0 | 1 |
| 7 | 0 | 0 | 1 |
| 8 | 0 | 0 | 1 |
| 9 | 0 | 0 | 1 |
| 10 | 0 | 0 | 1 |
| 11 | 0 | 0 | 1 |
| 12 | 0 | 0 | 1 |
| 13 | 0 | 0 | 0 |
| 14 | 0 | 0 | 0 |
| 15 | 0 | 0 | 0 |
| 16 | 0 | 0 | 0 |
| 17 | 0 | 0 | 0 |
| 18 | 0 | 0 | 0 |
| 19 | 0 | 0 | 1 |
| 20 | 0 | 0 | 1 |
| 21 | 0 | 0 | 1 |
| 22 | 0 | 0 | 1 |
| 23 | 0 | 0 | 1 |
| 24 | 0 | 0 | 1 |
| 25 | 0 | 0 | 1 |
| 26 | 0 | 0 | 1 |
| 27 | 0 | 0 | 1 |
| 28 | 0 | 0 | 1 |
| 29 | 0 | 0 | 1 |
| 30 | 0 | 0 | 1 |
| 31 | 0 | 0 | 1 |
| 32 | 0 | 0 | 1 |
| 33 | 0 | 0 | 1 |
| 34 | 0 | 0 | 1 |
| 35 | 0 | 0 | 1 |
| 36 | 0 | 0 | 1 |
| 37 | 1 | 0 | 0 |
| 38 | 1 | 0 | 0 |
| 39 | 1 | 0 | 0 |
| 40 | 1 | 0 | 0 |
| 41 | 1 | 0 | 0 |
| 42 | 1 | 0 | 0 |
| 43 | 1 | 0 | 0 |
| 44 | 1 | 0 | 0 |
| 45 | 1 | 0 | 0 |
| 46 | 1 | 0 | 0 |
| 47 | 1 | 0 | 0 |
| 48 | 1 | 0 | 0 |
| 49 | 1 | 0 | 0 |
| 50 | 1 | 0 | 0 |
| 51 | 1 | 0 | 0 |
| 52 | 1 | 0 | 0 |
| 53 | 1 | 0 | 0 |
| 54 | 1 | 0 | 0 |
| 55 | 1 | 0 | 0 |
| 56 | 1 | 0 | 0 |
| 57 | 1 | 0 | 0 |
| 58 | 0 | 0 | 0 |
| 59 | 0 | 0 | 0 |
| 60 | 0 | 0 | 0 |
| 61 | 0 | 0 | 0 |
| 62 | 0 | 0 | 0 |
| 63 | 0 | 0 | 0 |
| 64 | 0 | 0 | 0 |
| 65 | 0 | 0 | 0 |
| 66 | 0 | 0 | 0 |
| 67 | 0 | 0 | 0 |
| 68 | 0 | 0 | 0 |
| 69 | 0 | 0 | 0 |
| 70 | 0 | 0 | 0 |
| 71 | 0 | 0 | 0 |
| 72 | 0 | 0 | 0 |
| 73 | 0 | 0 | 0 |
| 74 | 0 | 0 | 0 |
| 75 | 0 | 0 | 0 |
| 76 | 0 | 0 | 0 |
| 77 | 0 | 0 | 0 |
| 78 | 0 | 0 | 0 |
| 79 | 0 | 0 | 0 |
| 80 | 0 | 0 | 0 |
| 81 | 0 | 0 | 0 |
| 82 | 0 | 0 | 0 |
| 83 | 0 | 0 | 0 |
| 84 | 0 | 0 | 0 |
| 85 | 0 | 0 | 0 |
| 86 | 0 | 0 | 0 |
| 87 | 0 | 0 | 0 |
| 88 | 0 | 0 | 0 |
| 89 | 0 | 0 | 0 |
| 90 | 0 | 0 | 0 |
| 91 | 1 | 0 | 1 |
| 92 | 1 | 0 | 1 |
| 93 | 0 | 0 | 0 |
| 94 | 0 | 0 | 0 |
| 95 | 0 | 0 | 0 |
| 96 | 0 | 0 | 0 |
| 97 | 0 | 0 | 0 |
| 98 | 0 | 0 | 0 |
| 99 | 0 | 0 | 0 |
| 100 | 0 | 0 | 0 |
| 101 | 0 | 0 | 0 |
| 102 | 0 | 0 | 0 |
| 103 | 0 | 0 | 0 |
| 104 | 0 | 0 | 0 |
| 105 | 0 | 0 | 0 |
| 106 | 0 | 0 | 0 |
| 107 | 0 | 0 | 0 |
| 108 | 0 | 0 | 0 |
| 109 | 0 | 0 | 0 |
| 110 | 0 | 0 | 0 |
| 111 | 0 | 0 | 0 |
| 112 | 0 | 0 | 0 |
| 113 | 0 | 0 | 0 |
| 114 | 0 | 0 | 0 |
| 115 | 0 | 0 | 0 |
| 116 | 0 | 0 | 0 |
| 117 | 0 | 0 | 0 |
| 118 | 0 | 0 | 0 |
| 119 | 0 | 0 | 0 |
| 120 | 0 | 0 | 0 |
| 121 | 0 | 0 | 0 |
| 122 | 0 | 0 | 0 |
| 123 | 0 | 0 | 0 |
| 124 | 0 | 0 | 0 |
| 125 | 0 | 0 | 0 |
| 126 | 0 | 0 | 0 |
| 127 | 0 | 0 | 0 |
| 128 | 0 | 0 | 0 |
| 129 | 0 | 0 | 0 |
| 130 | 0 | 0 | 0 |
| 131 | 0 | 0 | 0 |
| 132 | 0 | 0 | 0 |
| 133 | 0 | 0 | 0 |
| 134 | 0 | 0 | 0 |
| 135 | 0 | 0 | 0 |
| 136 | 0 | 0 | 0 |
| 137 | 0 | 0 | 0 |
| 138 | 0 | 0 | 0 |
| 139 | 0 | 0 | 0 |
| 140 | 0 | 0 | 0 |

TABLE 14-continued

| Transition number | Smp23 | Smp24 | Smp25 |
|---|---|---|---|
| 141 | 0 | 0 | 0 |
| 142 | 0 | 0 | 0 |
| 143 | 0 | 0 | 0 |
| 144 | 0 | 0 | 0 |
| 145 | 0 | 0 | 0 |
| 146 | 0 | 0 | 0 |
| 147 | 0 | 0 | 0 |
| 148 | 0 | 0 | 0 |
| 149 | 0 | 0 | 0 |
| 150 | 0 | 0 | 0 |
| 151 | 0 | 0 | 0 |
| 152 | 0 | 0 | 0 |
| 153 | 0 | 0 | 0 |

Sample Smp23 comprises at least one peptide characteristic of VanB. The bacterium present in sample Smp23 expresses the ligase VanB, which endows it with resistance to vancomycin.

Sample Smp25 comprises at least one peptide characteristic of VanA. The bacterium present in sample Smp25 expresses the ligase VanA, which endows it with resistance to vancomycin and to teicoplanin.

Conversely, sample Smp24 does not have any peptide characteristic of resistance of the Van type. The bacterium present in sample Smp24 may be sensitive to the glycopeptides of the vancomycin or teicoplanin type.

Thus, particularly advantageously, a mechanism of inducible resistance, such as the mechanism of resistance linked to expression of VanB, is detected without an induction phase during culture of the microorganism, after a sample preparation phase performed in less than 3 hours. Also very advantageously, all the mechanisms of resistance to glycopeptides can be investigated and detected simultaneously. Thus, 2 mechanisms of resistance, VanB and VanA, are detected in samples Smp23 and Smp25 respectively using the same method. This method therefore allows quick investigation of the mechanisms of resistance to glycopeptides without a priori on their possible existence.

BIBLIOGRAPHIC REFERENCES

[1] J. Anhalt & C. Fenselau, 1975, Anal. Chem., 47(2):219-225.
[2] A. Fox et al, ed., 1990, Analytical microbiology methods: chromatography and mass spectrometry, Plenum Press, New York, N.Y.
[3] M. Claydon et al, 1996, Nature Biotech. 14:1584-1586.
[4] T. Krishnamurthy & P. Ross, 1996, Rapid Com. Mass Spec., 10:1992-1996.
[5] P. Seng et al. 2009, Clin. Infect. Dis., 49:543-551.
[6] C. Fenselau et al., 2008, Appl. Environ. Microbiol., 904-906.
[7] S. Hofstadler et al., 2005, Int. J. Mass Spectrom., 242:23-41.
[8] D. Ecker, 2008, Nat. Rev. Microbiol., 6(7):553-558.
[9] Sujatha, S. & Praharaj, I. Glycopeptide Resistance in Gram-Positive Cocci: A Review. Interdiscip. Perspect. Infect. Dis 2012, 781679 (2012
[10] W.-J. Chen et al., 2008, Anal. Chem., 80: 9612-9621
[11] D. Lopez-Ferrer et al., 2008, Anal. Chem., 80:8930-8936.
[12] D. Lopez-Ferrer et al., 2005, J. Proteome res., 4(5): 1569-1574.
[13] T. Fortin et al., 2009, Mol. Cell Proteomics, 8(5): 1006-1015.
[14] H. Keshishian et al., 2007, Mol. Cell Proteomics, 2212-2229.
[15] J. Stal-Zeng et al., 2007, Mol. Cell Proteomics, 1809-1817.
[16] Gaskell, Electrospray: principles and practise, 1997, J. Mass Spectrom., 32, 677-688).
[17] V. Fusaro et al., 2009, Nature Biotech. 27, 190-198.
[18] J. Mead et al., 15 Nov. 2008, Mol. Cell Proteomics, E-pub.
[19] F. Desiere et al., 2006, Nucleic Acids Res., 34(database issue): D655-8).
[20] L. Anderson & C. Hunter, 2006, Mol. Cell Proteomics, 573-588).
[21] B. Han & R. Higgs, 2008, Brief Funct Genomic Proteomic., 7(5):340-54).
[22] K.-Y. Wang et al., 2008, Anal Chem, 80(16) 6159-6167).
[23] J. Bundy & C. Fenselau, 1999, Anal. Chem. 71: 1460-1463.
[24] K-C Ho et al., 2004, Anal. Chem. 76: 7162-7268.
[25] Y. S. Lin et al., 2005, Anal. Chem., 77: 1753-1760.
[26] S. Vaidyanathan et al., 2001, Anal. Chem., 73:4134-4144.
[27] R. Everley et al., 2009, J. Microbiol. Methods, 77:152-158.
[28] Manes N. et al., 2007, Mol. & Cell. Proteomics, 6(4): 717-727.
[29] R. Nandakumar et al., 2009, Oral Microbiology Immunology, 24:347-352).
[30] L. Hernychova et al., 2008, Anal. Chem., 80:7097-7104.
[31] J.-M. Pratt et al., 2006, Nat. Protoc., 1:1029-1043.
[32] V. Brun et al., 2007, Mol. Cell Proteomics, 2139-2149.

The invention claimed is:

1. A method of detection, for at least one microorganism contained in a sample, of at least one marker of resistance to a glycopeptide that is vancomycin, comprising detection, by MS/MS mass spectrometry in MRM mode, of at least one peptide of said microorganism selected from the Van type peptides of SEQ ID No. 5 to 16, 29 to 35, 59 to 71, 80 to 83, 85 to 91, 95 to 102, 104 to 120, 122 to 139 or 141 to 154.

2. The method of detection as claimed in claim 1, comprising a step prior to the detection step of induction of a resistance mechanism by bringing said sample into contact with said glycopeptide beforehand.

3. The method of detection as claimed in claim 1, in which said at least one peptide that is detected is selected from VanA type peptides of SEQ ID No. 5 to SEQ ID No. 16.

4. The method of detection as claimed in claim 1, in which said at least one peptide that is detected is selected from VanA type peptides of SEQ ID No. 6, SEQ ID No. 7, SEQ ID No. 8, SEQ ID No. 11, SEQ ID No. 12, SEQ ID No. 13, SEQ ID No. 15, or SEQ ID No. 16.

5. The method of detection as claimed in claim 2, in which said at least one peptide that is detected is selected from VanA type peptides of SEQ ID No. 5 to SEQ ID No. 16.

6. The method of detection as claimed in claim 1, in which said at least one peptide that is detected is selected from VanB type peptides of SEQ ID No. 29 to SEQ ID No. 35.

7. The method of detection as claimed in claim 2, in which said at least one peptide that is detected is selected from VanB type peptides of SEQ ID No. 29, SEQ ID No. 30, SEQ ID No. 32 or SEQ ID No. 33.

8. The method of detection as claimed in claim 1, in which said at least one peptide that is detected is selected from VanC type peptides of SEQ ID No. 59 to SEQ ID No. 71.

9. The method of detection as claimed in claim 1, in which said at least one peptide that is detected is selected from VanD type peptides of SEQ ID No. 80 to SEQ ID No. 83.

10. The method of detection as claimed in claim 1, in which said at least one peptide that is detected is selected from VanD type peptides of SEQ ID No. 80, SEQ ID No. 81 or SEQ ID No. 83.

11. The method of detection as claimed in claim 2, in which said at least one peptide that is detected is selected from VanD peptides of SEQ ID No. 80, SEQ ID No. 81 or SEQ ID No. 83.

12. The method of detection as claimed in claim 1, in which said at least one peptide that is detected is selected from VanE type peptides of SEQ ID No. 85 to SEQ ID No. 91.

13. The method of detection as claimed in claim 2, in which said at least one peptide that is detected includes VanE type peptide of SEQ ID No. 89.

14. The method of detection as claimed in claim 1, in which said at least one peptide that is detected is selected from VanG type peptides of SEQ ID No. 95 to SEQ ID No. 102.

15. The method of detection as claimed in claim 1, in which said at least one peptide that is detected includes at least one VanG type peptide of SEQ ID No. 97 or SEQ ID No. 100.

16. The method of detection as claimed in claim 2, in which said at least one peptide that is detected is selected from VanG type peptides of SEQ ID No. 95, SEQ ID No. 96, SEQ ID No. 97, SEQ ID No. 98, SEQ ID No. 100 or SEQ ID No. 102.

17. The method of detection as claimed in claim 1, in which said at least one peptide that is detected is selected from VanL type peptides of SEQ ID No. 104 to SEQ ID No. 120.

18. The method of detection as claimed in claim 1, in which said at least one peptide that is detected is selected from VanM type peptides of SEQ ID No. 122 to SEQ ID No. 139.

19. The method of detection as claimed in claim 1, in which said at least one peptide that is detected is selected from VanN type peptides of SEQ ID No. 141 to SEQ ID No. 154.

20. A method of detecting at least one marker of resistance to a glycoprotein of at least one microorganism, comprising detecting whether at least one peptide that is any of SEQ ID NOs: 5-16, 29-35, 59-71, 80-83, 85-91, 95-102, 104-120, 122-139, or 141-154 is present in a sample by mass spectrometry.

21. The method as claimed in claim 20, wherein the mass spectrometry is MS/MS mass spectrometry.

22. The method as claimed in claim 20, further comprising contacting the sample with the glycoprotein before detection.

23. The method as claimed in claim 22, wherein the glycoprotein is vancomycin.

* * * * *

SEQUENCE LISTING

```
<160> NUMBER OF SEQ ID NOS: 154

<210> SEQ ID NO 1
<211> LENGTH: 359
<212> TYPE: PRT
<213> ORGANISM: Unknown
<220> FEATURE:
<223> OTHER INFORMATION: peptide from a microbial resistance gene

<400> SEQUENCE: 1

Met Lys Lys Pro Leu Lys Thr Val Trp Ile Leu Lys Gly Asp Arg Ser
  1             5                  10                  15

Met Asn Arg Ile Lys Val Ala Ile Leu Phe Gly Gly Cys Ser Glu Glu
```

-continued

```
            20                  25                  30

His Asp Val Ser Val Lys Ser Ala Ile Glu Ile Ala Ala Asn Ile Asn
        35                  40                  45

Lys Glu Lys Tyr Glu Pro Leu Tyr Ile Gly Ile Thr Lys Ser Gly Val
    50                  55                  60

Trp Lys Met Cys Glu Lys Pro Cys Ala Glu Trp Glu Asn Asp Asn Cys
65                  70                  75                  80

Tyr Ser Ala Val Leu Ser Pro Asp Lys Lys Met His Gly Leu Leu Val
                85                  90                  95

Lys Lys Asn His Glu Tyr Glu Ile Asn His Val Asp Val Ala Phe Ser
            100                 105                 110

Ala Leu His Gly Lys Ser Gly Glu Asp Gly Ser Ile Gln Gly Leu Phe
        115                 120                 125

Glu Leu Ser Gly Ile Pro Phe Val Gly Cys Asp Ile Gln Ser Ser Ala
    130                 135                 140

Ile Cys Met Asp Lys Ser Leu Thr Tyr Ile Val Ala Lys Asn Ala Gly
145                 150                 155                 160

Ile Ala Thr Pro Ala Phe Trp Val Ile Asn Lys Asp Asp Arg Pro Val
                165                 170                 175

Ala Ala Thr Phe Thr Tyr Pro Val Phe Val Lys Pro Ala Arg Ser Gly
            180                 185                 190

Ser Ser Phe Gly Val Lys Lys Val Asn Ser Ala Asp Glu Leu Asp Tyr
        195                 200                 205

Ala Ile Glu Ser Ala Arg Gln Tyr Asp Ser Lys Ile Leu Ile Glu Gln
    210                 215                 220

Ala Val Ser Gly Cys Glu Val Gly Cys Ala Val Leu Gly Asn Ser Ala
225                 230                 235                 240

Ala Leu Val Val Gly Glu Val Asp Gln Ile Arg Leu Gln Tyr Gly Ile
                245                 250                 255

Phe Arg Ile His Gln Glu Val Glu Pro Glu Lys Gly Ser Glu Asn Ala
            260                 265                 270

Val Ile Thr Val Pro Ala Asp Leu Ser Ala Glu Glu Arg Gly Arg Ile
        275                 280                 285

Gln Glu Thr Ala Lys Lys Ile Tyr Lys Ala Leu Gly Cys Arg Gly Leu
    290                 295                 300

Ala Arg Val Asp Met Phe Leu Gln Asp Asn Gly Arg Ile Val Leu Asn
305                 310                 315                 320

Glu Val Asn Thr Leu Pro Gly Phe Thr Ser Tyr Ser Arg Tyr Pro Arg
                325                 330                 335

Met Met Ala Ala Ala Gly Ile Ala Leu Pro Glu Leu Ile Asp Arg Leu
            340                 345                 350

Ile Val Leu Ala Leu Lys Gly
        355
```

<210> SEQ ID NO 2
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 2

```
Met Asn Arg Ile Lys Val Ala Ile Leu Phe Gly Gly Cys Ser Glu Glu
  1               5                  10                  15

His Asp Val Ser Leu Lys Ser Ala Ile Glu Ile Ala Ala Asn Ile Asn
```

-continued

```
            20                  25                  30

Lys Glu Lys Tyr Glu Pro Leu Tyr Ile Gly Ile Thr Lys Ser Gly Val
        35                  40                  45

Trp Lys Met Cys Glu Lys Pro Cys Ala Glu Trp Glu Asn Asp Asn Cys
    50                  55                  60

Tyr Ser Ala Val Leu Ser Pro Asp Lys Lys Met His Gly Leu Leu Val
 65                  70                  75                  80

Lys Lys Asn His Glu Tyr Glu Ile Asn His Val Asp Val Ala Phe Ser
                85                  90                  95

Ala Leu His Gly Lys Ser Gly Glu Asp Gly Ser Ile Gln Gly Leu Phe
            100                 105                 110

Glu Leu Ser Gly Ile Pro Phe Val Gly Cys Asp Ile Gln Ser Ser Ala
        115                 120                 125

Ile Cys Met Asp Lys Ser Leu Thr Tyr Ile Val Ala Lys Asn Ala Gly
    130                 135                 140

Ile Ala Thr Pro Ala Phe Trp Val Ile Asn Lys Asp Asp Arg Pro Val
145                 150                 155                 160

Ala Ala Thr Phe Thr Tyr Pro Val Phe Val Lys Pro Ala Arg Ser Gly
                165                 170                 175

Ser Ser Phe Gly Val Lys Lys Val Asn Ser Ala Asp Glu Leu Asp Tyr
            180                 185                 190

Ala Ile Glu Ser Ala Arg Gln Tyr Asp Ser Lys Ile Leu Ile Glu Gln
        195                 200                 205

Ala Val Ser Gly Cys Glu Val Gly Cys Ala Val Leu Gly Asn Ser Ala
    210                 215                 220

Ala Leu Val Val Gly Glu Val Asp Gln Ile Arg Leu Gln Tyr Gly Ile
225                 230                 235                 240

Phe Arg Ile His Gln Glu Val Glu Pro Glu Lys Gly Ser Glu Asn Ala
                245                 250                 255

Val Ile Thr Val Pro Ala Asp Leu Ser Ala Glu Glu Arg Gly Arg Ile
            260                 265                 270

Gln Glu Thr Ala Lys Lys Ile Tyr Lys Ala Leu Gly Cys Arg Gly Leu
        275                 280                 285

Ala Arg Val Asp Met Phe Leu Gln Asp Asn Gly Arg Ile Val Leu Asn
    290                 295                 300

Glu Val Asn Thr Leu Pro Gly Phe Thr Ser Tyr Ser Arg Tyr Pro Arg
305                 310                 315                 320

Met Met Ala Ala Ala Gly Ile Ala Leu Pro Glu Leu Ile Asp Arg Leu
                325                 330                 335

Ile Val Leu Ala Leu Lys Gly
            340


<210> SEQ ID NO 3
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 3

Met Asn Arg Ile Lys Val Ala Ile Leu Phe Gly Gly Cys Ser Glu Glu
  1               5                  10                  15

His Asp Val Ser Val Lys Ser Ala Ile Glu Ile Ala Ala Asn Ile Asn
            20                  25                  30

Lys Glu Lys Tyr Glu Pro Leu Tyr Ile Gly Ile Thr Lys Ser Gly Val
```

-continued

```
        35                  40                  45

Trp Lys Met Cys Glu Lys Pro Cys Ala Glu Trp Glu Asn Asp Asn Cys
    50                  55                  60

Tyr Ser Ala Val Leu Ser Pro Asp Lys Lys Met His Gly Leu Leu Val
 65                 70                  75                  80

Lys Lys Asn His Glu Tyr Glu Ile Asn His Val Asp Val Ala Phe Ser
                85                  90                  95

Ala Leu His Gly Lys Ser Gly Glu Asp Gly Ser Ile Gln Gly Leu Phe
            100                 105                 110

Glu Leu Ser Gly Ile Pro Phe Val Gly Cys Asp Ile Gln Ser Ser Ala
        115                 120                 125

Ile Cys Met Asp Lys Ser Leu Thr Tyr Ile Val Ala Lys Asn Ala Gly
    130                 135                 140

Ile Ala Thr Pro Ala Phe Trp Val Ile Asn Lys Asp Asp Arg Pro Val
145                 150                 155                 160

Ala Ala Thr Phe Thr Tyr Pro Val Phe Val Lys Pro Ala Arg Ser Gly
                165                 170                 175

Ser Ser Phe Gly Val Lys Lys Val Asn Ser Ala Asp Glu Leu Asp Tyr
            180                 185                 190

Ala Ile Glu Ser Ala Arg Gln Tyr Asp Ser Lys Ile Leu Ile Glu Gln
        195                 200                 205

Ala Val Ser Gly Cys Glu Val Gly Cys Ala Val Leu Gly Asn Ser Ala
    210                 215                 220

Ala Leu Ala Val Gly Glu Val Asp Gln Ile Arg Leu Gln Tyr Gly Ile
225                 230                 235                 240

Phe Arg Ile His Gln Glu Val Glu Pro Glu Lys Gly Ser Glu Asn Ala
                245                 250                 255

Val Ile Thr Val Pro Ala Asp Leu Ser Ala Glu Glu Arg Gly Arg Ile
            260                 265                 270

Gln Glu Thr Ala Lys Lys Ile Tyr Lys Ala Leu Gly Cys Arg Gly Leu
        275                 280                 285

Ala Arg Val Asp Met Phe Leu Gln Asp Asn Gly Arg Ile Val Leu Asn
    290                 295                 300

Glu Val Asn Thr Leu Pro Gly Phe Thr Ser Tyr Ser Arg Tyr Pro Arg
305                 310                 315                 320

Met Met Ala Ala Ala Gly Ile Ala Leu Pro Glu Leu Ile Asp Arg Leu
                325                 330                 335

Ile Val Leu Ala Leu Lys Gly
            340


<210> SEQ ID NO 4
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 4

Met Asn Arg Ile Lys Val Ala Ile Leu Phe Gly Gly Cys Ser Glu Glu
  1               5                  10                  15

His Asp Val Ser Val Lys Ser Ala Ile Glu Ile Ala Ala Asn Ile Asn
             20                  25                  30

Lys Glu Lys Tyr Glu Pro Leu Tyr Ile Gly Ile Thr Lys Ser Gly Val
        35                  40                  45

Trp Lys Met Cys Glu Lys Pro Cys Ala Glu Trp Glu Asn Asp Asn Cys
```

-continued

```
        50                  55                  60

Tyr Ser Ala Val Leu Ser Pro Asp Lys Lys Met His Gly Leu Leu Val
 65                  70                  75                  80

Lys Lys Asn His Glu Tyr Glu Ile Asn His Val Asp Val Ala Phe Ser
                 85                  90                  95

Ala Leu His Gly Lys Ser Gly Glu Asp Gly Ser Ile Gln Gly Leu Phe
            100                 105                 110

Glu Leu Ser Gly Ile Pro Phe Val Gly Cys Asp Ile Gln Ser Ser Ala
        115                 120                 125

Ile Cys Met Asp Lys Ser Leu Thr Tyr Ile Val Ala Lys Asn Ala Gly
    130                 135                 140

Ile Ala Thr Pro Ala Phe Trp Val Ile Asn Lys Asp Asp Arg Pro Val
145                 150                 155                 160

Ala Ala Thr Phe Thr Tyr Pro Val Phe Val Lys Pro Ala Arg Ser Gly
                165                 170                 175

Ser Ser Phe Gly Val Lys Lys Val Asn Ser Ala Asp Glu Leu Asp Tyr
            180                 185                 190

Ala Ile Glu Ser Ala Arg Gln Tyr Asp Ser Lys Ile Leu Ile Glu Gln
        195                 200                 205

Ala Val Ser Gly Cys Glu Val Gly Cys Ala Val Leu Gly Asn Ser Ala
    210                 215                 220

Ala Leu Val Val Gly Glu Val Asp Gln Ile Arg Leu Gln Tyr Gly Ile
225                 230                 235                 240

Phe Arg Ile His Gln Glu Val Glu Pro Glu Lys Gly Ser Glu Asn Ala
                245                 250                 255

Val Ile Thr Val Pro Ala Asp Leu Ser Ala Glu Glu Arg Gly Arg Ile
            260                 265                 270

Gln Glu Thr Ala Lys Lys Ile Tyr Lys Ala Leu Gly Cys Arg Gly Leu
        275                 280                 285

Ala Arg Val Asp Met Phe Leu Gln Asp Asn Gly Arg Ile Val Leu Asn
    290                 295                 300

Glu Val Asn Thr Leu Pro Gly Phe Thr Ser Tyr Ser Arg Tyr Pro Arg
305                 310                 315                 320

Met Met Ala Ala Ala Gly Ile Ala Leu Pro Glu Leu Ile Asp Arg Leu
                325                 330                 335

Ile Val Leu Ala Leu Lys Gly
            340
```

<210> SEQ ID NO 5
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 5

```
Ile His Gln Glu Val Glu Pro Glu Lys
  1               5
```

<210> SEQ ID NO 6
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 6

Leu Ile Val Leu Ala Leu Lys
1 5

<210> SEQ ID NO 7
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 7

Leu Gln Tyr Gly Ile Phe Arg
1 5

<210> SEQ ID NO 8
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 8

Met His Gly Leu Leu Val Lys
1 5

<210> SEQ ID NO 9
<211> LENGTH: 15
<212> TYPE: PRT
<213> ORGANISM: Unknown
<220> FEATURE:
<223> OTHER INFORMATION: peptide from a microbial resistance gene

<400> SEQUENCE: 9

Met Met Ala Ala Ala Gly Ile Ala Leu Pro Glu Leu Ile Asp Arg
1 5 10 15

<210> SEQ ID NO 10
<211> LENGTH: 14
<212> TYPE: PRT
<213> ORGANISM: Unknown
<220> FEATURE:
<223> OTHER INFORMATION: peptide from a microbial resistance gene

<400> SEQUENCE: 10

Asn Ala Gly Ile Ala Thr Pro Ala Phe Trp Val Ile Asn Lys
1 5 10

<210> SEQ ID NO 11
<211> LENGTH: 11
<212> TYPE: PRT
<213> ORGANISM: Unknown
<220> FEATURE:
<223> OTHER INFORMATION: peptide from a microbial resistance gene

<400> SEQUENCE: 11

Ser Ala Ile Glu Ile Ala Ala Asn Ile Asn Lys
1 5 10

<210> SEQ ID NO 12
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 12

Ser Gly Ser Ser Phe Gly Val Lys 1 5

<210> SEQ ID NO 13
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 13

Ser Leu Thr Tyr Ile Val Ala Lys
1 5

<210> SEQ ID NO 14
<211> LENGTH: 10
<212> TYPE: PRT
<213> ORGANISM: Unknown
<220> FEATURE:
<223> OTHER INFORMATION: peptide from a microbial resistance gene

<400> SEQUENCE: 14

Val Asp Met Phe Leu Gln Asp Asn Gly Arg
1 5 10

<210> SEQ ID NO 15
<211> LENGTH: 15
<212> TYPE: PRT
<213> ORGANISM: Unknown
<220> FEATURE:
<223> OTHER INFORMATION: peptide from a microbial resistance gene

<400> SEQUENCE: 15

Val Asn Ser Ala Asp Glu Leu Asp Tyr Ala Ile Glu Ser Ala Arg
1 5 10 15

<210> SEQ ID NO 16
<211> LENGTH: 10
<212> TYPE: PRT
<213> ORGANISM: Unknown
<220> FEATURE:
<223> OTHER INFORMATION: peptide from a microbial resistance gene

<400> SEQUENCE: 16

Tyr Glu Pro Leu Tyr Ile Gly Ile Thr Lys
1 5 10

<210> SEQ ID NO 17
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 17

Met Asn Lys Ile Lys Val Ala Ile Ile Phe Gly Gly Cys Ser Glu Glu
1 5 10 15

His Asp Val Ser Val Lys Ser Ala Ile Glu Ile Ala Ala Asn Ile Asn
20 25 30

Thr Glu Lys Phe Asp Pro His Tyr Ile Gly Ile Thr Lys Asn Gly Val
35 40 45

Trp Lys Leu Cys Lys Lys Pro Cys Thr Glu Trp Glu Ala Asp Ser Leu
50 55 60

Pro Ala Ile Phe Ser Pro Asp Arg Lys Thr His Gly Leu Leu Val Met
65 70 75 80

```
Lys Glu Arg Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Glu
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Glu Lys Gly Asp Lys Pro Glu Ala
145                 150                 155                 160

Arg Thr Leu Thr Tyr Pro Val Phe Val Lys Pro Ala Arg Ser Gly Ser
                165                 170                 175

Ser Phe Gly Val Thr Lys Val Asn Ser Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Ile Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Ala Ala Ala Ala Gly Ile Thr Leu Pro Ala Leu Ile Asp Ser Leu Ile
                325                 330                 335

Thr Leu Ala Ile Glu Arg
            340
```

<210> SEQ ID NO 18
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 18

```
Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95
```

```
Leu His Gly Lys Cys Gly Glu Asp Gly Ala Ile Gln Gly Leu Phe Glu
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Val Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Met Ala Ala Ala Gly Ile Thr Leu Pro Ala Leu Ile Asp Ser Leu Ile
                325                 330                 335

Thr Leu Ala Leu Lys Arg
            340


<210> SEQ ID NO 19
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 19

Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110
```

```
Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Ile Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Val Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Met Pro Gly Phe Thr Ser Tyr Ser Arg Tyr Pro Arg Met
305                 310                 315                 320

Val Ala Ala Ala Gly Ile Thr Leu Pro Ala Leu Ile Asp Ser Leu Ile
                325                 330                 335

Thr Leu Ala Leu Lys Arg
            340


<210> SEQ ID NO 20
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 20

Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Ala
        115                 120                 125
```

-continued

```
Cys Met Asp Lys Ser Leu Ala Tyr Ile Leu Thr Lys Asn Ala Gly Ile
    130                 135                 140

Ala Val Pro Glu Phe Gln Ile Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Val Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Met Pro Gly Phe Thr Ser Tyr Ser Arg Tyr Thr Arg Met
305                 310                 315                 320

Val Ala Ala Ala Gly Ile Thr Leu Pro Ala Leu Ile Asp Ser Leu Ile
                325                 330                 335

Thr Leu Ala Leu Lys Arg
            340


<210> SEQ ID NO 21
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 21

Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
            20                  25                  30

Thr Glu Lys Phe Asp Pro His Tyr Ile Gly Ile Thr Lys Asn Gly Val
        35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140
```

```
Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Leu Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Met Ala Ala Ala Gly Ile Thr Leu Pro Ala Leu Ile Asp Ser Leu Ile
                325                 330                 335

Thr Leu Ala Leu Lys Arg
            340


<210> SEQ ID NO 22
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 22

Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
            20                  25                  30

Thr Glu Lys Phe Asp Pro His Tyr Ile Gly Ile Thr Lys Asn Gly Val
        35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160
```

```
Gly Ala Leu Thr Tyr Pro Val Phe Val Lys Pro Ala Arg Ser Gly Ser
                165                 170                 175

Ser Phe Gly Val Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Met Ala Ala Ala Gly Ile Thr Leu Pro Ala Leu Ile Asp Ser Leu Ile
                325                 330                 335

Thr Leu Ala Leu Lys Arg
            340
```

<210> SEQ ID NO 23
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 23

```
Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Val
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175
```

-continued

```
Ser Phe Gly Val Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Val Ala Ala Ala Gly Ile Thr Leu Pro Ala Leu Ile Asp Ser Leu Ile
                325                 330                 335

Thr Leu Ala Leu Lys Arg
            340


<210> SEQ ID NO 24
<211> LENGTH: 344
<212> TYPE: PRT
<213> ORGANISM: Unknown
<220> FEATURE:
<223> OTHER INFORMATION: peptide from a microbial resistance gene

<400> SEQUENCE: 24

Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asp
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Gly Gly Glu Asp Gly Ala Ile Gln Gly Leu
            100                 105                 110

Phe Val Leu Ser Gly Ile Pro Tyr Val Gly Cys Asp Ile Gln Ser Ser
        115                 120                 125

Ala Ala Cys Met Asp Lys Ser Leu Ala Tyr Ile Leu Thr Lys Asn Ala
    130                 135                 140

Gly Ile Ala Val Pro Glu Phe Gln Met Ile Asp Lys Gly Asp Lys Pro
145                 150                 155                 160

Glu Ala Gly Ala Leu Thr Tyr Pro Val Phe Val Lys Pro Ala Arg Ser
                165                 170                 175

Gly Ser Ser Phe Gly Val Thr Lys Val Asn Gly Thr Glu Glu Leu Asn
            180                 185                 190
```

-continued

Ala Ala Ile Glu Ala Ala Gly Gln Tyr Asp Gly Lys Ile Leu Ile Glu
        195                 200                 205

Gln Ala Ile Ser Gly Cys Glu Val Gly Cys Ala Val Met Gly Asn Glu
    210                 215                 220

Asp Asp Leu Ile Val Gly Glu Val Asp Gln Ile Arg Leu Ser His Gly
225                 230                 235                 240

Ile Phe Arg Ile His Gln Glu Asn Glu Pro Glu Lys Gly Ser Glu Asn
                245                 250                 255

Ala Met Ile Thr Val Pro Ala Asp Ile Pro Val Glu Glu Arg Asn Arg
            260                 265                 270

Val Gln Glu Thr Ala Lys Lys Val Tyr Arg Val Leu Gly Cys Arg Gly
        275                 280                 285

Leu Ala Arg Val Asp Leu Phe Leu Gln Glu Asp Gly Gly Ile Val Leu
    290                 295                 300

Asn Glu Val Asn Thr Leu Pro Gly Phe Thr Ser Tyr Ser Arg Tyr Pro
305                 310                 315                 320

Arg Met Met Ala Ala Ala Gly Ile Thr Leu Pro Ala Leu Ile Asp Ser
                325                 330                 335

Leu Ile Thr Leu Ala Leu Lys Arg
            340

<210> SEQ ID NO 25
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 25

Met Asn Arg Ile Lys Val Ala Ile Ile Phe Gly Gly Cys Ser Glu Glu
  1               5                  10                  15

His Asp Val Ser Val Lys Ser Ala Ile Glu Ile Ala Ala Asn Ile Asn
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Glu
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Val Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

```
Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Val Ala Ala Ala Gly Ile Thr Leu Pro Ala Leu Ile Asp Ser Leu Ile
                325                 330                 335

Thr Leu Ala Leu Lys Arg
            340
```

<210> SEQ ID NO 26
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 26

```
Met Asn Arg Ile Lys Val Ala Thr Ile Phe Gly Gly Cys Ser Glu Glu
  1               5                  10                  15

His Asp Val Ser Val Lys Ser Ala Ile Glu Ile Ala Ala Asn Ile Asp
            20                  25                  30

Thr Glu Lys Phe Asp Pro His Tyr Ile Gly Ile Thr Lys Asn Gly Val
        35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ala Gly Ser
                165                 170                 175

Ser Phe Gly Leu Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220
```

```
Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Met Ala Ala Ala Gly Ile Thr Leu Pro Ala Leu Ile Asp Ser Leu Ile
                325                 330                 335

Thr Leu Ala Leu Lys Arg
            340


<210> SEQ ID NO 27
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 27

Met Asn Arg Ile Lys Val Ala Thr Ile Phe Gly Gly Cys Ser Glu Glu
  1               5                  10                  15

His Asp Val Ser Val Lys Ser Ala Ile Glu Ile Ala Ala Asn Ile Asp
            20                  25                  30

Thr Glu Lys Phe Asp Pro His Tyr Ile Gly Ile Thr Lys Asn Gly Val
        35                  40                  45

Trp Lys Leu Cys Lys Lys Pro Cys Thr Glu Trp Glu Ala Asp Ser Leu
    50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Leu Thr Lys Val Asn Gly Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240
```

```
Arg Ile His Gln Glu Asn Glu Pro Glu Lys Gly Ser Glu Asn Ala Met
                245                 250                 255

Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Leu Pro Gly Phe Thr Ser Tyr Ser Arg Tyr Pro Arg Met
305                 310                 315                 320

Met Ala Ala Ala Gly Ile Thr Leu Pro Ala Met Ile Asp Ser Leu Ile
                325                 330                 335

Thr Leu Ala Leu Lys Arg
            340


<210> SEQ ID NO 28
<211> LENGTH: 342
<212> TYPE: PRT
<213> ORGANISM: Unknown
<220> FEATURE:
<223> OTHER INFORMATION: peptide from a microbial resistance gene

<400> SEQUENCE: 28

Met Asn Arg Ile Lys Val Ala Thr Ile Phe Gly Gly Cys Ser Glu Glu
  1               5                  10                  15

His Asp Val Ser Val Lys Ser Ala Ile Glu Ile Ala Ala Asn Ile Asp
             20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
     50                  55                  60

Pro Ala Ile Leu Ser Pro Asp Arg Lys Thr His Gly Leu Leu Val Met
 65                  70                  75                  80

Lys Glu Ser Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Val
            100                 105                 110

Leu Ser Gly Ile Pro Tyr Val Gly Cys Asp Ile Gln Ser Ser Ala Ala
        115                 120                 125

Cys Met Asp Lys Ser Leu Ala Tyr Ile Leu Thr Lys Asn Ala Gly Ile
    130                 135                 140

Ala Val Pro Glu Phe Gln Met Ile Asp Lys Gly Asp Lys Pro Glu Ala
145                 150                 155                 160

Gly Ala Leu Thr Tyr Pro Val Phe Val Lys Pro Ala Arg Ser Gly Ser
                165                 170                 175

Ser Phe Gly Val Thr Lys Val Asn Gly Pro Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255
```

```
Ile Thr Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
        275                 280                 285

Arg Val Asp Leu Phe Leu Gln Glu Asp Gly Gly Ile Val Leu Asn Glu
    290                 295                 300

Val Asn Thr Met Pro Gly Phe Thr Ser Tyr Ser Arg Tyr Pro Arg Met
305                 310                 315                 320

Val Ala Ala Ala Gly Ile Thr Leu Pro Ala Leu Ile Asp Ser Leu Ile
                325                 330                 335

Thr Leu Ala Leu Lys Arg
            340


<210> SEQ ID NO 29
<211> LENGTH: 10
<212> TYPE: PRT
<213> ORGANISM: Unknown
<220> FEATURE:
<223> OTHER INFORMATION: peptide from a microbial resistance gene

<400> SEQUENCE: 29

Phe Asp Pro His Tyr Ile Gly Ile Thr Lys
  1               5                   10


<210> SEQ ID NO 30
<211> LENGTH: 11
<212> TYPE: PRT
<213> ORGANISM: Unknown
<220> FEATURE:
<223> OTHER INFORMATION: peptide from a microbial resistance gene

<400> SEQUENCE: 30

Ile Asp Val Ala Phe Pro Val Leu His Gly Lys
  1               5                   10


<210> SEQ ID NO 31
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 31

Ile His Gln Glu Asn Glu Pro Glu Lys
  1               5


<210> SEQ ID NO 32
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 32

Leu Ser His Gly Ile Phe Arg
  1               5


<210> SEQ ID NO 33
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 33
```

Ser Leu Ala Tyr Ile Leu Thr Lys
1 5

<210> SEQ ID NO 34
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 34

Thr His Gly Leu Leu Val Met Lys
1 5

<210> SEQ ID NO 35
<211> LENGTH: 6
<212> TYPE: PRT
<213> ORGANISM: Unknown
<220> FEATURE:
<223> OTHER INFORMATION: peptide from a microbial resistance gene

<400> SEQUENCE: 35

Val Gln Glu Thr Ala Lys
1 5

<210> SEQ ID NO 36
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 36

Met Lys Lys Ile Ala Val Leu Phe Gly Gly Asn Ser Pro Glu Tyr Ser
1 5 10 15

Val Ser Leu Ala Ser Ala Ala Ser Val Ile Gln Ala Ile Asp Pro Leu
20 25 30

Lys Tyr Glu Val Met Thr Ile Gly Ile Ala Pro Thr Met Asp Trp Tyr
35 40 45

Leu Tyr Gln Gly Asn Leu Ala Asn Val Arg Asn Asp Thr Trp Leu Glu
50 55 60

Asp His Lys Asn Cys His Gln Leu Thr Phe Ser Ser Gln Gly Phe Ile
65 70 75 80

Leu Gly Glu Lys Arg Ile Val Pro Asp Val Leu Phe Pro Val Leu His
85 90 95

Gly Lys Tyr Gly Glu Asp Gly Cys Ile Gln Gly Leu Leu Glu Leu Met
100 105 110

Asn Leu Pro Tyr Val Gly Cys His Val Ala Ala Ser Ala Leu Cys Met
115 120 125

Asn Lys Trp Leu Leu His Gln Leu Ala Asp Thr Met Gly Ile Ala Ser
130 135 140

Ala Pro Thr Leu Leu Leu Ser Arg Tyr Glu Asn Asp Pro Ala Thr Ile
145 150 155 160

Asp Arg Phe Ile Gln Asp His Gly Phe Pro Ile Phe Ile Lys Pro Asn
165 170 175

Glu Ala Gly Ser Ser Lys Gly Ile Thr Lys Val Thr Asp Lys Thr Ala
180 185 190

Leu Gln Ser Ala Leu Thr Thr Ala Phe Ala Tyr Gly Ser Thr Val Leu
195 200 205

```
Ile Gln Lys Ala Ile Ala Gly Ile Glu Ile Gly Cys Gly Ile Leu Gly
    210                 215                 220

Asn Glu Gln Leu Thr Ile Gly Ala Cys Asp Ala Ile Ser Leu Val Asp
225                 230                 235                 240

Gly Phe Phe Asp Phe Glu Glu Lys Tyr Gln Leu Ile Ser Ala Thr Ile
                245                 250                 255

Thr Val Pro Ala Pro Leu Pro Leu Ala Leu Glu Ser Gln Ile Lys Glu
            260                 265                 270

Gln Ala Gln Leu Leu Tyr Arg Asn Leu Gly Leu Thr Gly Leu Ala Arg
        275                 280                 285

Ile Asp Phe Phe Val Thr Asn Gln Gly Ala Ile Tyr Leu Asn Glu Ile
    290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Gln Leu Ile Ala
                325                 330                 335

Leu Ala Glu Glu Asp Lys Arg
            340


<210> SEQ ID NO 37
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 37

Met Lys Lys Ile Ala Val Leu Phe Gly Gly Asn Ser Pro Glu Tyr Ser
  1               5                  10                  15

Val Ser Leu Ala Ser Ala Ala Ser Val Ile Gln Ala Ile Asp Pro Leu
             20                  25                  30

Lys Tyr Glu Val Met Thr Ile Gly Ile Ala Pro Thr Met Asp Trp Tyr
         35                  40                  45

Trp Tyr Gln Gly Asn Leu Ala Asn Val Arg Asn Asp Thr Trp Leu Glu
     50                  55                  60

Asp His Lys Asn Cys His Gln Leu Thr Phe Ser Ser Gln Gly Phe Ile
 65                  70                  75                  80

Leu Gly Glu Lys Arg Ile Val Pro Asp Val Leu Phe Pro Val Leu His
                 85                  90                  95

Gly Lys Tyr Gly Glu Asp Gly Cys Ile Gln Gly Leu Leu Glu Leu Met
            100                 105                 110

Asn Leu Pro Tyr Val Gly Cys His Val Ala Ala Ser Ala Leu Cys Met
        115                 120                 125

Asn Lys Trp Leu Leu His Gln Leu Ala Asp Thr Met Gly Ile Ala Ser
    130                 135                 140

Ala Pro Thr Leu Leu Leu Ser Arg Tyr Glu Asn Asp Pro Ala Thr Ile
145                 150                 155                 160

Asp Arg Phe Ile Gln Asp His Gly Phe Pro Ile Phe Ile Lys Pro Asn
                165                 170                 175

Glu Ala Gly Ser Ser Lys Gly Ile Thr Lys Val Thr Asp Lys Thr Ala
            180                 185                 190

Leu Gln Ser Ala Leu Thr Thr Ala Phe Ala Tyr Gly Ser Thr Val Leu
        195                 200                 205

Ile Gln Lys Ala Ile Ala Gly Ile Glu Ile Gly Cys Gly Ile Leu Gly
    210                 215                 220
```

```
Asn Glu Gln Leu Thr Ile Gly Ala Cys Asp Ala Ile Ser Leu Val Asp
225                 230                 235                 240

Gly Phe Phe Asp Phe Glu Glu Lys Tyr Gln Leu Ile Ser Ala Thr Ile
                245                 250                 255

Thr Val Pro Ala Pro Leu Pro Leu Ala Leu Glu Ser Gln Ile Lys Glu
            260                 265                 270

Gln Ala Gln Leu Leu Tyr Arg Asn Leu Gly Leu Thr Gly Leu Ala Arg
        275                 280                 285

Ile Asp Phe Phe Val Thr Asn Gln Gly Ala Ile Tyr Leu Asn Glu Ile
    290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Gln Leu Ile Ala
                325                 330                 335

Leu Ala Glu Glu Asp Lys Arg
            340


<210> SEQ ID NO 38
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 38

Met Lys Lys Ile Ala Val Leu Phe Gly Gly Asn Ser Pro Glu Tyr Ser
  1               5                  10                  15

Val Ser Leu Ala Ser Ala Ala Ser Val Ile Gln Ala Ile Asp Pro Leu
             20                  25                  30

Lys Tyr Glu Val Met Thr Ile Gly Ile Ala Pro Thr Met Asp Trp Tyr
         35                  40                  45

Trp Tyr Gln Gly Asn Leu Ala Asn Val Arg Asn Asp Thr Trp Leu Glu
     50                  55                  60

Asp His Lys Asn Cys His Gln Leu Thr Phe Ser Ser Gln Gly Phe Ile
 65                  70                  75                  80

Leu Gly Glu Lys Arg Ile Val Pro Asp Val Leu Phe Pro Val Leu His
                 85                  90                  95

Gly Lys Tyr Gly Glu Asp Gly Cys Ile Gln Gly Leu Leu Glu Leu Met
            100                 105                 110

Asn Leu Pro Tyr Val Gly Cys His Val Ala Ala Thr Ala Leu Cys Met
        115                 120                 125

Asn Lys Trp Leu Leu His Gln Leu Ala Asp Thr Met Gly Ile Ala Ser
    130                 135                 140

Ala Pro Thr Leu Leu Leu Ser Arg Tyr Glu Asn Asp Pro Ala Thr Ile
145                 150                 155                 160

Asp Arg Phe Ile Gln Asp His Gly Phe Pro Ile Phe Ile Lys Pro Asn
                165                 170                 175

Glu Ala Gly Ser Ser Lys Gly Ile Thr Lys Val Thr Asp Lys Thr Ala
            180                 185                 190

Leu Gln Ser Ala Leu Thr Thr Ala Phe Ala Tyr Gly Ser Thr Val Leu
        195                 200                 205

Ile Gln Lys Ala Ile Ala Gly Ile Glu Ile Gly Cys Gly Ile Leu Gly
    210                 215                 220

Asn Glu Gln Leu Thr Ile Gly Ala Cys Asp Ala Ile Ser Leu Val Asp
225                 230                 235                 240
```

Gly Phe Phe Asp Phe Glu Glu Lys Tyr Gln Leu Ile Ser Ala Thr Ile
245 250 255

Thr Val Pro Ala Pro Leu Pro Leu Ala Leu Glu Ser Gln Ile Lys Glu
260 265 270

Gln Ala Gln Leu Leu Tyr Arg Asn Leu Gly Leu Thr Gly Leu Ala Arg
275 280 285

Ile Asp Phe Phe Val Thr Asn Gln Gly Ala Ile Tyr Leu Asn Glu Ile
290 295 300

Asn Thr Met Pro Gly Phe Thr Gly His Ser Arg Tyr Pro Ala Met Met
305 310 315 320

Ala Glu Val Gly Leu Ser Tyr Glu Ile Leu Val Glu Gln Leu Ile Ala
325 330 335

Leu Ala Glu Glu Asp Lys Arg
340

<210> SEQ ID NO 39
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 39

Met Lys Lys Ile Ala Val Leu Phe Gly Gly Asn Ser Pro Glu Tyr Ser
1 5 10 15

Val Ser Leu Thr Ser Ala Ala Ser Val Ile Gln Ala Ile Asp Pro Leu
20 25 30

Lys Tyr Glu Val Met Thr Ile Gly Ile Ala Pro Thr Met Asp Trp Tyr
35 40 45

Trp Tyr Gln Gly Asn Leu Ala Asn Val Arg Asn Asp Thr Trp Leu Glu
50 55 60

Asp His Lys Asn Cys His Gln Leu Thr Phe Ser Ser Gln Gly Phe Ile
65 70 75 80

Leu Gly Glu Lys Arg Ile Val Pro Asp Val Leu Phe Pro Val Leu His
85 90 95

Gly Lys Tyr Gly Glu Asp Gly Cys Ile Gln Gly Leu Leu Glu Leu Met
100 105 110

Asn Leu Pro Tyr Val Gly Cys His Val Ala Ala Ser Ala Leu Cys Met
115 120 125

Asn Lys Trp Leu Leu His Gln Leu Ala Asp Thr Met Gly Ile Ala Ser
130 135 140

Ala Pro Thr Leu Leu Leu Ser Arg Tyr Glu Asn Asp Pro Ala Thr Ile
145 150 155 160

Asp Arg Phe Ile Gln Asp His Gly Phe Pro Ile Phe Ile Lys Pro Asn
165 170 175

Glu Ala Gly Ser Ser Lys Gly Ile Thr Lys Val Thr Asp Lys Thr Ala
180 185 190

Leu Gln Ser Ala Leu Thr Thr Ala Phe Ala Tyr Gly Ser Thr Val Leu
195 200 205

Ile Gln Lys Ala Ile Ala Gly Ile Glu Ile Gly Cys Gly Ile Leu Gly
210 215 220

Asn Glu Gln Leu Thr Ile Gly Ala Cys Asp Ala Ile Ser Leu Val Asp
225 230 235 240

Gly Phe Phe Asp Phe Glu Glu Lys Tyr Gln Leu Ile Ser Ala Thr Ile
245 250 255

```
Thr Val Pro Ala Pro Leu Pro Leu Ala Leu Glu Ser Gln Ile Lys Glu
            260                 265                 270

Gln Ala Gln Leu Leu Tyr Arg Asn Leu Gly Leu Thr Gly Leu Ala Arg
        275                 280                 285

Ile Asp Phe Phe Val Thr Asn Gln Gly Ala Ile Tyr Leu Asn Glu Ile
    290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Gln Leu Ile Ala
                325                 330                 335

Leu Ala Glu Glu Asp Lys Arg
            340


<210> SEQ ID NO 40
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 40

Met Lys Lys Ile Ala Val Leu Phe Gly Gly Asn Ser Pro Glu Tyr Ser
  1               5                  10                  15

Val Ser Leu Thr Ser Ala Ala Ser Val Ile Gln Ala Ile Asp Pro Leu
             20                  25                  30

Lys Tyr Glu Val Met Thr Ile Gly Ile Ala Pro Thr Met Asp Trp Tyr
         35                  40                  45

Trp Tyr Gln Gly Asn Leu Ala Asn Val Arg Asn Asp Thr Trp Leu Glu
     50                  55                  60

Asp His Lys Asn Cys His Gln Leu Thr Phe Ser Ser Gln Gly Phe Ile
 65                  70                  75                  80

Leu Gly Glu Lys Arg Ile Val Pro Asp Val Leu Phe Pro Val Leu His
                 85                  90                  95

Gly Lys Tyr Gly Glu Asp Gly Cys Ile Gln Gly Leu Leu Glu Leu Met
            100                 105                 110

Asn Leu Pro Tyr Val Gly Cys His Val Ala Ala Ser Ala Leu Cys Met
        115                 120                 125

Asn Lys Trp Leu Leu His Gln Leu Ala Asp Thr Met Gly Ile Ala Ser
    130                 135                 140

Ala Pro Thr Leu Leu Leu Ser Arg Tyr Glu Asn Asp Pro Ala Thr Ile
145                 150                 155                 160

Asp Arg Phe Ile Gln Asp His Gly Phe Pro Ile Phe Ile Lys Pro Asn
                165                 170                 175

Glu Ala Gly Ser Ser Lys Gly Ile Thr Lys Val Thr Asp Lys Thr Ala
            180                 185                 190

Leu Gln Ser Ala Leu Thr Thr Ala Phe Ala Tyr Gly Ser Thr Val Leu
        195                 200                 205

Ile Gln Lys Ala Ile Ala Gly Ile Glu Ile Gly Cys Gly Ile Leu Gly
    210                 215                 220

Asn Glu Gln Leu Thr Ile Gly Ala Cys Asp Ala Ile Ser Leu Val Asp
225                 230                 235                 240

Gly Phe Phe Asp Phe Glu Glu Lys Tyr Gln Leu Ile Ser Ala Thr Ile
                245                 250                 255

Thr Val Pro Ala Pro Leu Pro Leu Ala Leu Glu Ser Gln Ile Lys Glu
            260                 265                 270
```

-continued

```
Gln Ala Gln Leu Leu Tyr Arg Asn Leu Gly Leu Thr Gly Leu Ala Arg
        275                 280                 285

Ile Asp Phe Phe Val Thr Asn Gln Gly Ala Ile Tyr Leu Asn Glu Ile
    290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Lys Leu Ile Ala
                325                 330                 335

Leu Ala Glu Glu Asp Lys Arg
            340


<210> SEQ ID NO 41
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 41

Met Lys Lys Ile Ala Val Leu Phe Gly Gly Asn Ser Pro Glu Tyr Ser
  1               5                  10                  15

Val Ser Leu Thr Ser Ala Glu Ser Val Ile Gln Ala Ile Asn Pro Leu
            20                  25                  30

Lys Tyr Glu Val Met Thr Ile Gly Ile Ala Pro Thr Met Asp Trp Tyr
        35                  40                  45

Trp Tyr Gln Gly Asn Leu Ala Asn Val Arg Asn Asp Thr Trp Leu Glu
     50                  55                  60

Asp His Lys Asn Cys His Gln Leu Thr Phe Ser Ser Gln Gly Phe Ile
 65                  70                  75                  80

Leu Gly Glu Lys Arg Ile Val Pro Asp Val Leu Phe Pro Val Leu His
                 85                  90                  95

Gly Lys Tyr Gly Glu Asp Gly Cys Ile Gln Gly Leu Leu Glu Leu Met
            100                 105                 110

Asn Leu Pro Tyr Val Gly Cys His Val Ala Ala Ser Ala Leu Cys Met
        115                 120                 125

Asn Lys Trp Leu Leu His Gln Leu Ala Asp Thr Met Gly Ile Ala Ser
    130                 135                 140

Ala Pro Thr Leu Leu Leu Ser Arg Tyr Glu Asn Asp Pro Ala Thr Ile
145                 150                 155                 160

Asp Arg Phe Ile Gln Asp His Gly Phe Pro Ile Phe Ile Lys Pro Asn
                165                 170                 175

Glu Ala Gly Ser Ser Lys Gly Ile Thr Lys Val Thr Asp Lys Thr Ala
            180                 185                 190

Leu Gln Ser Ala Leu Thr Thr Ala Phe Ala Tyr Gly Ser Thr Val Leu
        195                 200                 205

Ile Gln Lys Ala Ile Ala Gly Ile Glu Ile Gly Cys Gly Ile Leu Gly
    210                 215                 220

Asn Glu Gln Leu Thr Ile Gly Ala Cys Asp Ala Ile Ser Leu Val Asp
225                 230                 235                 240

Gly Phe Phe Asp Phe Glu Glu Lys Tyr Gln Leu Ile Ser Ala Thr Ile
                245                 250                 255

Thr Val Pro Ala Pro Leu Pro Leu Ala Leu Glu Ser Gln Ile Lys Glu
            260                 265                 270

Gln Ala Gln Leu Leu Tyr Arg Asn Leu Gly Leu Thr Gly Leu Ala Arg
        275                 280                 285
```

```
Ile Asp Phe Phe Val Thr Asn Gln Gly Ala Ile Tyr Leu Asn Glu Ile
    290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Gln Leu Ile Ala
                325                 330                 335

Leu Ala Glu Glu Asp Lys Arg
            340


<210> SEQ ID NO 42
<211> LENGTH: 344
<212> TYPE: PRT
<213> ORGANISM: Unknown
<220> FEATURE:
<223> OTHER INFORMATION: peptide from a microbial resistance gene

<400> SEQUENCE: 42

Met Met Lys Lys Ile Ala Val Leu Phe Gly Gly Asn Ser Pro Glu Tyr
  1               5                  10                  15

Ser Val Ser Leu Ala Ser Ala Ala Ser Val Ile Gln Ala Ile Asp Pro
             20                  25                  30

Leu Lys Tyr Glu Val Met Thr Ile Gly Ile Ala Pro Thr Met Asp Trp
         35                  40                  45

Tyr Trp Tyr Gln Gly Asn Leu Ala Asn Val Arg Asn Asp Thr Trp Leu
     50                  55                  60

Glu Asp His Lys Asn Cys His Gln Leu Thr Phe Ser Ser Gln Gly Phe
 65                  70                  75                  80

Ile Leu Gly Glu Lys Arg Ile Val Pro Asp Val Leu Phe Pro Val Leu
                 85                  90                  95

His Gly Lys Tyr Gly Glu Asp Gly Cys Ile Gln Gly Leu Leu Glu Leu
            100                 105                 110

Met Asn Leu Pro Tyr Val Gly Cys His Val Ala Ala Ser Ala Leu Cys
        115                 120                 125

Met Asn Lys Trp Leu Leu His Gln Leu Ala Asp Thr Met Gly Ile Ala
    130                 135                 140

Ser Ala Pro Thr Leu Leu Leu Ser Arg Tyr Glu Asn Asp Pro Ala Thr
145                 150                 155                 160

Ile Asp Arg Phe Ile Gln Asp His Gly Phe Pro Ile Phe Ile Lys Pro
                165                 170                 175

Asn Glu Ala Gly Ser Ser Lys Gly Ile Thr Lys Val Thr Asp Lys Thr
            180                 185                 190

Ala Leu Gln Ser Ala Leu Thr Thr Ala Phe Ala Tyr Gly Ser Thr Val
        195                 200                 205

Leu Ile Gln Lys Ala Ile Ala Gly Ile Glu Ile Gly Cys Gly Ile Leu
    210                 215                 220

Gly Asn Glu Gln Leu Thr Ile Gly Ala Cys Asp Ala Ile Ser Leu Val
225                 230                 235                 240

Asp Gly Phe Phe Asp Phe Glu Glu Lys Tyr Gln Leu Ile Ser Ala Thr
                245                 250                 255

Ile Thr Val Pro Ala Pro Leu Pro Leu Ala Leu Glu Ser Gln Ile Lys
            260                 265                 270

Glu Gln Ala Gln Leu Leu Tyr Arg Asn Leu Gly Leu Thr Gly Leu Ala
        275                 280                 285

Arg Ile Asp Phe Phe Val Thr Asn Gln Gly Ala Ile Tyr Leu Asn Glu
    290                 295                 300
```

-continued

```
Ile Asn Thr Met Pro Gly Phe Thr Gly His Ser Arg Tyr Pro Ala Met
305                 310                 315                 320

Met Ala Glu Val Gly Leu Ser Tyr Glu Ile Leu Val Glu Gln Leu Ile
                325                 330                 335

Ala Leu Ala Glu Glu Asp Lys Arg
            340


<210> SEQ ID NO 43
<211> LENGTH: 344
<212> TYPE: PRT
<213> ORGANISM: Unknown
<220> FEATURE:
<223> OTHER INFORMATION: peptide from a microbial resistance gene

<400> SEQUENCE: 43

Met Met Lys Lys Ile Ala Val Leu Phe Gly Gly Asn Ser Pro Glu Tyr
  1               5                  10                  15

Ser Val Ser Leu Thr Ser Ala Ala Ser Val Ile Gln Ala Ile Asp Pro
            20                  25                  30

Leu Lys Tyr Glu Val Met Thr Ile Gly Ile Ala Pro Thr Met Asp Trp
        35                  40                  45

Tyr Trp Tyr Gln Gly Asn Leu Ala Asn Val Arg Asn Asp Thr Trp Leu
    50                  55                  60

Glu Asp His Lys Asn Cys His Gln Leu Thr Phe Ser Ser Gln Gly Phe
 65                  70                  75                  80

Ile Leu Gly Glu Lys Arg Ile Val Pro Asp Val Leu Phe Pro Val Leu
                85                  90                  95

His Gly Lys Tyr Gly Glu Asp Gly Cys Ile Gln Gly Leu Leu Glu Leu
            100                 105                 110

Met Asn Leu Pro Tyr Val Gly Cys His Val Ala Ala Ser Ala Leu Cys
        115                 120                 125

Met Asn Lys Trp Leu Leu His Gln Leu Ala Asp Thr Met Gly Ile Ala
    130                 135                 140

Ser Ala Pro Thr Leu Leu Leu Ser Arg Tyr Glu Asn Asp Pro Ala Thr
145                 150                 155                 160

Ile Asp Arg Phe Ile Gln Asp His Gly Phe Pro Ile Phe Ile Lys Pro
                165                 170                 175

Asn Glu Ala Gly Ser Ser Lys Gly Ile Thr Lys Val Thr Asp Lys Thr
            180                 185                 190

Ala Leu Gln Ser Ala Leu Thr Thr Ala Phe Ala Tyr Gly Ser Thr Val
        195                 200                 205

Leu Ile Gln Lys Ala Ile Ala Gly Ile Glu Ile Gly Cys Gly Ile Leu
    210                 215                 220

Gly Asn Glu Gln Leu Thr Ile Gly Ala Cys Asp Ala Ile Ser Leu Val
225                 230                 235                 240

Asp Gly Phe Phe Asp Phe Glu Glu Lys Tyr Gln Leu Ile Ser Ala Thr
                245                 250                 255

Ile Thr Val Pro Ala Pro Leu Pro Leu Ala Leu Glu Ser Gln Ile Lys
            260                 265                 270

Glu Gln Ala Gln Leu Leu Tyr Arg Asn Leu Gly Leu Thr Gly Leu Ala
        275                 280                 285

Arg Ile Asp Phe Phe Val Thr Asn Gln Gly Ala Ile Tyr Leu Asn Glu
    290                 295                 300

Ile Asn Thr Met Pro Gly Phe Thr Gly His Ser Arg Tyr Pro Ala Met
305                 310                 315                 320
```

Met Ala Glu Val Gly Leu Ser Tyr Glu Ile Leu Val Glu Gln Leu Ile
325 330 335

Ala Leu Ala Glu Glu Asp Lys Arg
340

<210> SEQ ID NO 44
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 44

Met Lys Lys Ile Ala Ile Ile Phe Gly Gly Asn Ser Pro Glu Tyr Ala
1 5 10 15

Val Ser Leu Ala Ser Ala Thr Ser Ala Ile Glu Ala Leu Gln Ser Ser
20 25 30

Pro Asp Asp Tyr Asp Leu Ser Leu Ile Gly Ile Ala Pro Asp Ala Met
35 40 45

Asp Trp Tyr Leu Tyr Thr Gly Glu Leu Glu Asn Ile Arg Gln Asp Thr
50 55 60

Trp Leu Leu Asp Thr Lys His Lys Gln Lys Ile Gln Pro Leu Phe Glu
65 70 75 80

Gly Asn Gly Phe Trp Leu Ser Glu Ala Gln Gln Thr Leu Val Pro Asp
85 90 95

Val Leu Phe Pro Ile Met His Gly Lys Tyr Gly Glu Asp Gly Ser Ile
100 105 110

Gln Gly Leu Phe Glu Leu Met Lys Leu Pro Tyr Val Gly Cys Gly Val
115 120 125

Ala Ala Ser Ala Leu Cys Met Asn Lys Trp Leu Leu His Gln Ala Ala
130 135 140

Ala Ala Ile Gly Val Gln Ser Ala Pro Thr Ile Leu Leu Thr Asn Gln
145 150 155 160

Ala Asn Gln Gln Asp Gln Ile Glu Ala Phe Ile Gln Thr His Gly Phe
165 170 175

Pro Val Phe Phe Lys Pro Asn Glu Ala Gly Ser Ser Lys Gly Ile Thr
180 185 190

Lys Val Thr Cys Val Glu Glu Ile Ala Ser Ala Leu Lys Glu Ala Phe
195 200 205

Thr Tyr Cys Ser Ala Val Leu Leu Gln Lys Asn Ile Ala Gly Val Glu
210 215 220

Ile Gly Cys Gly Ile Leu Gly Asn Asp Ser Leu Thr Val Gly Ala Cys
225 230 235 240

Asp Ala Ile Ser Leu Val Asp Gly Phe Phe Asp Phe Glu Glu Lys Tyr
245 250 255

Gln Leu Ile Ser Ala Lys Ile Thr Val Pro Ala Pro Leu Pro Glu Thr
260 265 270

Ile Glu Thr Lys Val Lys Glu Gln Ala Gln Leu Leu Tyr His Ser Leu
275 280 285

Gly Leu Lys Gly Leu Ala Arg Ile Asp Phe Phe Val Thr Asp Gln Gly
290 295 300

Glu Leu Tyr Leu Asn Glu Ile Asn Thr Met Pro Gly Phe Thr Ser His
305 310 315 320

Ser Arg Tyr Pro Ala Met Met Ala Ala Ile Gly Leu Ser Tyr Gln Glu
325 330 335

```
Leu Leu Gln Lys Leu Leu Val Leu Ala Lys Glu Glu Val Lys
            340                 345                 350


<210> SEQ ID NO 45
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 45

Met Lys Lys Ile Ala Ile Ile Phe Gly Gly Asn Ser Pro Glu Tyr Ala
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Ala Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Ala Ser Ala Leu Cys Met Asn Lys Trp Leu Leu His Gln Ala Ala
    130                 135                 140

Glu Ala Ile Gly Val Gln Ser Ala Pro Thr Ile Leu Leu Thr Asn Gln
145                 150                 155                 160

Asp Asn Gln Gln Arg Gln Ile Glu Ala Phe Ile Gln Thr His Asp Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Pro Ala Leu Lys Glu Ala Phe
        195                 200                 205

Ala Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Glu Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr His Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Ile Gly Leu Ser Tyr Gln Glu
                325                 330                 335

Leu Leu Gln Lys Leu Leu Val Leu Ala Lys Glu Glu Gly Lys
            340                 345                 350
```

```
<210> SEQ ID NO 46
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 46

Met Lys Lys Ile Ala Ile Ile Phe Gly Gly Asn Ser Pro Glu Tyr Ala
  1               5                  10                  15

Val Ser Leu Ala Ser Ala Thr Ser Ala Leu Glu Ala Leu Gln Ser Ser
             20                  25                  30

Pro Tyr Asp Tyr Asp Leu Ser Leu Ile Gly Ile Ala Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350


<210> SEQ ID NO 47
<211> LENGTH: 350
```

<212> TYPE: PRT
<213> ORGANISM: Unknown
<220> FEATURE:
<223> OTHER INFORMATION: peptide from a microbial resistance gene

<400> SEQUENCE: 47

```
Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Ala Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350
```

<210> SEQ ID NO 48
<211> LENGTH: 350
<212> TYPE: PRT
<213> ORGANISM: Unknown
<220> FEATURE:

```
<223> OTHER INFORMATION: peptide from a microbial resistance gene

<400> SEQUENCE: 48

Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Ala Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Glu Arg Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350


<210> SEQ ID NO 49
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 49
```

```
Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
            20                  25                  30

Pro Tyr Asp Tyr Asp Leu Ser Leu Ile Gly Ile Ala Pro Asp Ala Met
        35                  40                  45

Asp Trp Tyr Leu Tyr Thr Gly Glu Leu Glu Asn Ile Arg Gln Asp Thr
    50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Val Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350


<210> SEQ ID NO 50
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 50

Met Lys Lys Ile Ala Ile Ile Phe Gly Gly Asn Ser Pro Glu Tyr Thr
  1               5                  10                  15
```

```
Val Ser Leu Ala Ser Ala Thr Ser Ala Ile Glu Ala Leu Gln Ser Ser
            20                  25                  30

Pro Tyr Asp Tyr Asp Leu Ser Leu Ile Gly Ile Ala Pro Asp Ala Met
        35                  40                  45

Asp Trp Tyr Leu Tyr Thr Gly Glu Leu Glu Asn Ile Arg Gln Asp Thr
    50                  55                  60

Trp Leu Leu Asp Thr Lys His Lys Gln Lys Ile Gln Pro Leu Phe Glu
65                  70                  75                  80

Gly Asn Gly Phe Trp Leu Ser Glu Glu Gln Gln Thr Leu Val Pro Asp
                85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Ser Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Val Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Glu Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Ile Leu Ala Lys Glu Glu Val Lys
            340                 345                 350
```

<210> SEQ ID NO 51
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 51

```
Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
            20                  25                  30
```

```
Pro Tyr Asp Tyr Asp Leu Ser Leu Ile Gly Ile Ala Pro Asp Ala Met
        35                  40                  45

Asp Trp Tyr Leu Tyr Thr Gly Glu Leu Glu Asn Ile Arg Gln Asp Thr
    50                  55                  60

Trp Leu Leu Asp Thr Lys His Thr Gln Lys Ile Lys Pro Leu Phe Glu
65                  70                  75                  80

Gly Asn Gly Phe Trp Leu Ser Glu Glu Gln Gln Thr Leu Val Pro Asp
                85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350


<210> SEQ ID NO 52
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 52

Met Lys Lys Ile Ala Ile Ile Phe Gly Gly Asn Ser Pro Glu Tyr Thr
1               5                   10                  15

Val Ser Leu Ala Ser Ala Thr Ser Ala Ile Glu Ala Leu Gln Ser Ser
            20                  25                  30

Pro Tyr Asp Tyr Asp Leu Ser Leu Ile Gly Ile Ala Pro Asp Ala Met
        35                  40                  45
```

Asp Trp Tyr Leu Tyr Thr Gly Glu Leu Glu Asn Ile Arg Gln Asp Thr
50 55 60

Trp Leu Leu Asp Thr Lys His Thr Gln Lys Ile Gln Pro Leu Phe Glu
65 70 75 80

Gly Asn Gly Phe Trp Ile Ser Glu Ala Gln Gln Thr Leu Val Pro Asp
85 90 95

Val Leu Phe Pro Ile Met His Gly Lys Tyr Gly Glu Asp Gly Ser Ile
100 105 110

Gln Gly Met Phe Glu Leu Met Lys Leu Pro Tyr Val Gly Cys Gly Val
115 120 125

Ala Ala Ser Ala Leu Cys Met Asn Lys Trp Leu Leu His Gln Ala Ala
130 135 140

Ala Ala Ile Gly Val Gln Ser Ala Pro Thr Ile Leu Leu Thr Asn Gln
145 150 155 160

Ala Asn Gln Gln Arg Gln Ile Glu Ala Phe Ile Gln Thr His Gly Phe
165 170 175

Pro Val Phe Phe Lys Pro Asn Glu Ala Gly Ser Ser Lys Gly Ile Thr
180 185 190

Lys Val Thr Cys Val Glu Glu Ile Ala Pro Ala Leu Lys Glu Ala Phe
195 200 205

Ala Tyr Cys Ser Ala Val Leu Leu Gln Lys Asn Ile Ala Gly Val Glu
210 215 220

Ile Gly Cys Gly Ile Leu Gly Asn Asp Ser Leu Thr Val Gly Ala Cys
225 230 235 240

Asp Ala Ile Ser Leu Val Asp Gly Phe Phe Asp Phe Glu Glu Lys Tyr
245 250 255

Gln Leu Ile Ser Ala Lys Ile Thr Val Pro Ala Pro Leu Pro Glu Thr
260 265 270

Ile Glu Thr Lys Val Lys Glu Gln Ala Gln Leu Leu Tyr His Ser Leu
275 280 285

Gly Leu Lys Gly Leu Ala Arg Ile Asp Phe Phe Val Thr Asp Gln Gly
290 295 300

Glu Leu Tyr Leu Asn Glu Ile Asn Thr Met Pro Gly Phe Thr Ser His
305 310 315 320

Ser Arg Tyr Pro Ala Met Met Ala Ala Val Gly Leu Ser Tyr Gln Glu
325 330 335

Leu Leu Gln Lys Leu Leu Val Leu Ala Lys Glu Glu Gly Lys
340 345 350

<210> SEQ ID NO 53
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 53

Met Lys Lys Ile Ala Ile Ile Phe Gly Gly Asn Ser Pro Glu Tyr Thr
1 5 10 15

Val Ser Leu Ala Ser Ala Thr Ser Ala Ile Glu Ala Leu Gln Ser Ser
20 25 30

Pro Tyr Asp Tyr Asp Leu Ser Leu Ile Gly Ile Ala Pro Asp Ala Met
35 40 45

Asp Trp Tyr Leu Tyr Thr Gly Glu Leu Glu Asn Ile Arg Gln Asp Thr
50 55 60

Trp Leu Leu Asp Thr Lys Gln Lys Gln Lys Ile Gln Pro Leu Phe Glu
65 70 75 80

Gly Asn Gly Phe Trp Leu Ser Glu Glu Gln Gln Thr Leu Val Pro Asp
85 90 95

Val Leu Phe Pro Ile Met His Gly Lys Tyr Gly Glu Asp Gly Ser Ile
100 105 110

Gln Gly Leu Phe Glu Leu Met Lys Leu Pro Tyr Val Gly Cys Gly Val
115 120 125

Ala Gly Ser Ala Leu Cys Met Asn Lys Trp Leu Leu His Gln Ala Ala
130 135 140

Ala Ala Ile Gly Val Gln Ser Ala Pro Thr Ile Leu Leu Thr Asn His
145 150 155 160

Ala Asn Gln Gln Glu Gln Ile Glu Ala Phe Ile Gln Thr His Gly Phe
165 170 175

Pro Val Phe Phe Lys Pro Asn Glu Ala Gly Ser Ser Lys Gly Ile Thr
180 185 190

Lys Val Thr Cys Val Glu Glu Ile Ala Ser Ala Leu Lys Glu Ala Phe
195 200 205

Thr Tyr Cys Ser Ala Val Leu Leu Gln Lys Asn Ile Ala Gly Val Glu
210 215 220

Ile Gly Cys Gly Ile Leu Gly Asn Asp Ser Leu Thr Val Gly Ala Cys
225 230 235 240

Asp Ala Ile Ser Leu Val Asp Gly Phe Phe Asp Phe Glu Glu Lys Tyr
245 250 255

Gln Leu Ile Ser Ala Lys Ile Thr Val Pro Ala Pro Leu Pro Glu Thr
260 265 270

Ile Glu Thr Lys Val Lys Glu Gln Ala Gln Leu Leu Tyr Arg Ser Leu
275 280 285

Gly Leu Lys Gly Leu Ala Arg Ile Asp Phe Phe Val Thr Asp Gln Gly
290 295 300

Glu Leu Tyr Leu Asn Glu Ile Asn Thr Met Pro Gly Phe Thr Ser His
305 310 315 320

Ser Arg Tyr Pro Ala Met Met Ala Ala Val Gly Leu Ser Tyr Gln Glu
325 330 335

Leu Leu Gln Lys Leu Leu Val Leu Ala Lys Glu Glu Val Lys
340 345 350

<210> SEQ ID NO 54
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 54

Met Lys Lys Ile Ala Ile Ile Phe Gly Gly Asn Ser Pro Glu Tyr Thr
1 5 10 15

Val Ser Leu Ala Ser Ala Thr Ser Ala Ile Glu Ala Leu Gln Ser Ser
20 25 30

Pro Tyr Asp Tyr Asp Leu Ser Leu Ile Gly Ile Ala Pro Asp Ala Met
35 40 45

Asp Trp Tyr Leu Tyr Thr Gly Glu Leu Glu Asn Ile Arg Gln Asp Thr
50 55 60

Trp Leu Leu Asp Thr Lys Gln Lys Gln Lys Ile Gln Pro Leu Phe Glu
65 70 75 80

```
Gly Asn Gly Phe Trp Leu Ser Glu Glu Gln Gln Thr Leu Val Pro Asp
                85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Ser Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Val Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Glu Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Ile Leu Ala Lys Glu Glu Val Lys
            340                 345                 350
```

<210> SEQ ID NO 55
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 55

```
Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Ala Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys Gln Lys Gln Lys Ile Gln Pro Leu Phe Glu
 65                  70                  75                  80

Gly Asn Gly Phe Trp Leu Ser Glu Glu Gln Gln Thr Leu Val Pro Asp
                85                  90                  95
```

```
Val Leu Phe Pro Ile Met His Gly Lys Tyr Gly Glu Asp Gly Ser Ile
            100                 105                 110

Gln Gly Met Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn His
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350


<210> SEQ ID NO 56
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 56

Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Thr Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110
```

```
Gln Gly Leu Phe Glu Leu Met Lys Leu Pro Tyr Val Gly Cys Gly Val
        115                 120                 125

Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350


<210> SEQ ID NO 57
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 57

Met Lys Lys Ile Ala Ile Ile Phe Gly Gly Asn Ser Pro Glu Tyr Thr
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Thr Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Lys Gln Lys Ile Gln Pro Leu Phe Glu
 65                  70                  75                  80

Gly Asn Gly Phe Trp Leu Ser Glu Glu Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125
```

```
Ala Gly Ser Ala Leu Cys Met Asn Lys Trp Leu Leu His Gln Ala Ala
    130                 135                 140

Ala Ala Ile Gly Val Gln Ser Ala Pro Thr Ile Leu Leu Thr Asn Gln
145                 150                 155                 160

Ala Asn Gln Gln Glu Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Ser Ala Leu Lys Glu Ala Phe
        195                 200                 205

Thr Tyr Cys Ser Ala Val Leu Leu Gln Lys Asn Ile Val Gly Val Glu
    210                 215                 220

Ile Gly Cys Gly Ile Leu Gly Asn Asp Ser Leu Thr Val Gly Ala Cys
225                 230                 235                 240

Asp Thr Ile Ser Leu Val Asp Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr Arg Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Val Gly Leu Ser Tyr Gln Glu
                325                 330                 335

Leu Leu Gln Lys Leu Leu Val Leu Ala Lys Glu Glu Val Lys
            340                 345                 350
```

<210> SEQ ID NO 58
<211> LENGTH: 350
<212> TYPE: PRT
<213> ORGANISM: Unknown
<220> FEATURE:
<223> OTHER INFORMATION: peptide from a microbial resistance gene

<400> SEQUENCE: 58

```
Met Lys Lys Ile Ala Ile Ile Phe Gly Gly Asn Ser Ser Glu Tyr Thr
  1               5                  10                  15

Val Ser Leu Ala Ser Ala Thr Ser Ala Ile Glu Ala Leu Gln Ser Ser
             20                  25                  30

Pro Tyr Asp Tyr Asp Leu Ser Leu Ile Gly Ile Ala Pro Asp Ala Met
         35                  40                  45

Asp Trp Tyr Leu Tyr Thr Gly Glu Leu Glu Asn Ile Arg Gln Asp Thr
     50                  55                  60

Trp Leu Leu Asp Thr Lys His Thr Gln Lys Ile Gln Pro Leu Phe Glu
 65                  70                  75                  80

Glu Asn Gly Phe Trp Leu Ser Glu Ala Gln Gln Thr Leu Val Pro Asp
                 85                  90                  95

Val Leu Phe Pro Ile Met His Gly Lys Tyr Gly Glu Asp Gly Ser Ile
            100                 105                 110

Gln Gly Leu Phe Glu Leu Met Lys Leu Pro Tyr Val Gly Cys Gly Val
        115                 120                 125

Ala Ala Ser Ala Leu Cys Met Asn Lys Trp Leu Leu His Gln Ala Ala
    130                 135                 140
```

```
Ala Ala Ile Gly Val Gln Ser Ala Pro Thr Ile Leu Leu Thr Asn Gln
145                 150                 155                 160

Asp Asn Gln Gln Gln Gln Ile Glu Ala Phe Ile Gln Thr His Gly Phe
                165                 170                 175

Pro Val Phe Phe Lys Pro Asn Glu Ala Gly Ser Ser Lys Gly Ile Thr
            180                 185                 190

Lys Val Thr Cys Val Glu Glu Ile Ala Pro Ala Leu Lys Glu Ala Phe
        195                 200                 205

Ala Tyr Cys Ser Ala Val Leu Leu Gln Lys Asn Ile Ala Gly Val Glu
    210                 215                 220

Ile Gly Cys Gly Ile Leu Gly Asn Asp Ser Leu Thr Val Gly Ala Cys
225                 230                 235                 240

Asp Ala Ile Ser Leu Val Glu Gly Phe Phe Asp Phe Glu Glu Lys Tyr
                245                 250                 255

Gln Leu Ile Ser Ala Lys Ile Thr Val Pro Ala Pro Leu Pro Glu Thr
            260                 265                 270

Ile Glu Thr Lys Val Lys Glu Gln Ala Gln Leu Leu Tyr His Ser Leu
        275                 280                 285

Gly Leu Lys Gly Leu Ala Arg Ile Asp Phe Phe Val Thr Asp Gln Gly
    290                 295                 300

Glu Leu Tyr Leu Asn Glu Ile Asn Thr Met Pro Gly Phe Thr Ser His
305                 310                 315                 320

Ser Arg Tyr Pro Ala Met Met Ala Ala Ile Gly Leu Ser Tyr Gln Glu
                325                 330                 335

Leu Leu Gln Lys Leu Leu Val Leu Ala Lys Glu Glu Gly Lys
            340                 345                 350


<210> SEQ ID NO 59
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 59

Glu Gln Ala Gln Leu Leu Tyr Arg
  1               5


<210> SEQ ID NO 60
<211> LENGTH: 20
<212> TYPE: PRT
<213> ORGANISM: Unknown
<220> FEATURE:
<223> OTHER INFORMATION: peptide from a microbial resistance gene

<400> SEQUENCE: 60

Phe Ile Gln Asp His Gly Phe Pro Ile Phe Ile Lys Pro Asn Glu Ala
  1               5                  10                  15

Gly Ser Ser Lys
             20


<210> SEQ ID NO 61
<211> LENGTH: 13
<212> TYPE: PRT
<213> ORGANISM: Unknown
<220> FEATURE:
<223> OTHER INFORMATION: peptide from a microbial resistance gene

<400> SEQUENCE: 61
```

-continued

Ile Val Pro Asp Val Leu Phe Pro Val Leu His Gly Lys
1 5 10

<210> SEQ ID NO 62
<211> LENGTH: 17
<212> TYPE: PRT
<213> ORGANISM: Unknown
<220> FEATURE:
<223> OTHER INFORMATION: peptide from a microbial resistance gene

<400> SEQUENCE: 62

Asn Cys His Gln Leu Thr Phe Ser Ser Gln Gly Phe Ile Leu Gly Glu
1 5 10 15

Lys

<210> SEQ ID NO 63
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 63

Asn Asp Thr Trp Leu Glu Asp His Lys
1 5

<210> SEQ ID NO 64
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 64

Asn Leu Gly Leu Thr Gly Leu Ala Arg
1 5

<210> SEQ ID NO 65
<211> LENGTH: 21
<212> TYPE: PRT
<213> ORGANISM: Unknown
<220> FEATURE:
<223> OTHER INFORMATION: peptide from a microbial resistance gene

<400> SEQUENCE: 65

Thr Ala Leu Gln Ser Ala Leu Thr Thr Ala Phe Ala Tyr Gly Ser Thr
1 5 10 15

Val Leu Ile Gln Lys
20

<210> SEQ ID NO 66
<211> LENGTH: 22
<212> TYPE: PRT
<213> ORGANISM: Unknown
<220> FEATURE:
<223> OTHER INFORMATION: peptide from a microbial resistance gene

<400> SEQUENCE: 66

Trp Leu Leu His Gln Leu Ala Asp Thr Met Gly Ile Ala Ser Ala Pro
1 5 10 15

Thr Leu Leu Leu Ser Arg
20

<210> SEQ ID NO 67
<211> LENGTH: 10

<212> TYPE: PRT
<213> ORGANISM: Unknown
<220> FEATURE:
<223> OTHER INFORMATION: peptide from a microbial resistance gene

<400> SEQUENCE: 67

Tyr Glu Asn Asp Pro Ala Thr Ile Asp Arg
1 5 10

<210> SEQ ID NO 68
<211> LENGTH: 23
<212> TYPE: PRT
<213> ORGANISM: Unknown
<220> FEATURE:
<223> OTHER INFORMATION: peptide from a microbial resistance gene

<400> SEQUENCE: 68

Tyr Gln Leu Ile Ser Ala Thr Ile Thr Val Pro Ala Pro Leu Pro Leu
1 5 10 15

Ala Leu Glu Ser Gln Ile Lys
20

<210> SEQ ID NO 69
<211> LENGTH: 14
<212> TYPE: PRT
<213> ORGANISM: Unknown
<220> FEATURE:
<223> OTHER INFORMATION: peptide from a microbial resistance gene

<400> SEQUENCE: 69

Ile Thr Val Pro Ala Pro Leu Pro Glu Thr Ile Glu Thr Lys
1 5 10

<210> SEQ ID NO 70
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 70

Gln Asp Thr Trp Leu Leu Asp Thr Lys
1 5

<210> SEQ ID NO 71
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 71

Tyr Gln Leu Ile Ser Ala Lys
1 5

<210> SEQ ID NO 72
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 72

Met Phe Lys Ile Lys Val Ala Val Leu Phe Gly Gly Cys Ser Glu Glu
1 5 10 15

His Asn Val Ser Ile Lys Ser Ala Met Glu Ile Ala Ala Asn Ile Asp

-continued

```
            20                  25                  30

Thr Lys Lys Tyr Gln Pro Tyr Tyr Ile Gly Ile Thr Lys Ser Gly Val
        35                  40                  45

Trp Lys Met Cys Glu Lys Pro Cys Leu Glu Trp Glu Gln Tyr Ala Gly
    50                  55                  60

Asp Pro Val Val Phe Ser Pro Asp Arg Ser Thr His Gly Leu Leu Ile
65                  70                  75                  80

Gln Lys Asp Lys Gly Tyr Glu Ile Gln Pro Val Asp Val Val Leu Pro
                85                  90                  95

Met Ile His Gly Lys Phe Gly Glu Asp Gly Ser Ile Gln Gly Leu Leu
            100                 105                 110

Glu Leu Ser Gly Ile Pro Tyr Val Gly Cys Asp Ile Gln Ser Ser Val
        115                 120                 125

Thr Cys Met Asp Lys Ala Leu Ala Tyr Thr Val Val Lys Asn Ala Gly
    130                 135                 140

Ile Ala Val Pro Gly Phe Arg Ile Leu Gln Glu Gly Asp Arg Leu Glu
145                 150                 155                 160

Thr Glu Asp Phe Val Tyr Pro Val Phe Val Lys Pro Ala Arg Ser Gly
                165                 170                 175

Ser Ser Phe Gly Val Asn Lys Val Cys Lys Ala Glu Glu Leu Gln Ala
            180                 185                 190

Ala Ile Glu Glu Ala Arg Lys Tyr Asp Ser Lys Ile Leu Ile Glu Glu
        195                 200                 205

Ala Val Thr Gly Ser Glu Val Gly Cys Ala Ile Leu Gly Asn Gly Asn
    210                 215                 220

Asp Leu Met Ala Gly Glu Val Asp Gln Ile Glu Leu Arg His Gly Phe
225                 230                 235                 240

Phe Lys Ile His Gln Glu Ala Gln Pro Glu Lys Gly Ser Glu Asn Ala
                245                 250                 255

Val Ile Arg Val Pro Ala Ala Leu Pro Asp Glu Val Arg Glu Arg Ile
            260                 265                 270

Gln Lys Thr Ala Met Lys Ile Tyr Arg Ile Leu Gly Cys Arg Gly Leu
        275                 280                 285

Ala Arg Ile Asp Leu Phe Leu Arg Glu Asp Gly Cys Ile Val Leu Asn
    290                 295                 300

Glu Val Asn Thr Met Pro Gly Phe Thr Ser Tyr Ser Arg Tyr Pro Arg
305                 310                 315                 320

Met Met Thr Ala Ala Gly Phe Thr Leu Thr Glu Ile Leu Asp Arg Leu
                325                 330                 335

Ile Glu Leu Ser Leu Arg Arg
            340


<210> SEQ ID NO 73
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 73

Met Phe Lys Ile Lys Val Ala Val Leu Phe Gly Gly Cys Ser Glu Glu
  1             5                   10                  15

His Asn Val Ser Ile Lys Ser Ala Met Glu Ile Ala Ala Asn Ile Asp
            20                  25                  30

Thr Lys Lys Tyr Gln Pro Tyr Tyr Ile Gly Ile Thr Lys Ser Gly Val
```

35 40 45

Trp Lys Met Cys Glu Lys Pro Cys Leu Gly Trp Glu Gln Tyr Ala Gly
50 55 60

Asp Pro Val Val Phe Ser Pro Asp Arg Ser Thr His Gly Leu Leu Ile
65 70 75 80

Gln Lys Asp Thr Gly Tyr Glu Ile Gln Pro Val Asp Val Val Phe Pro
85 90 95

Met Ile His Gly Lys Phe Gly Glu Asp Gly Ser Ile Gln Gly Leu Leu
100 105 110

Glu Leu Ser Gly Ile Pro Tyr Val Gly Cys Asp Ile Gln Ser Ser Val
115 120 125

Ile Cys Met Asp Lys Ala Leu Ala Tyr Thr Val Val Lys Asn Ala Gly
130 135 140

Ile Ala Val Pro Gly Phe Arg Ile Leu Gln Glu Gly Asp Arg Leu Glu
145 150 155 160

Thr Glu Asp Leu Val Tyr Pro Val Phe Val Lys Pro Ala Arg Ser Gly
165 170 175

Ser Ser Phe Gly Val Asn Lys Val Cys Lys Ala Glu Glu Leu Gln Ala
180 185 190

Ala Ile Arg Glu Ala Arg Lys Tyr Asp Ser Lys Ile Leu Ile Glu Glu
195 200 205

Ala Val Thr Gly Ser Glu Val Gly Cys Ala Ile Leu Gly Asn Glu Asn
210 215 220

Asp Leu Met Ala Gly Glu Val Asp Gln Ile Glu Leu Arg His Gly Phe
225 230 235 240

Phe Lys Ile His Gln Glu Ala Gln Pro Glu Lys Gly Ser Glu Asn Ala
245 250 255

Val Ile Arg Val Pro Ala Ala Leu Pro Asp Glu Val Arg Glu Arg Ile
260 265 270

Arg Lys Thr Ala Met Lys Ile Tyr Arg Ile Leu Gly Cys Arg Gly Leu
275 280 285

Ala Arg Ile Asp Leu Phe Leu Arg Glu Asp Gly Cys Ile Val Leu Asn
290 295 300

Glu Val Asn Thr Met Pro Gly Phe Thr Ser Tyr Ser Arg Tyr Pro Arg
305 310 315 320

Met Met Thr Ala Ala Gly Phe Thr Leu Ser Glu Ile Leu Asp Arg Leu
325 330 335

Ile Glu Phe Ser Leu Arg Arg
340

<210> SEQ ID NO 74
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 74

Met Phe Arg Ile Lys Val Ala Val Leu Phe Gly Gly Cys Ser Glu Glu
1 5 10 15

His Asn Val Ser Ile Lys Ser Ala Met Glu Ile Ala Ala Asn Ile Asp
20 25 30

Thr Lys Lys Tyr Gln Pro Tyr Tyr Ile Gly Ile Thr Lys Ser Gly Val
35 40 45

Trp Lys Met Cys Glu Lys Pro Cys Leu Glu Trp Glu Gln Tyr Ala Gly

```
     50                  55                  60

Asp Pro Val Val Phe Ser Pro Asp Arg Ser Thr His Gly Leu Leu Ile
 65                  70                  75                  80

Gln Lys Asp Lys Gly Tyr Glu Ile Gln Pro Val Asp Val Val Phe Pro
                 85                  90                  95

Met Ile His Gly Lys Phe Gly Glu Asp Gly Ser Ile Gln Gly Leu Leu
            100                 105                 110

Glu Leu Ser Gly Ile Pro Tyr Val Gly Cys Asp Ile Gln Ser Ser Val
        115                 120                 125

Ile Cys Met Asp Lys Ala Leu Ala Tyr Thr Val Val Lys Asn Ala Gly
    130                 135                 140

Ile Thr Val Pro Gly Phe Arg Ile Leu Gln Glu Gly Asp Arg Leu Glu
145                 150                 155                 160

Thr Glu Asp Phe Val Tyr Pro Val Phe Val Lys Pro Ala Arg Ser Gly
                165                 170                 175

Ser Ser Phe Gly Val Asn Lys Val Cys Lys Ala Glu Glu Leu Gln Ala
            180                 185                 190

Ala Ile Glu Glu Ala Arg Lys Tyr Asp Ser Lys Ile Leu Ile Glu Glu
        195                 200                 205

Ala Val Thr Gly Ser Glu Val Gly Cys Ala Ile Leu Gly Asn Gly Asn
    210                 215                 220

Asp Leu Met Ala Gly Glu Val Asp Gln Ile Glu Leu Arg His Gly Phe
225                 230                 235                 240

Phe Lys Ile His Gln Glu Ala Gln Pro Glu Lys Gly Ser Glu Asn Ala
                245                 250                 255

Val Ile Arg Val Pro Ala Ala Leu Pro Asp Glu Val Arg Glu Gln Ile
            260                 265                 270

Gln Glu Thr Ala Met Lys Ile Tyr Arg Ile Leu Gly Cys Arg Gly Leu
        275                 280                 285

Ala Arg Ile Asp Leu Phe Leu Arg Glu Asp Gly Cys Ile Val Leu Asn
    290                 295                 300

Glu Val Asn Thr Met Pro Gly Phe Thr Ser Tyr Ser Arg Tyr Pro Arg
305                 310                 315                 320

Met Met Thr Ala Ala Gly Phe Thr Leu Ser Glu Ile Leu Asp Arg Leu
                325                 330                 335

Ile Glu Leu Ser Leu Arg Arg
            340


<210> SEQ ID NO 75
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 75

Met Phe Arg Ile Lys Val Ala Val Leu Phe Gly Gly Cys Ser Glu Glu
  1               5                  10                  15

His Asn Val Ser Ile Lys Ser Ala Met Glu Ile Ala Ala Asn Ile Asp
             20                  25                  30

Thr Lys Lys Tyr Gln Pro Tyr Tyr Ile Gly Ile Thr Lys Ser Gly Val
         35                  40                  45

Trp Lys Met Cys Glu Lys Pro Cys Leu Glu Trp Glu Gln Tyr Ala Gly
     50                  55                  60

Asp Pro Val Val Phe Ser Pro Asp Arg Ser Thr His Gly Leu Leu Ile
```

-continued

```
 65                  70                  75                  80

Gln Lys Asp Thr Gly Tyr Glu Ile Gln Pro Val Asp Val Gly Leu Pro
                85                  90                  95

Met Ile His Gly Lys Phe Gly Glu Asp Gly Ser Ile Gln Gly Leu Leu
            100                 105                 110

Glu Leu Ser Gly Ile Pro Tyr Val Gly Cys Asp Ile Gln Ser Ser Val
        115                 120                 125

Thr Cys Met Asp Lys Ala Leu Ala Tyr Thr Val Val Lys Asn Ala Gly
    130                 135                 140

Ile Ala Val Pro Gly Phe Arg Ile Leu Gln Glu Gly Asp Arg Leu Glu
145                 150                 155                 160

Thr Glu Asp Phe Val Tyr Pro Val Phe Val Lys Pro Ala Arg Ser Gly
                165                 170                 175

Ser Ser Phe Gly Val Asn Lys Val Cys Lys Ala Glu Glu Leu Gln Ala
            180                 185                 190

Ala Ile Glu Asp Ala Arg Lys Tyr Asp Ser Lys Ile Leu Ile Glu Glu
        195                 200                 205

Ala Val Thr Gly Ser Glu Val Gly Cys Ala Ile Leu Gly Asn Gly Asn
    210                 215                 220

Asp Leu Met Ala Gly Glu Val Asp Gln Ile Glu Leu Arg His Gly Phe
225                 230                 235                 240

Phe Lys Ile His Gln Glu Ala Gln Pro Glu Lys Gly Ser Glu Asn Ala
                245                 250                 255

Val Ile Arg Val Pro Ala Ala Leu Pro Asp Glu Val Ile Glu Arg Ile
            260                 265                 270

Gln Lys Thr Ala Met Lys Ile Tyr Arg Ile Leu Gly Cys Arg Gly Leu
        275                 280                 285

Ala Arg Ile Asp Leu Phe Leu Arg Glu Asp Gly Cys Ile Val Leu Asn
    290                 295                 300

Glu Val Asn Thr Met Pro Gly Phe Thr Ser Tyr Ser Arg Tyr Pro Arg
305                 310                 315                 320

Met Met Thr Ala Ala Gly Phe Thr Leu Thr Glu Ile Leu Asp Arg Leu
                325                 330                 335

Ile Glu Leu Ser Leu Arg Arg
            340


<210> SEQ ID NO 76
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 76

Met Tyr Lys Leu Lys Ile Ala Val Leu Phe Gly Gly Cys Ser Glu Glu
  1               5                  10                  15

His Asp Val Ser Val Lys Ser Ala Met Glu Val Ala Ala Asn Ile Asn
             20                  25                  30

Lys Glu Lys Tyr Gln Pro Phe Tyr Ile Gly Ile Thr Lys Ser Gly Ala
        35                  40                  45

Trp Lys Leu Cys Asp Lys Pro Cys Arg Asp Trp Glu Asn Tyr Ala Gly
     50                  55                  60

Tyr Pro Ala Val Ile Ser Pro Asp Arg Arg Ile His Gly Leu Leu Ile
 65                  70                  75                  80

Gln Lys Asp Gly Gly Tyr Glu Ser Gln Pro Val Asp Val Val Leu Pro
```

-continued

```
                85                  90                  95

Met Ile His Gly Lys Phe Gly Glu Asp Gly Thr Ile Gln Gly Leu Leu
            100                 105                 110

Glu Leu Ser Gly Ile Pro Tyr Val Gly Cys Asp Ile Gln Ser Ser Val
        115                 120                 125

Ile Cys Met Asp Lys Ser Leu Ala Tyr Met Val Val Lys Asn Ala Gly
    130                 135                 140

Ile Glu Val Pro Gly Phe Arg Val Leu Gln Lys Gly Asp Ser Leu Glu
145                 150                 155                 160

Ala Glu Thr Leu Ser Tyr Pro Val Phe Val Lys Pro Ala Arg Ser Gly
                165                 170                 175

Ser Ser Phe Gly Val Asn Lys Val Cys Arg Ala Glu Glu Leu Gln Ala
            180                 185                 190

Ala Val Thr Glu Ala Gly Lys Tyr Asp Ser Lys Ile Leu Val Glu Glu
        195                 200                 205

Ala Val Ser Gly Ser Glu Val Gly Cys Ala Ile Leu Gly Asn Gly Asn
    210                 215                 220

Asp Leu Ile Thr Gly Glu Val Asp Gln Ile Glu Leu Lys His Gly Phe
225                 230                 235                 240

Phe Lys Ile His Gln Glu Ala Gln Pro Glu Lys Gly Ser Glu Asn Ala
                245                 250                 255

Val Ile Arg Val Pro Ala Ala Leu Pro Asp Glu Val Arg Glu Gln Ile
            260                 265                 270

Gln Glu Thr Ala Lys Lys Ile Tyr Arg Val Leu Gly Cys Arg Gly Leu
        275                 280                 285

Ala Arg Ile Asp Leu Phe Leu Arg Glu Asp Gly Ser Ile Val Leu Asn
    290                 295                 300

Glu Val Asn Thr Met Pro Gly Phe Thr Ser Tyr Ser Arg Tyr Pro Arg
305                 310                 315                 320

Met Met Thr Ala Ala Gly Phe Thr Leu Ser Glu Ile Leu Asp Arg Leu
                325                 330                 335

Ile Gly Leu Ser Leu Arg Arg
            340


<210> SEQ ID NO 77
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 77

Met Tyr Lys Leu Lys Ile Ala Val Leu Phe Gly Gly Cys Ser Glu Glu
  1               5                  10                  15

His Asp Val Ser Val Lys Ser Ala Met Glu Val Ala Ala Asn Ile Asn
             20                  25                  30

Lys Glu Lys Tyr Gln Pro Phe Tyr Ile Gly Ile Thr Lys Ser Gly Ala
         35                  40                  45

Trp Lys Leu Cys Asp Lys Pro Cys Arg Asp Trp Glu Asn Tyr Ala Gly
     50                  55                  60

Tyr Pro Ala Val Ile Ser Pro Asp Arg Arg Ile His Gly Leu Leu Ile
 65                  70                  75                  80

Gln Lys Asp Gly Gly Tyr Glu Ser Gln Pro Val Asp Val Val Leu Pro
                 85                  90                  95

Met Ile His Gly Lys Phe Gly Glu Asp Gly Thr Ile Gln Gly Leu Leu
```

```
            100                 105                 110

Glu Leu Ser Gly Ile Pro Tyr Val Val Cys Asp Ile Gln Ser Ser Val
        115                 120                 125

Ile Cys Met Asp Lys Ser Leu Ala Tyr Met Val Val Lys Asn Ala Gly
    130                 135                 140

Ile Glu Val Pro Gly Phe Arg Val Leu Gln Lys Gly Asp Ser Leu Glu
145                 150                 155                 160

Ala Glu Thr Leu Ser Tyr Pro Val Phe Val Lys Pro Ala Arg Ser Gly
                165                 170                 175

Ser Ser Phe Gly Val Asn Lys Val Cys Arg Ala Glu Glu Leu Gln Ala
            180                 185                 190

Ala Val Thr Glu Ala Gly Lys Tyr Asp Ser Lys Ile Leu Val Glu Glu
        195                 200                 205

Ala Val Ser Gly Ser Glu Val Gly Cys Ala Ile Leu Gly Asn Gly Asn
    210                 215                 220

Asp Leu Ile Thr Gly Glu Val Asp Gln Ile Glu Leu Lys His Gly Phe
225                 230                 235                 240

Phe Lys Ile His Gln Glu Ala Gln Pro Glu Lys Gly Ser Glu Asn Ala
                245                 250                 255

Val Ile Arg Val Pro Ala Ala Leu Pro Asp Glu Val Arg Glu Gln Ile
            260                 265                 270

Gln Glu Thr Ala Lys Lys Ile Tyr Arg Val Leu Gly Cys Arg Gly Leu
        275                 280                 285

Ala Arg Ile Asp Leu Phe Leu Arg Glu Asp Gly Ser Ile Val Leu Asn
    290                 295                 300

Glu Val Asn Thr Met Pro Gly Phe Thr Ser Tyr Ser Arg Tyr Pro Arg
305                 310                 315                 320

Met Met Thr Ala Ala Gly Phe Thr Leu Ser Glu Ile Leu Asp Arg Leu
                325                 330                 335

Ile Gly Leu Ser Leu Arg Arg
            340


<210> SEQ ID NO 78
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 78

Met Tyr Lys Leu Lys Ile Ala Val Leu Phe Gly Gly Cys Ser Glu Glu
  1               5                  10                  15

His Asp Val Ser Val Lys Ser Ala Met Glu Val Ala Ala Asn Ile Asn
             20                  25                  30

Lys Glu Lys Tyr Gln Pro Phe Tyr Ile Gly Ile Thr Lys Ser Gly Ala
         35                  40                  45

Trp Lys Leu Cys Asp Lys Pro Cys Arg Asp Trp Glu Asn Tyr Ala Gly
     50                  55                  60

Tyr Pro Ala Val Ile Ser Pro Asp Arg Arg Thr His Gly Leu Leu Ile
 65                  70                  75                  80

Gln Lys Asp Gly Gly Tyr Glu Ser Gln Pro Val Asp Val Val Leu Pro
                 85                  90                  95

Met Ile His Gly Lys Phe Gly Glu Asp Gly Thr Ile Gln Gly Leu Leu
            100                 105                 110

Glu Leu Ser Gly Ile Pro Tyr Val Gly Cys Asp Ile Gln Ser Ser Val
```

```
        115                 120                 125

Thr Cys Met Asp Lys Ser Leu Ala Tyr Met Val Val Lys Asn Ala Gly
    130                 135                 140

Ile Glu Val Pro Gly Phe Arg Val Leu Gln Lys Gly Asp Ser Leu Lys
145                 150                 155                 160

Ala Glu Thr Leu Ser Tyr Pro Val Phe Val Lys Pro Ala Arg Ser Gly
                165                 170                 175

Ser Ser Phe Gly Val Asn Lys Val Cys Arg Ala Glu Glu Leu Gln Ala
            180                 185                 190

Ala Val Thr Glu Ala Gly Lys Tyr Asp Cys Lys Ile Leu Val Glu Glu
        195                 200                 205

Ala Val Ser Gly Ser Glu Val Gly Cys Ala Ile Leu Gly Asn Glu Asn
    210                 215                 220

Ala Leu Met Ala Gly Glu Val Asp Gln Ile Glu Leu Arg His Gly Phe
225                 230                 235                 240

Phe Lys Ile His Gln Glu Ala Gln Pro Glu Lys Gly Ser Glu Asn Ala
                245                 250                 255

Val Ile Arg Val Pro Ala Val Leu Pro Asp Glu Val Arg Glu Arg Ile
            260                 265                 270

Gln Lys Thr Ala Met Lys Ile Tyr Arg Ile Leu Gly Cys Arg Gly Leu
        275                 280                 285

Ala Arg Ile Asp Leu Phe Leu Arg Glu Asp Gly Cys Ile Val Leu Asn
    290                 295                 300

Glu Val Asn Thr Met Pro Gly Phe Thr Ser Tyr Ser Arg Tyr Pro Arg
305                 310                 315                 320

Met Met Thr Ala Ala Gly Phe Thr Leu Thr Glu Ile Leu Asp Arg Leu
                325                 330                 335

Ile Glu Leu Ser Leu Arg Arg
            340
```

```
<210> SEQ ID NO 79
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 79

Met Tyr Arg Ile Asn Val Ala Val Leu Phe Gly Gly Cys Ser Glu Glu
  1               5                  10                  15

His Thr Val Ser Ile Lys Ser Ala Met Glu Leu Ala Ala Asn Ile Asp
             20                  25                  30

Thr Glu Lys Tyr Gln Pro Phe Tyr Ile Gly Ile Thr Lys Ser Gly Val
         35                  40                  45

Trp Lys Leu Cys Glu Lys Pro Cys Leu Asp Trp Glu Gln Tyr Ala Lys
     50                  55                  60

Tyr Pro Val Val Phe Ser Pro Gly Arg Asn Thr His Gly Phe Leu Ile
 65                  70                  75                  80

Gln Lys Glu Asp Arg Tyr Glu Ile Gln Pro Val Asp Val Val Phe Pro
                 85                  90                  95

Ile Ile His Gly Lys Phe Gly Glu Asp Gly Ser Ile Gln Gly Leu Leu
            100                 105                 110

Glu Leu Ser Gly Ile Pro Tyr Val Gly Cys Asp Ile Gln Ser Ser Val
        115                 120                 125

Ile Cys Met Asp Lys Ser Leu Ala Tyr Thr Thr Val Lys Asn Ala Gly
```

```
    130                 135                 140

Ile Glu Val Pro Asp Phe Gln Ile Ile Gln Asp Gly Asp Ser Pro Lys
145                 150                 155                 160

Thr Glu Cys Phe Ser Phe Pro Leu Phe Val Lys Pro Ala Arg Ser Gly
                165                 170                 175

Ser Ser Phe Gly Val Asn Lys Val Asp Lys Ala Glu Asp Leu Cys Ala
            180                 185                 190

Ala Ile Asn Glu Ala Arg Gln Tyr Asp Arg Lys Val Leu Ile Glu Gln
        195                 200                 205

Ala Val Ser Gly Ser Glu Val Gly Cys Ala Val Leu Gly Thr Gly Thr
    210                 215                 220

Asp Leu Ile Val Gly Glu Val Asp Gln Ile Ser Leu Lys His Gly Phe
225                 230                 235                 240

Phe Lys Ile His Gln Glu Ala Gln Pro Glu Lys Gly Ser Glu Asn Ala
                245                 250                 255

Thr Ile Glu Val Pro Ala Asp Leu Pro Ala Lys Val Arg Glu Arg Ile
            260                 265                 270

Gln Lys Thr Ala Lys Lys Ile Tyr Gln Val Leu Gly Cys Arg Gly Leu
        275                 280                 285

Ala Arg Ile Asp Leu Phe Leu Arg Glu Asp Gly His Ile Val Leu Asn
    290                 295                 300

Glu Val Asn Thr Met Pro Gly Phe Thr Ser Tyr Ser Arg Tyr Pro Cys
305                 310                 315                 320

Met Met Thr Ala Ala Gly Phe Thr Leu Ser Glu Leu Ile Asp Arg Leu
                325                 330                 335

Ile Glu Leu Ala Leu Arg Arg
            340


<210> SEQ ID NO 80
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 80

Gly Ser Glu Asn Ala Val Ile Arg
  1               5


<210> SEQ ID NO 81
<211> LENGTH: 6
<212> TYPE: PRT
<213> ORGANISM: Unknown
<220> FEATURE:
<223> OTHER INFORMATION: peptide from a microbial resistance gene

<400> SEQUENCE: 81

Ile Asp Leu Phe Leu Arg
  1               5


<210> SEQ ID NO 82
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 82

Ile His Gln Glu Ala Gln Pro Glu Lys
  1               5
```

<210> SEQ ID NO 83
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 83

```
Ser Gly Ser Ser Phe Gly Val Asn Lys
  1               5
```

<210> SEQ ID NO 84
<211> LENGTH: 352
<212> TYPE: PRT
<213> ORGANISM: Unknown
<220> FEATURE:
<223> OTHER INFORMATION: peptide from a microbial resistance gene

<400> SEQUENCE: 84

```
Met Lys Thr Val Ala Ile Ile Phe Gly Gly Val Ser Ser Glu Tyr Glu
  1               5                  10                  15

Val Ser Leu Lys Ser Ala Val Ala Ile Ile Lys Asn Met Glu Ser Ile
             20                  25                  30

Asp Tyr Asn Val Met Lys Ile Gly Ile Thr Glu Glu Gly His Trp Tyr
         35                  40                  45

Leu Phe Glu Gly Thr Thr Asp Lys Ile Lys Lys Asp Arg Trp Phe Leu
     50                  55                  60

Asp Glu Ser Cys Glu Glu Ile Val Val Asp Phe Ala Lys Lys Ser Phe
 65                  70                  75                  80

Val Leu Lys Asn Ser Lys Lys Ile Ile Lys Pro Asp Ile Leu Phe Pro
                 85                  90                  95

Val Leu His Gly Gly Tyr Gly Glu Asn Gly Ala Met Gln Gly Val Phe
            100                 105                 110

Glu Leu Leu Asp Ile Pro Tyr Val Gly Cys Gly Ile Gly Ala Ala Ala
        115                 120                 125

Ile Ser Met Asn Lys Ile Met Leu His Gln Phe Ala Glu Ala Ile Gly
    130                 135                 140

Val Lys Ser Thr Pro Ser Met Ile Ile Glu Lys Gly Gln Asp Leu Gln
145                 150                 155                 160

Lys Val Asp Ala Phe Ala Lys Ile His Gly Phe Pro Leu Tyr Ile Lys
                165                 170                 175

Pro Asn Glu Ala Gly Ser Ser Lys Gly Ile Ser Lys Val Glu Arg Lys
            180                 185                 190

Ser Asp Leu Tyr Lys Ala Ile Asp Glu Ala Ser Lys Tyr Asp Ser Arg
        195                 200                 205

Ile Leu Ile Gln Lys Glu Val Lys Gly Val Glu Ile Gly Cys Gly Ile
    210                 215                 220

Leu Gly Asn Glu Gln Leu Val Val Gly Glu Cys Asp Gln Ile Ser Leu
225                 230                 235                 240

Val Asp Gly Phe Phe Asp Tyr Glu Glu Lys Tyr Asn Leu Val Thr Ala
                245                 250                 255

Glu Ile Leu Leu Pro Ala Lys Leu Ser Ile Asp Lys Lys Glu Asp Ile
            260                 265                 270

Gln Met Lys Ala Lys Lys Leu Tyr Arg Leu Leu Gly Cys Lys Gly Leu
        275                 280                 285

Ala Arg Ile Asp Phe Phe Leu Thr Asp Asp Gly Glu Ile Leu Leu Asn
```

```
    290                 295                 300

Glu Ile Asn Thr Met Pro Gly Phe Thr Glu His Ser Arg Phe Pro Met
305                 310                 315                 320

Met Met Asn Glu Ile Gly Met Asp Tyr Lys Glu Ile Ile Glu Asn Leu
                325                 330                 335

Leu Val Leu Ala Val Glu Asn His Glu Lys Lys Leu Ser Thr Ile Asp
            340                 345                 350
```

<210> SEQ ID NO 85
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 85

```
Ala Ile Asp Glu Ala Ser Lys
  1               5
```

<210> SEQ ID NO 86
<211> LENGTH: 13
<212> TYPE: PRT
<213> ORGANISM: Unknown
<220> FEATURE:
<223> OTHER INFORMATION: peptide from a microbial resistance gene

<400> SEQUENCE: 86

```
Phe Pro Met Met Met Asn Glu Ile Gly Met Asp Tyr Lys
  1               5                   10
```

<210> SEQ ID NO 87
<211> LENGTH: 13
<212> TYPE: PRT
<213> ORGANISM: Unknown
<220> FEATURE:
<223> OTHER INFORMATION: peptide from a microbial resistance gene

<400> SEQUENCE: 87

```
Ile Met Leu His Gln Phe Ala Glu Ala Ile Gly Val Lys
  1               5                   10
```

<210> SEQ ID NO 88
<211> LENGTH: 11
<212> TYPE: PRT
<213> ORGANISM: Unknown
<220> FEATURE:
<223> OTHER INFORMATION: peptide from a microbial resistance gene

<400> SEQUENCE: 88

```
Asn Met Glu Ser Ile Asp Tyr Asn Val Met Lys
  1               5                   10
```

<210> SEQ ID NO 89
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 89

```
Ser Ala Val Ala Ile Ile Lys
  1               5
```

<210> SEQ ID NO 90
<211> LENGTH: 9

<212> TYPE: PRT
<213> ORGANISM: Unknown
<220> FEATURE:
<223> OTHER INFORMATION: peptide from a microbial resistance gene

<400> SEQUENCE: 90

```
Ser Thr Pro Ser Met Ile Ile Glu Lys
  1               5
```

<210> SEQ ID NO 91
<211> LENGTH: 13
<212> TYPE: PRT
<213> ORGANISM: Unknown
<220> FEATURE:
<223> OTHER INFORMATION: peptide from a microbial resistance gene

<400> SEQUENCE: 91

```
Tyr Asn Leu Val Thr Ala Glu Ile Leu Leu Pro Ala Lys
  1               5                  10
```

<210> SEQ ID NO 92
<211> LENGTH: 349
<212> TYPE: PRT
<213> ORGANISM: Unknown
<220> FEATURE:
<223> OTHER INFORMATION: peptide from a microbial resistance gene

<400> SEQUENCE: 92

```
Met Ile Lys Lys Arg Ile Ala Ile Ile Phe Gly Gly Asn Ser Thr Glu
  1               5                  10                  15

Tyr Glu Val Ser Leu Gln Ser Ala Ser Ala Val Phe Glu Asn Ile Asn
             20                  25                  30

Thr Lys Lys Phe Asp Ile Val Pro Ile Gly Ile Thr Arg Asn Gly Asp
         35                  40                  45

Trp Tyr His Tyr Thr Gly Lys Lys Glu Lys Ile Ala Asn Asn Thr Trp
     50                  55                  60

Phe Glu Asp Asn Glu Asn Leu Tyr Ser Val Ala Val Ser Gln Asn Arg
 65                  70                  75                  80

Ser Val Lys Gly Phe Ile Glu Phe Lys Glu Glu Lys Phe Tyr Ile Ile
                 85                  90                  95

Lys Val Asp Leu Ile Phe Pro Val Leu His Gly Lys Asn Gly Glu Asp
            100                 105                 110

Gly Thr Leu Gln Gly Leu Phe Glu Leu Ala Gly Ile Pro Val Val Gly
        115                 120                 125

Cys Asp Thr Leu Ser Ser Ala Leu Cys Met Asp Lys Asp Lys Ala His
    130                 135                 140

Lys Leu Val Ser Leu Ala Gly Ile Ser Val Pro Lys Ser Val Thr Phe
145                 150                 155                 160

Lys Phe Ser Gly Lys Lys Ala Ala Leu Lys Lys Ile Glu Lys Glu Leu
                165                 170                 175

Ser Tyr Pro Leu Phe Val Lys Pro Val Arg Ala Gly Ser Ser Phe Gly
            180                 185                 190

Ile Thr Lys Val Thr Lys Gln Gln Glu Leu Glu Asn Ala Ile Gln Leu
        195                 200                 205

Ala Phe Glu His Asp Ala Glu Val Ile Val Glu Glu Thr Ile Asn Gly
    210                 215                 220

Phe Glu Val Gly Cys Ala Val Leu Gly Ile Asp Glu Leu Ile Val Gly
225                 230                 235                 240

Arg Val Asp Glu Ile Glu Leu Ser Ser Gly Phe Phe Asp Tyr Thr Glu
```

```
                245                 250                 255

Lys Tyr Thr Leu Lys Ser Ser Lys Ile Tyr Met Pro Ala Arg Ile Asp
            260                 265                 270

Ala Glu Ala Glu Lys Arg Ile Gln Glu Thr Ala Val Thr Ile Tyr Lys
        275                 280                 285

Ala Leu Gly Cys Ser Gly Phe Ser Arg Val Asp Met Phe Tyr Thr Pro
    290                 295                 300

Ser Gly Glu Ile Val Phe Asn Glu Val Asn Thr Ile Pro Gly Phe Thr
305                 310                 315                 320

Ser His Ser Arg Tyr Pro Asn Met Met Lys Gly Ile Gly Leu Ser Phe
                325                 330                 335

Ala Gln Met Leu Asp Lys Leu Ile Gly Leu Tyr Val Glu
            340                 345


<210> SEQ ID NO 93
<211> LENGTH: 349
<212> TYPE: PRT
<213> ORGANISM: Unknown
<220> FEATURE:
<223> OTHER INFORMATION: peptide from a microbial resistance gene

<400> SEQUENCE: 93

Met Gln Asn Lys Lys Ile Ala Val Ile Phe Gly Gly Asn Ser Thr Glu
  1               5                  10                  15

Tyr Glu Val Ser Leu Gln Ser Ala Ser Ala Val Phe Glu Asn Ile Asn
             20                  25                  30

Thr Asn Lys Phe Asp Ile Ile Pro Ile Gly Ile Thr Arg Ser Gly Glu
         35                  40                  45

Trp Tyr His Tyr Thr Gly Glu Lys Glu Lys Ile Leu Asn Asn Thr Trp
     50                  55                  60

Phe Glu Asp Ser Lys Asn Leu Cys Pro Val Val Val Ser Gln Asn Arg
 65                  70                  75                  80

Ser Val Lys Gly Phe Leu Glu Ile Ala Ser Asp Lys Tyr Arg Ile Ile
                 85                  90                  95

Lys Val Asp Leu Val Phe Pro Val Leu His Gly Lys Asn Gly Glu Asp
            100                 105                 110

Gly Thr Leu Gln Gly Ile Phe Glu Leu Ala Gly Ile Pro Val Val Gly
        115                 120                 125

Cys Asp Thr Leu Ser Ser Ala Leu Cys Met Asp Lys Asp Arg Ala His
    130                 135                 140

Lys Leu Val Ser Leu Ala Gly Ile Ser Val Pro Lys Ser Val Thr Phe
145                 150                 155                 160

Lys Arg Phe Asn Glu Glu Ala Ala Met Lys Glu Ile Glu Ala Asn Leu
                165                 170                 175

Thr Tyr Pro Leu Phe Ile Lys Pro Val Arg Ala Gly Ser Ser Phe Gly
            180                 185                 190

Ile Thr Lys Val Ile Glu Lys Gln Glu Leu Asp Ala Ala Ile Glu Leu
        195                 200                 205

Ala Phe Glu His Asp Thr Glu Val Ile Val Glu Glu Thr Ile Asn Gly
    210                 215                 220

Phe Glu Val Gly Cys Ala Val Leu Gly Ile Asp Glu Leu Ile Val Gly
225                 230                 235                 240

Arg Val Asp Glu Ile Glu Leu Ser Ser Gly Phe Phe Asp Tyr Thr Glu
                245                 250                 255

Lys Tyr Thr Leu Lys Ser Ser Lys Ile Tyr Met Pro Ala Arg Ile Asp
```

-continued

```
            260                 265                 270

Ala Glu Ala Glu Lys Arg Ile Gln Glu Ala Ala Val Thr Ile Tyr Lys
        275                 280                 285

Ala Leu Gly Cys Ser Gly Phe Ser Arg Val Asp Met Phe Tyr Thr Pro
    290                 295                 300

Ser Gly Glu Ile Val Phe Asn Glu Val Asn Thr Ile Pro Gly Phe Thr
305                 310                 315                 320

Ser His Ser Arg Tyr Pro Asn Met Met Lys Gly Ile Gly Leu Ser Phe
                325                 330                 335

Ser Gln Met Leu Asp Lys Leu Ile Gly Leu Tyr Val Glu
            340                 345


<210> SEQ ID NO 94
<211> LENGTH: 349
<212> TYPE: PRT
<213> ORGANISM: Unknown
<220> FEATURE:
<223> OTHER INFORMATION: peptide from a microbial resistance gene

<400> SEQUENCE: 94

Met Gln Asn Lys Lys Ile Ala Val Ile Phe Gly Gly Asn Ser Thr Glu
  1               5                  10                  15

Tyr Glu Val Ser Leu Gln Ser Ala Ser Ala Val Phe Glu Asn Ile Asn
             20                  25                  30

Thr Asn Lys Phe Asp Ile Ile Pro Ile Gly Ile Thr Arg Ser Gly Glu
         35                  40                  45

Trp Tyr His Tyr Thr Gly Glu Lys Glu Lys Ile Leu Asn Asn Thr Trp
     50                  55                  60

Phe Glu Asp Ser Lys Asn Leu Cys Pro Val Val Val Ser Gln Asn Arg
 65                  70                  75                  80

Ser Val Lys Gly Phe Leu Glu Ile Ala Ser Asp Lys Tyr Arg Ile Ile
                 85                  90                  95

Lys Val Asp Leu Val Phe Pro Val Leu His Gly Lys Asn Gly Glu Asn
            100                 105                 110

Gly Thr Leu Gln Gly Ile Phe Glu Leu Ala Gly Ile Pro Val Val Gly
        115                 120                 125

Cys Asp Thr Leu Ser Ser Ala Leu Cys Met Asp Lys Asp Arg Ala His
    130                 135                 140

Lys Leu Val Ser Leu Ala Gly Ile Ser Val Pro Lys Ser Val Thr Phe
145                 150                 155                 160

Lys Arg Phe Asn Glu Glu Ala Ala Met Lys Glu Ile Glu Ala Asn Leu
                165                 170                 175

Thr Tyr Pro Leu Phe Ile Lys Pro Val Arg Ala Gly Ser Ser Phe Gly
            180                 185                 190

Ile Thr Lys Val Ile Glu Lys Gln Glu Leu Asp Ala Ala Ile Glu Leu
        195                 200                 205

Ala Phe Glu His Asp Thr Glu Val Ile Val Glu Glu Thr Ile Asn Gly
    210                 215                 220

Phe Glu Val Gly Cys Ala Val Leu Gly Ile Asp Glu Leu Ile Val Gly
225                 230                 235                 240

Arg Val Asp Glu Ile Glu Leu Ser Ser Gly Phe Phe Asp Tyr Thr Glu
                245                 250                 255

Lys Tyr Thr Leu Lys Ser Ser Lys Ile Tyr Met Pro Ala Arg Ile Asp
            260                 265                 270

Ala Glu Ala Glu Lys Arg Ile Gln Glu Ala Ala Val Thr Ile Tyr Lys
```

```
        275                 280                 285

Ala Leu Gly Cys Ser Gly Phe Ser Arg Val Asp Met Phe Tyr Thr Pro
    290                 295                 300

Ser Gly Glu Ile Val Phe Asn Glu Val Asn Thr Ile Pro Gly Phe Thr
305                 310                 315                 320

Ser His Ser Arg Tyr Pro Asn Met Met Lys Gly Ile Gly Leu Ser Phe
                325                 330                 335

Ser Gln Met Leu Asp Lys Leu Ile Gly Leu Tyr Val Glu
            340                 345


<210> SEQ ID NO 95
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 95

Ala Gly Ser Ser Phe Gly Ile Thr Lys
  1               5


<210> SEQ ID NO 96
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 96

Ala Leu Gly Cys Ser Gly Phe Ser Arg
  1               5


<210> SEQ ID NO 97
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 97

Ile Asp Ala Glu Ala Glu Lys
  1               5


<210> SEQ ID NO 98
<211> LENGTH: 6
<212> TYPE: PRT
<213> ORGANISM: Unknown
<220> FEATURE:
<223> OTHER INFORMATION: peptide from a microbial resistance gene

<400> SEQUENCE: 98

Ile Tyr Met Pro Ala Arg
  1               5


<210> SEQ ID NO 99
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 99

Leu Ile Gly Leu Tyr Val Glu
  1               5
```

<210> SEQ ID NO 100
<211> LENGTH: 11
<212> TYPE: PRT
<213> ORGANISM: Unknown
<220> FEATURE:
<223> OTHER INFORMATION: peptide from a microbial resistance gene

<400> SEQUENCE: 100

Leu Val Ser Leu Ala Gly Ile Ser Val Pro Lys
1 5 10

<210> SEQ ID NO 101
<211> LENGTH: 16
<212> TYPE: PRT
<213> ORGANISM: Unknown
<220> FEATURE:
<223> OTHER INFORMATION: peptide from a microbial resistance gene

<400> SEQUENCE: 101

Val Asp Glu Ile Glu Leu Ser Ser Gly Phe Phe Asp Tyr Thr Glu Lys
1 5 10 15

<210> SEQ ID NO 102
<211> LENGTH: 6
<212> TYPE: PRT
<213> ORGANISM: Unknown
<220> FEATURE:
<223> OTHER INFORMATION: peptide from a microbial resistance gene

<400> SEQUENCE: 102

Tyr Pro Asn Met Met Lys
1 5

<210> SEQ ID NO 103
<211> LENGTH: 349
<212> TYPE: PRT
<213> ORGANISM: Unknown
<220> FEATURE:
<223> OTHER INFORMATION: peptide from a microbial resistance gene

<400> SEQUENCE: 103

Met Met Lys Leu Lys Lys Ile Ala Ile Ile Phe Gly Gly Gln Ser Ser
1 5 10 15

Glu Tyr Glu Val Ser Leu Lys Ser Thr Val Ser Val Leu Glu Thr Leu
20 25 30

Ser Thr Cys Asn Phe Glu Ile Ile Lys Ile Gly Ile Asp Leu Gly Gly
35 40 45

Lys Trp Tyr Leu Thr Thr Ser Asn Asn Lys Asp Ile Glu Tyr Asp Val
50 55 60

Trp Gln Thr Asp Pro Ser Leu Gln Glu Ile Ile Pro Cys Phe Asn Asn
65 70 75 80

Arg Gly Phe Tyr Asn Lys Thr Thr Asn Lys Tyr Phe Arg Pro Asp Val
85 90 95

Leu Phe Pro Ile Leu His Gly Gly Thr Gly Glu Asp Gly Thr Leu Gln
100 105 110

Gly Val Phe Glu Leu Met Asn Ile Pro Tyr Val Gly Cys Gly Val Thr
115 120 125

Pro Ser Ala Ile Cys Met Asp Lys Tyr Leu Leu His Glu Phe Ala Gln
130 135 140

Ser Val Gly Val Lys Ser Ala Pro Thr Leu Ile Ile Arg Thr Arg Asn
145 150 155 160

```
Cys Lys Asp Glu Ile Asp Lys Phe Ile Glu Lys Asn Asp Phe Pro Ile
                165                 170                 175

Phe Val Lys Pro Asn Glu Ala Gly Ser Ser Lys Gly Ile Asn Lys Val
            180                 185                 190

Asn Glu Pro Asp Lys Leu Glu Asp Ala Leu Thr Glu Ala Phe Lys Tyr
        195                 200                 205

Ser Lys Ser Val Ile Ile Gln Lys Ala Ile Ile Gly Arg Glu Ile Gly
    210                 215                 220

Cys Ala Val Leu Gly Asn Glu Lys Leu Leu Val Gly Glu Cys Asp Glu
225                 230                 235                 240

Val Ser Leu Asn Ser Asp Phe Phe Asp Tyr Thr Glu Lys Tyr Gln Met
                245                 250                 255

Ile Ser Ala Lys Val Asn Ile Pro Ala Ser Ile Ser Val Glu Phe Ser
            260                 265                 270

Asn Glu Met Lys Lys Gln Ala Gln Leu Leu Tyr Arg Leu Leu Gly Cys
        275                 280                 285

Ser Gly Leu Ala Arg Ile Asp Phe Phe Leu Ser Asp Asn Asn Glu Ile
    290                 295                 300

Leu Leu Asn Glu Ile Asn Thr Leu Pro Gly Phe Thr Glu His Ser Arg
305                 310                 315                 320

Tyr Pro Lys Met Met Glu Ala Val Gly Val Thr Tyr Lys Glu Ile Ile
                325                 330                 335

Thr Lys Leu Ile Asn Leu Ala Glu Glu Lys Tyr Tyr Gly
            340                 345
```

```
<210> SEQ ID NO 104
<211> LENGTH: 23
<212> TYPE: PRT
<213> ORGANISM: Unknown
<220> FEATURE:
<223> OTHER INFORMATION: peptide from a microbial resistance gene

<400> SEQUENCE: 104

Asp Ile Glu Tyr Asp Val Trp Gln Thr Asp Pro Ser Leu Gln Glu Ile
  1               5                  10                  15

Ile Pro Cys Phe Asn Asn Arg
             20
```

```
<210> SEQ ID NO 105
<211> LENGTH: 11
<212> TYPE: PRT
<213> ORGANISM: Unknown
<220> FEATURE:
<223> OTHER INFORMATION: peptide from a microbial resistance gene

<400> SEQUENCE: 105

Glu Ile Gly Cys Ala Val Leu Gly Asn Glu Lys
  1               5                  10
```

```
<210> SEQ ID NO 106
<211> LENGTH: 17
<212> TYPE: PRT
<213> ORGANISM: Unknown
<220> FEATURE:
<223> OTHER INFORMATION: peptide from a microbial resistance gene

<400> SEQUENCE: 106

Ile Ala Ile Ile Phe Gly Gly Gln Ser Ser Glu Tyr Glu Val Ser Leu
  1               5                  10                  15

Lys
```

```
<210> SEQ ID NO 107
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 107

Ile Gly Ile Asp Leu Gly Gly Lys
  1               5


<210> SEQ ID NO 108
<211> LENGTH: 10
<212> TYPE: PRT
<213> ORGANISM: Unknown
<220> FEATURE:
<223> OTHER INFORMATION: peptide from a microbial resistance gene

<400> SEQUENCE: 108

Leu Glu Asp Ala Leu Thr Glu Ala Phe Lys
  1               5                  10


<210> SEQ ID NO 109
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 109

Leu Ile Asn Leu Ala Glu Glu Lys
  1               5


<210> SEQ ID NO 110
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 110

Leu Leu Gly Cys Ser Gly Leu Ala Arg
  1               5


<210> SEQ ID NO 111
<211> LENGTH: 21
<212> TYPE: PRT
<213> ORGANISM: Unknown
<220> FEATURE:
<223> OTHER INFORMATION: peptide from a microbial resistance gene

<400> SEQUENCE: 111

Leu Leu Val Gly Glu Cys Asp Glu Val Ser Leu Asn Ser Asp Phe Phe
  1               5                  10                  15

Asp Tyr Thr Glu Lys
             20


<210> SEQ ID NO 112
<211> LENGTH: 10
<212> TYPE: PRT
<213> ORGANISM: Unknown
<220> FEATURE:
<223> OTHER INFORMATION: peptide from a microbial resistance gene

<400> SEQUENCE: 112
```

Met Met Glu Ala Val Gly Val Thr Tyr Lys
1 5 10

<210> SEQ ID NO 113
<211> LENGTH: 16
<212> TYPE: PRT
<213> ORGANISM: Unknown
<220> FEATURE:
<223> OTHER INFORMATION: peptide from a microbial resistance gene

<400> SEQUENCE: 113

Asn Asp Phe Pro Ile Phe Val Lys Pro Asn Glu Ala Gly Ser Ser Lys
1 5 10 15

<210> SEQ ID NO 114
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 114

Gln Ala Gln Leu Leu Tyr Arg
1 5

<210> SEQ ID NO 115
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 115

Ser Ala Pro Thr Leu Ile Ile Arg
1 5

<210> SEQ ID NO 116
<211> LENGTH: 18
<212> TYPE: PRT
<213> ORGANISM: Unknown
<220> FEATURE:
<223> OTHER INFORMATION: peptide from a microbial resistance gene

<400> SEQUENCE: 116

Ser Thr Val Ser Val Leu Glu Thr Leu Ser Thr Cys Asn Phe Glu Ile
1 5 10 15

Ile Lys

<210> SEQ ID NO 117
<211> LENGTH: 16
<212> TYPE: PRT
<213> ORGANISM: Unknown
<220> FEATURE:
<223> OTHER INFORMATION: peptide from a microbial resistance gene

<400> SEQUENCE: 117

Val Asn Ile Pro Ala Ser Ile Ser Val Glu Phe Ser Asn Glu Met Lys
1 5 10 15

<210> SEQ ID NO 118
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 118

```
Trp Tyr Leu Thr Thr Ser Asn Asn Lys
  1               5


<210> SEQ ID NO 119
<211> LENGTH: 13
<212> TYPE: PRT
<213> ORGANISM: Unknown
<220> FEATURE:
<223> OTHER INFORMATION: peptide from a microbial resistance gene

<400> SEQUENCE: 119

Tyr Leu Leu His Glu Phe Ala Gln Ser Val Gly Val Lys
  1               5                  10


<210> SEQ ID NO 120
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 120

Tyr Gln Met Ile Ser Ala Lys
  1               5


<210> SEQ ID NO 121
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 121

Met Asn Arg Leu Lys Ile Ala Ile Leu Phe Gly Gly Cys Ser Glu Glu
  1               5                  10                  15

His Asn Val Ser Val Lys Ser Ala Ala Glu Ile Ala Asn Asn Ile Asp
             20                  25                  30

Ile Gly Lys Tyr Glu Pro Ile Tyr Ile Gly Ile Thr Gln Ser Gly Val
         35                  40                  45

Trp Lys Thr Cys Glu Lys Pro Cys Ile Asp Trp Asp Asn Glu His Cys
     50                  55                  60

Arg Ser Ala Val Leu Ser Pro Asp Lys Lys Met His Gly Leu Leu Ile
 65                  70                  75                  80

Met Gln Asp Lys Gly Tyr Gln Ile Gln Arg Ile Asp Val Val Phe Ser
                 85                  90                  95

Val Leu His Gly Lys Ser Gly Glu Asp Gly Ala Ile Gln Gly Leu Phe
            100                 105                 110

Glu Leu Ser Gly Ile Pro Tyr Val Gly Cys Asp Ile Gln Ser Ser Ala
        115                 120                 125

Val Cys Met Asp Lys Ser Leu Ala Tyr Ile Ile Ala Lys Asn Ala Gly
    130                 135                 140

Ile Ala Thr Pro Glu Phe Gln Val Ile Tyr Lys Asp Asp Lys Pro Ala
145                 150                 155                 160

Ala Asp Ser Phe Thr Tyr Pro Val Phe Val Lys Pro Ala Arg Ser Gly
                165                 170                 175

Ser Ser Tyr Gly Val Asn Lys Val Asn Ser Ala Asp Glu Leu Asp Ser
            180                 185                 190

Ala Ile Asp Leu Ala Arg Gln Tyr Asp Ser Lys Ile Leu Ile Glu Gln
        195                 200                 205
```

-continued

```
Gly Val Leu Gly Tyr Glu Val Gly Cys Ala Val Leu Gly Asn Ser Phe
    210                 215                 220

Asp Leu Ile Val Gly Glu Val Asp Gln Ile Arg Leu Gln His Gly Ile
225                 230                 235                 240

Phe Arg Ile His Gln Glu Ala Glu Pro Glu Lys Gly Ser Glu Asn Ala
                245                 250                 255

Thr Ile Thr Val Pro Ala Glu Leu Ser Ala Glu Glu Arg Glu Arg Ile
            260                 265                 270

Lys Glu Ala Ala Lys Asn Ile Tyr Lys Ala Leu Gly Cys Arg Gly Leu
        275                 280                 285

Ser Arg Val Asp Met Phe Leu Gln Asp Asn Gly Arg Ile Val Leu Asn
    290                 295                 300

Glu Val Asn Thr Met Pro Gly Phe Thr Ser Tyr Ser Arg Tyr Pro Arg
305                 310                 315                 320

Met Met Val Ser Ala Gly Ile Thr Ile Pro Glu Leu Ile Asp His Leu
                325                 330                 335

Ile Val Leu Ala Val Lys Glu
            340


<210> SEQ ID NO 122
<211> LENGTH: 19
<212> TYPE: PRT
<213> ORGANISM: Unknown
<220> FEATURE:
<223> OTHER INFORMATION: peptide from a microbial resistance gene

<400> SEQUENCE: 122

Asp Asp Lys Pro Ala Ala Asp Ser Phe Thr Tyr Pro Val Phe Val Lys
  1               5                  10                  15

Pro Ala Arg


<210> SEQ ID NO 123
<211> LENGTH: 18
<212> TYPE: PRT
<213> ORGANISM: Unknown
<220> FEATURE:
<223> OTHER INFORMATION: peptide from a microbial resistance gene

<400> SEQUENCE: 123

Gly Ser Glu Asn Ala Thr Ile Thr Val Pro Ala Glu Leu Ser Ala Glu
  1               5                  10                  15

Glu Arg


<210> SEQ ID NO 124
<211> LENGTH: 17
<212> TYPE: PRT
<213> ORGANISM: Unknown
<220> FEATURE:
<223> OTHER INFORMATION: peptide from a microbial resistance gene

<400> SEQUENCE: 124

Ile Ala Ile Leu Phe Gly Gly Cys Ser Glu Glu His Asn Val Ser Val
  1               5                  10                  15

Lys


<210> SEQ ID NO 125
<211> LENGTH: 11
<212> TYPE: PRT
<213> ORGANISM: Unknown
<220> FEATURE:
<223> OTHER INFORMATION: peptide from a microbial resistance gene
```

<400> SEQUENCE: 125

Ile Asp Val Val Phe Ser Val Leu His Gly Lys
1 5 10

<210> SEQ ID NO 126
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 126

Ile His Gln Glu Ala Glu Pro Glu Lys
1 5

<210> SEQ ID NO 127
<211> LENGTH: 17
<212> TYPE: PRT
<213> ORGANISM: Unknown
<220> FEATURE:
<223> OTHER INFORMATION: peptide from a microbial resistance gene

<400> SEQUENCE: 127

Ile Val Leu Asn Glu Val Asn Thr Met Pro Gly Phe Thr Ser Tyr Ser
1 5 10 15

Arg

<210> SEQ ID NO 128
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 128

Leu Gln His Gly Ile Phe Arg
1 5

<210> SEQ ID NO 129
<211> LENGTH: 10
<212> TYPE: PRT
<213> ORGANISM: Unknown
<220> FEATURE:
<223> OTHER INFORMATION: peptide from a microbial resistance gene

<400> SEQUENCE: 129

Met His Gly Leu Leu Ile Met Gln Asp Lys
1 5 10

<210> SEQ ID NO 130
<211> LENGTH: 22
<212> TYPE: PRT
<213> ORGANISM: Unknown
<220> FEATURE:
<223> OTHER INFORMATION: peptide from a microbial resistance gene

<400> SEQUENCE: 130

Met Met Val Ser Ala Gly Ile Thr Ile Pro Glu Leu Ile Asp His Leu
1 5 10 15

Ile Val Leu Ala Val Lys
20

<210> SEQ ID NO 131
<211> LENGTH: 14

<212> TYPE: PRT
<213> ORGANISM: Unknown
<220> FEATURE:
<223> OTHER INFORMATION: peptide from a microbial resistance gene

<400> SEQUENCE: 131

Asn Ala Gly Ile Ala Thr Pro Glu Phe Gln Val Ile Tyr Lys
1 5 10

<210> SEQ ID NO 132
<211> LENGTH: 13
<212> TYPE: PRT
<213> ORGANISM: Unknown
<220> FEATURE:
<223> OTHER INFORMATION: peptide from a microbial resistance gene

<400> SEQUENCE: 132

Ser Ala Ala Glu Ile Ala Asn Asn Ile Asp Ile Gly Lys
1 5 10

<210> SEQ ID NO 133
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 133

Ser Ala Val Leu Ser Pro Asp Lys
1 5

<210> SEQ ID NO 134
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 134

Ser Gly Ser Ser Tyr Gly Val Asn Lys
1 5

<210> SEQ ID NO 135
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 135

Ser Leu Ala Tyr Ile Ile Ala Lys
1 5

<210> SEQ ID NO 136
<211> LENGTH: 15
<212> TYPE: PRT
<213> ORGANISM: Unknown
<220> FEATURE:
<223> OTHER INFORMATION: peptide from a microbial resistance gene

<400> SEQUENCE: 136

Thr Cys Glu Lys Pro Cys Ile Asp Trp Asp Asn Glu His Cys Arg
1 5 10 15

<210> SEQ ID NO 137
<211> LENGTH: 10
<212> TYPE: PRT

```
<213> ORGANISM: Unknown
<220> FEATURE:
<223> OTHER INFORMATION: peptide from a microbial resistance gene

<400> SEQUENCE: 137

Val Asp Met Phe Leu Gln Asp Asn Gly Arg
  1               5                  10


<210> SEQ ID NO 138
<211> LENGTH: 15
<212> TYPE: PRT
<213> ORGANISM: Unknown
<220> FEATURE:
<223> OTHER INFORMATION: peptide from a microbial resistance gene

<400> SEQUENCE: 138

Val Asn Ser Ala Asp Glu Leu Asp Ser Ala Ile Asp Leu Ala Arg
  1               5                  10                  15


<210> SEQ ID NO 139
<211> LENGTH: 15
<212> TYPE: PRT
<213> ORGANISM: Unknown
<220> FEATURE:
<223> OTHER INFORMATION: peptide from a microbial resistance gene

<400> SEQUENCE: 139

Tyr Glu Pro Ile Tyr Ile Gly Ile Thr Gln Ser Gly Val Trp Lys
  1               5                  10                  15


<210> SEQ ID NO 140
<211> LENGTH: 343
<212> TYPE: PRT
<213> ORGANISM: Unknown
<220> FEATURE:
<223> OTHER INFORMATION: peptide from a microbial resistance gene

<400> SEQUENCE: 140

Met Lys Lys Ile Ala Leu Ile Phe Gly Gly Thr Ser Ala Glu Tyr Glu
  1               5                  10                  15

Val Ser Leu Lys Ser Ala Ala Ser Val Leu Ser Val Leu Glu Asn Leu
             20                  25                  30

Asn Val Glu Ile Tyr Arg Ile Gly Ile Ala Ser Asn Gly Lys Trp Tyr
         35                  40                  45

Leu Thr Phe Ser Asp Asn Glu Thr Ile Ala Asn Asp Leu Trp Leu Gln
     50                  55                  60

Asp Lys Lys Leu Asn Glu Ile Thr Pro Ser Phe Asp Gly Arg Gly Phe
 65                  70                  75                  80

Tyr Asp Gln Ala Glu Lys Val Tyr Phe Lys Pro Asp Val Leu Phe Pro
                 85                  90                  95

Met Leu His Gly Gly Thr Gly Glu Asn Gly Thr Leu Gln Gly Val Phe
            100                 105                 110

Glu Cys Met Gln Ile Pro Tyr Val Gly Cys Gly Val Ala Ser Ser Ala
        115                 120                 125

Ile Cys Met Asn Lys Tyr Leu Leu His Gln Phe Ala Lys Ser Val Gly
    130                 135                 140

Val Met Ser Thr Pro Thr Gln Leu Ile Ser Ser Thr Asp Glu Gln Gln
145                 150                 155                 160

Val Ile Lys Asn Phe Thr Glu Leu Tyr Gly Phe Pro Ile Phe Ile Lys
                165                 170                 175

Pro Asn Glu Ala Gly Ser Ser Lys Gly Ile Ser Lys Val His Thr Glu
```

```
            180                 185                 190

Ala Glu Leu Thr Lys Ala Leu Thr Glu Ala Phe Gln Phe Ser Gln Thr
        195                 200                 205

Val Ile Leu Gln Lys Ala Val Ser Gly Val Glu Ile Gly Cys Ala Ile
    210                 215                 220

Leu Gly Asn Asp Gln Leu Leu Val Gly Glu Cys Asp Glu Val Ser Leu
225                 230                 235                 240

Ala Thr Asp Phe Phe Asp Tyr Thr Glu Lys Tyr Gln Met Thr Thr Ala
                245                 250                 255

Lys Leu Thr Val Pro Ala Lys Ile Pro Val Ala Thr Ser Arg Glu Ile
            260                 265                 270

Lys Arg Gln Ala Gln Leu Leu Tyr Gln Leu Leu Gly Cys Gln Gly Leu
        275                 280                 285

Ala Arg Ile Asp Phe Phe Leu Thr Glu Ala Gly Glu Ile Leu Leu Asn
    290                 295                 300

Glu Ile Asn Thr Met Pro Gly Phe Thr Asn His Ser Arg Phe Pro Ala
305                 310                 315                 320

Met Met Ala Ala Thr Gly Ile Thr Tyr Gln Glu Leu Ile Ser Thr Leu
                325                 330                 335

Ile Thr Leu Ala Glu Asp Lys
            340


<210> SEQ ID NO 141
<211> LENGTH: 16
<212> TYPE: PRT
<213> ORGANISM: Unknown
<220> FEATURE:
<223> OTHER INFORMATION: peptide from a microbial resistance gene

<400> SEQUENCE: 141

Ala Leu Thr Glu Ala Phe Gln Phe Ser Gln Thr Val Ile Leu Gln Lys
  1               5                  10                  15


<210> SEQ ID NO 142
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 142

Gly Phe Tyr Asp Gln Ala Glu Lys
  1               5


<210> SEQ ID NO 143
<211> LENGTH: 17
<212> TYPE: PRT
<213> ORGANISM: Unknown
<220> FEATURE:
<223> OTHER INFORMATION: peptide from a microbial resistance gene

<400> SEQUENCE: 143

Ile Ala Leu Ile Phe Gly Gly Thr Ser Ala Glu Tyr Glu Val Ser Leu
  1               5                  10                  15

Lys


<210> SEQ ID NO 144
<211> LENGTH: 8
<212> TYPE: PRT
<213> ORGANISM: Unknown
<220> FEATURE:
```

-continued

<223> OTHER INFORMATION: peptide from a microbial resistance gene

<400> SEQUENCE: 144

Ile Gly Ile Ala Ser Asn Gly Lys
1 5

<210> SEQ ID NO 145
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 145

Ile Pro Val Ala Thr Ser Arg
1 5

<210> SEQ ID NO 146
<211> LENGTH: 11
<212> TYPE: PRT
<213> ORGANISM: Unknown
<220> FEATURE:
<223> OTHER INFORMATION: peptide from a microbial resistance gene

<400> SEQUENCE: 146

Leu Asn Glu Ile Thr Pro Ser Phe Asp Gly Arg
1 5 10

<210> SEQ ID NO 147
<211> LENGTH: 21
<212> TYPE: PRT
<213> ORGANISM: Unknown
<220> FEATURE:
<223> OTHER INFORMATION: peptide from a microbial resistance gene

<400> SEQUENCE: 147

Asn Phe Thr Glu Leu Tyr Gly Phe Pro Ile Phe Ile Lys Pro Asn Glu
1 5 10 15

Ala Gly Ser Ser Lys
20

<210> SEQ ID NO 148
<211> LENGTH: 16
<212> TYPE: PRT
<213> ORGANISM: Unknown
<220> FEATURE:
<223> OTHER INFORMATION: peptide from a microbial resistance gene

<400> SEQUENCE: 148

Gln Ala Gln Leu Leu Tyr Gln Leu Leu Gly Cys Gln Gly Leu Ala Arg
1 5 10 15

<210> SEQ ID NO 149
<211> LENGTH: 18
<212> TYPE: PRT
<213> ORGANISM: Unknown
<220> FEATURE:
<223> OTHER INFORMATION: peptide from a microbial resistance gene

<400> SEQUENCE: 149

Ser Ala Ala Ser Val Leu Ser Val Leu Glu Asn Leu Asn Val Glu Ile
1 5 10 15

Tyr Arg

<210> SEQ ID NO 150

-continued

<211> LENGTH: 22
<212> TYPE: PRT
<213> ORGANISM: Unknown
<220> FEATURE:
<223> OTHER INFORMATION: peptide from a microbial resistance gene

<400> SEQUENCE: 150

Ser Val Gly Val Met Ser Thr Pro Thr Gln Leu Ile Ser Ser Thr Asp
1 5 10 15

Glu Gln Gln Val Ile Lys
20

<210> SEQ ID NO 151
<211> LENGTH: 9
<212> TYPE: PRT
<213> ORGANISM: Unknown
<220> FEATURE:
<223> OTHER INFORMATION: peptide from a microbial resistance gene

<400> SEQUENCE: 151

Val His Thr Glu Ala Glu Leu Thr Lys
1 5

<210> SEQ ID NO 152
<211> LENGTH: 20
<212> TYPE: PRT
<213> ORGANISM: Unknown
<220> FEATURE:
<223> OTHER INFORMATION: peptide from a microbial resistance gene

<400> SEQUENCE: 152

Trp Tyr Leu Thr Phe Ser Asp Asn Glu Thr Ile Ala Asn Asp Leu Trp
1 5 10 15

Leu Gln Asp Lys
20

<210> SEQ ID NO 153
<211> LENGTH: 8
<212> TYPE: PRT
<213> ORGANISM: Unknown
<220> FEATURE:
<223> OTHER INFORMATION: peptide from a microbial resistance gene

<400> SEQUENCE: 153

Tyr Leu Leu His Gln Phe Ala Lys
1 5

<210> SEQ ID NO 154
<211> LENGTH: 7
<212> TYPE: PRT
<213> ORGANISM: Unknown
<220> FEATURE:
<223> OTHER INFORMATION: peptide from a microbial resistance gene

<400> SEQUENCE: 154

Tyr Gln Met Thr Thr Ala Lys
1 5